US008883324B2

(12) United States Patent
Yabunouchi et al.

(10) Patent No.: US 8,883,324 B2
(45) Date of Patent: Nov. 11, 2014

(54) AROMATIC AMINE DERIVATIVE AND ORGANIC ELECTROLUMINESCENT DEVICE USING SAME

(75) Inventors: Nobuhiro Yabunouchi, Sodegaura (JP); Hisayuki Kawamura, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 13/345,536

(22) Filed: Jan. 6, 2012

(65) Prior Publication Data

US 2012/0112176 A1     May 10, 2012

Related U.S. Application Data

(63) Continuation of application No. 11/813,377, filed as application No. PCT/JP2005/023368 on Dec. 20, 2005, now abandoned.

(30) Foreign Application Priority Data

Jan. 5, 2005 (JP) ................................ 2005-001008

(51) Int. Cl.
| H01L 51/54 | (2006.01) |
| C09K 11/06 | (2006.01) |
| C07C 211/61 | (2006.01) |
| H05B 33/20 | (2006.01) |
| C07C 211/58 | (2006.01) |
| C07C 211/54 | (2006.01) |
| H05B 33/14 | (2006.01) |
| H01L 51/00 | (2006.01) |
| H01L 51/50 | (2006.01) |

(52) U.S. Cl.
CPC ...... *H01L 51/006* (2013.01); *C09K 2211/1011* (2013.01); *H01L 51/0062* (2013.01); *H01L 51/0081* (2013.01); *C07C 211/61* (2013.01); *C07C 2103/50* (2013.01); *H01L 51/5048* (2013.01); *H01L 51/5012* (2013.01); *C07C 2103/18* (2013.01); *H05B 33/20* (2013.01); *C07C 2103/97* (2013.01); *C09K 11/06* (2013.01); *C07C 211/58* (2013.01); *C07C 211/54* (2013.01); *H01L 51/0058* (2013.01); *H05B 33/14* (2013.01); *C09K 2211/1007* (2013.01); *C07C 2103/26* (2013.01); *Y10S 428/917* (2013.01)
USPC ........... 428/690; 428/917; 313/502; 313/504; 257/40; 546/308

(58) Field of Classification Search
None
See application file for complete search history.

(56) References Cited

U.S. PATENT DOCUMENTS

| 5,489,495 | A | 2/1996 | Anzai et al. |
| 5,554,450 | A * | 9/1996 | Shi et al. ........................ 428/690 |
| 5,792,557 | A | 8/1998 | Nakaya et al. |
| 6,632,543 | B1 * | 10/2003 | Kawamura ..................... 428/690 |
| 7,839,074 | B2 | 11/2010 | Ikeda et al. |
| 2002/0146589 | A1 * | 10/2002 | Akiyama et al. .............. 428/690 |
| 2003/0205696 | A1 * | 11/2003 | Thoms et al. ............ 252/301.16 |
| 2006/0043858 | A1 | 3/2006 | Ikeda et al. |
| 2006/0134458 | A1 | 6/2006 | Kawamura |
| 2006/0159957 | A1 | 7/2006 | Yabunouchi et al. |
| 2007/0111028 | A1 | 5/2007 | Yabunouchi et al. |
| 2007/0145888 | A1 | 6/2007 | Yabunouchi et al. |
| 2008/0108811 | A1 | 5/2008 | Yabunouchi et al. |

FOREIGN PATENT DOCUMENTS

| EP | 0 314 195 | 5/1989 |
| EP | 0949695 A2 | 10/1999 |
| JP | 1-118146 | 5/1989 |
| JP | 06 011854 | 1/1994 |
| JP | 7 175237 | 7/1995 |
| JP | 10 265773 | 10/1998 |
| JP | 11 35532 | 2/1999 |
| JP | 11-135261 | 5/1999 |
| JP | 11 135261 | 5/1999 |
| JP | 11 288783 | 10/1999 |
| JP | 11 329738 | 11/1999 |
| JP | 2001-039933 | 2/2001 |
| JP | 2001-64241 | 3/2001 |
| JP | 2002 241352 | 8/2002 |
| JP | 2002 249469 | 9/2002 |
| JP | 2003 089682 | 3/2003 |
| JP | 2003-238502 | 8/2003 |
| JP | 2003-238558 | 8/2003 |
| JP | 2004-26732 | 1/2004 |
| JP | 2004-189700 | 7/2004 |
| JP | 2004-262761 | 9/2004 |
| JP | 2005-120030 | 5/2005 |
| WO | WO 01/56091 | 8/2001 |

(Continued)

OTHER PUBLICATIONS

Shirota et al. "Charge Transport in Amorphous Molecular Materials" SPIE Int. Soc. Opt. Eng., 1998, 3476, 132-141. Year of publication: 1998.*

(Continued)

*Primary Examiner* — Andrew K Bohaty
(74) *Attorney, Agent, or Firm* — Oblon, Spivak, McClelland, Maier & Neustadt, L.L.P.

(57) ABSTRACT

Disclosed is an organic electroluminescence device in which an organic thin film which is composed of one or more layers including at least a light-emitting layer is interposed between a cathode and an anode. Since at least one layer of the organic thin film contains a novel aromatic amine derivative, which has an asymmetric structure wherein two different amine units are bonded through a linking group, by itself or as a component of a mixture, molecules are hardly crystallized, thereby improving the production yield of the organic electroluminescence device. This organic electroluminescence device has a long life.

13 Claims, No Drawings

(56) References Cited

FOREIGN PATENT DOCUMENTS

| WO | 03 064373 | 8/2003 |
|---|---|---|
| WO | 2004/018587 | 3/2004 |
| WO | WO 2004/063142 A1 | 7/2004 |
| WO | WO 2006/006505 A1 | 1/2006 |

OTHER PUBLICATIONS

Chou et al. "Electropolymerization of Starburst Triarylamines and Their Applications in Electrochromism and Electroluminescence" Chem. Mater. 2004, 16, 654-661. Date of publication: Jan. 29, 2004.*

European Search Report Issued on 08/29/11, application No. 11171640.3-1211.

Office Action issued Dec. 1, 2010, in Korean Patent Application No. 9-5-2010-055262164.

Nakatsu et al., JP(2000)-327639, Machine Assisted Translation.

Nakatsu et al., JP(2001)-039933, Machine Assisted Translation.

Office Action issued in corresponding Korean Application No. 10-2011-7012532 dated Aug. 29, 2011.

Office Action issued Nov. 15, 2011 in Japanese Patent Application No. 2008-193490.

Office Action issued Jun. 8, 2012, in Taiwan Patent Application No. 95100093.

Office Action issued Jul. 30, 2012, in Korean Patent Application No. 10-2012-70005411.

Office Action issued Aug. 2, 2013, in corresponding Chinese Patent Application No. 201210083974.1 (2013073001046470).

Yi Zhen Su, et al., "Amorphous 2,3-Substituted Thiophenes: Potential Electroluminescent Materials," Chem. Mater (2002) 14 (1884-1890).

* cited by examiner

AROMATIC AMINE DERIVATIVE AND ORGANIC ELECTROLUMINESCENT DEVICE USING SAME

CROSS-REFERENCE TO RELATED APPLICATIONS

The present application is a continuation of U.S. patent application Ser. No. 11/813,377, filed on Jul. 5, 2007, now abandoned, which is a 35 U.S.C. §371 National Stage patent application of International patent application PCT/JP2005/023368, filed on Dec. 20, 2005, which claims priority to Japanese patent application JP 2005-001008, filed on Jan. 5, 2005.

TECHNICAL FIELD

The present invention relates to aromatic amine derivatives and an organic electroluminescence (EL) device using any one of them, in particular, an organic EL device in which a molecule hardly crystallizes, which is produced with improved yields, and which has a long lifetime and an aromatic amine derivative realizing the organic EL device.

BACKGROUND ART

An organic EL device is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported by C. W. Tang et al. of Eastman Kodak Company (C. W. Tang and S. A. Vanslyke, Applied Physics Letters, Volume 51, Pages 913, 1987 or the like), many studies have been conducted on organic EL devices using organic materials as the constituent materials. Tang et al. used tris(8-quinolinolato)aluminum for a light emitting layer and a triphenyldiamine derivative for a hole transporting layer. Advantages of the laminate structure are that the efficiency of hole injection into the light emitting layer can be increased, that the efficiency of forming exciton which are formed by blocking and recombining electrons injected from the cathode can be increased, and that exciton formed within the light emitting layer can be enclosed. As described above, for the structure of the organic EL device, a two-layered structure having a hole transporting (injecting) layer and an electron-transporting light emitting layer and a three-layered structure having a hole transporting (injecting) layer, a light emitting layer, and an electron-transporting (injecting) layer are well known. To increase the efficiency of recombination of injected holes and electrons in the devices of the laminate type, the structure of the device and the process for forming the device have been studied.

In general, when an organic EL device is driven or stored in an environment of a high temperature, adverse effects such as a change in the luminescent color, a decrease in emission efficiency, an increase in the voltage for driving, and a decrease in the lifetime of light emission arise. To prevent the adverse effects, it has been necessary that the glass transition temperature (Tg) of the hole transporting material be elevated. Therefore, it is necessary that the many aromatic groups be held within the molecule of the hole transporting material, for example, the aromatic diamine derivative in Patent Document 1 and the fused aromatic ring diamine derivative in Patent Document 2, and in general, a structure having 8 to 12 benzene rings may preferably be used.

However, when a large number of aromatic groups are present in a molecule, crystallization is apt to occur upon production of an organic EL device through the formation of a thin film by using those hole transporting materials. As a result, there arises a problem such as the clogging of the outlet of a crucible to be used in vapor deposition or a reduction in yields of the organic EL device due to the generation of a fault of the thin film resulting from the crystallization. In addition, a compound having a large number of aromatic groups in any one of its molecules generally has a high glass transition temperature (Tg), but has a high sublimation temperature. Accordingly, there arises a problem in that the lifetime of the compound is short because a phenomenon such as decomposition at the time of vapor deposition or the formation of a nonuniform deposition film is expected to occur.

Meanwhile, there is a known document disclosing an asymmetric aromatic amine derivative. For example, Patent Document 3 describes an aromatic amine derivative having an asymmetric structure. However, the document has no specific example, and has no description concerning characteristics of an asymmetric compound. In addition, Patent Document 4 describes an asymmetric aromatic amine derivative having phenanthrene as an example. However, the derivative is treated in the same way as that of a symmetric compound, and the document has no description concerning characteristics of an asymmetric compound. In addition, none of those patents explicitly describes a method of producing an asymmetric compound in spite of the fact that the asymmetric compound requires a special synthesis method. Further, Patent Document 5 describes a method of producing an aromatic amine derivative having an asymmetric structure, but has no description concerning characteristics of an asymmetric compound. Patent Document 6 describes an asymmetric compound which has a high glass transition temperature and which is thermally stable, but exemplifies only a compound having carbazole. In addition, the inventors of the present invention have produced a device by using the compound. As a result, they have found that a problem lies in the short lifetime of the device.

As described above, an organic EL device having a long lifetime has been reported, but it cannot be said yet that the device always shows sufficient performance. In view of the foregoing, the development of an organic EL device having further excellent performance has been strongly desired.

[Patent Document 1] U.S. Pat. No. 4,720,432
[Patent Document 2] U.S. Pat. No. 5,061,569
[Patent Document 3] JP-A-08-48656
[Patent Document 4] JP-A-11-135261
[Patent Document 5] JP-A-2003-171366
[Patent Document 6] U.S. Pat. No. 6,242,115

DISCLOSURE OF THE INVENTION

Problems to be Solved by the Invention

The present invention has been made with a view to solving the above-mentioned problems, and an object of the present invention is to provide an organic EL device, in which a molecule hardly crystallizes, which can be produced with improved yields, and which has a long lifetime, and an aromatic amine derivative realizing the organic EL device.

Means for Solving the Problems

The inventors of the present invention have made extensive studies with a view to achieving the above-mentioned object. As a result, they have found that the use of a novel aromatic amine derivative having an asymmetric structure in which two different amine units are bonded through a linking group as represented by the following general formula (1) as a material for an organic EL device, in particular, a hole transporting material can solve the above-mentioned problems. Thus, they have completed the present invention.

In addition, the inventors of the present invention have found that an amino group substituted by an aryl group is suitable as an asymmetric amine unit. An interaction between molecules of the amine unit is small because the unit has steric hindrance. Accordingly, the unit has effects such that: crystallization is suppressed; yield in which an organic EL device is produced is improved; decomposition of a molecule is suppressed at the time of vapor deposition because it is possible to deposit at a low sublimation temperature; and an organic EL device having a long lifetime can be provided. It has been found that the asymmetric amine unit can provide an organic EL device having a significantly long lifetime, in particular, when the amine unit is combined with a blue light emitting device.

That is, the present invention provides an aromatic amine derivative represented by the following general formula (1):

A-L-B      (1)

where:

L represents a linking group composed of a substituted or unsubstituted arylene group having 5 to 50 ring atoms, or a linking group obtained by bonding multiple substituted or unsubstituted arylene groups each having 5 to 50 ring atoms through a single bond, an oxygen atom, a sulfur atom, a nitrogen atom, or a saturated or unsaturated, divalent aliphatic hydrocarbon group having 1 to 20 ring carbon atoms;

A represents a diarylamino group represented by the following general formula (2); and B represents a diarylamino group represented by the following general formula (3) provided that A and B are not identical to each other:

(2)

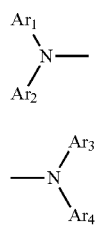

(3)

where $Ar_1$ to $Ar_4$ each independently represent a substituted or unsubstituted aryl group having 5 to 50 ring atoms provided that three or more of $Ar_1$ to $Ar_4$ represent aryl groups different from one another.

The present invention provides an aromatic amine derivative represented by the general formula (1), in which all four of $Ar_1$ to $Ar_4$ in the general formulae (2) and (3) represent aryl groups different from one another.

The present invention provides an aromatic amine derivative represented by the general formula (1), in which $Ar_3$ and $Ar_4$ in the general formula (3) each independently represent a group represented by the following general formula (4):

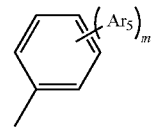

(4)

where $Ar_5$ represents a substituted or unsubstituted aryl group having 5 to 50 ring atoms, and m represents an integer of 1 to 5.

The present invention provides an aromatic amine derivative represented by the general formula (1), in which $Ar_3$ and $Ar_4$ in the general formula (3) each independently represent a group represented by the following general formula (5):

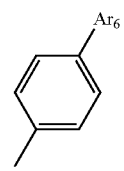

(5)

where $Ar_6$ represents a substituted or unsubstituted aryl group having 5 to 50 ring atoms.

The present invention provides an aromatic amine derivative represented by the general formula (1), in which $Ar_1$ represents a substituted or unsubstituted naphthyl group, and $Ar_3$ and $Ar_4$ each independently represent a group represented by the general formula (5).

The present invention provides an aromatic amine derivative represented by the general formula (1), in which $Ar_2$ in the general formula (2) and $Ar_4$ in the general formula (3) each independently represent a group represented by the following general formula (4):

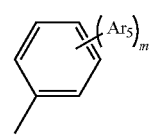

(4)

where $Ar_5$ represents a substituted or unsubstituted aryl group having 5 to 50 ring atoms, and m represents an integer of 1 to 5.

The present invention provides an aromatic amine derivative represented by the general formula (1), in which $Ar_2$ in the general formula (2) and $Ar_4$ in the general formula (3) each independently represent a group represented by the following general formula (5):

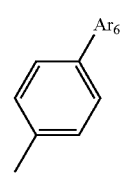

(5)

where $Ar_6$ represents a substituted or unsubstituted aryl group having 5 to 50 ring atoms.

The present invention provides an aromatic amine derivative represented by the general formula (1), in which $Ar_1$ represents a substituted or unsubstituted fused ring group having 11 to 50 ring atoms, and $Ar_3$ and $Ar_4$, or $Ar_2$ and $Ar_4$ each independently represent a group represented by the above-mentioned general formula (4) or (5).

The present invention provides an aromatic amine derivative represented by the general formula (1), in which $Ar_1$ and $Ar_3$ each independently represent a substituted or unsubstituted fused ring group having 10 to 50 ring atoms.

The present invention provides an aromatic amine derivative represented by the general formula (1), in which $Ar_1$ and $Ar_2$ each independently represent a substituted or unsubstituted fused ring group having 10 to 50 ring atoms.

The present invention provides an aromatic amine derivative represented by the general formula (1), in which $Ar_3$ and $Ar_4$ are identical to each other, and $Ar_3$ and $Ar_4$, or $Ar_2$ and $Ar_4$ each independently represent a group represented by the above-mentioned general formula (4) or (5), or $Ar_1$ alone represents, or $Ar_1$ and $Ar_3$ each represent, a fused ring.

The present invention provides an aromatic amine derivative represented by the general formula (1), in which $Ar_2$ and $Ar_3$ are identical to each other, and $Ar_3$ and $Ar_4$, or $Ar_2$ and $Ar_4$ each independently represent a group represented by the above-mentioned general formula (4) or (5), or $Ar_1$ alone represents, or $Ar_1$ and $Ar_3$ each represent, a fused ring.

The present invention provides an aromatic amine derivative represented by the general formula (1), in which a total number of the ring atoms of the aryl groups represented by $Ar_1$ to $Ar_4$ is 41 to 96.

The present invention provides an aromatic amine derivative represented by the general formula (1), in which a total number of the ring atoms of the aryl groups represented by $Ar_1$ to $Ar_4$ is 45 to 72.

The present invention provides any one of the aromatic amine derivative as described above, which is a material for an organic electroluminescence device.

The present invention provides any one of the aromatic amine derivatives as described above, which is a hole transporting material for an organic electroluminescence device.

The present invention provides an organic electroluminescence device including an organic thin film layer composed of one or more layers including at least a light emitting layer, the organic thin film layer being interposed between a cathode and an anode in which at least one layer of the organic thin film layer contains anyone of the aromatic amine derivatives as described above alone or as a component of a mixture.

The present invention provides the organic electroluminescence device as described above, in which the organic thin film layer has a hole transporting layer, and the hole transporting layer contains any one of the aromatic amine derivatives alone or as a component of a mixture.

The present invention provides the organic electroluminescence device as descried above, in which the light emitting layer contains an arylamine compound and/or a styrylamine compound.

Further, the present invention provides any one of the organic electroluminescence devices as described above which emits bluish light.

Effect of the Invention

An aromatic amine and an organic EL device using the aromatic amine derivative of the present invention, which hardly cause the crystallization of a molecule, can improve yields upon production of the organic EL device, and can increase the lifetime of the organic EL device.

BEST MODE FOR CARRYING OUT THE INVENTION

An aromatic amine derivative of the present invention is represented by the following general formula (1).

$$A\text{-}L\text{-}B \tag{1}$$

In the general formula (1), L represents (I) a linking group composed of a substituted or unsubstituted arylene group having 5 to 50 ring atoms, or (II) a linking group obtained by bonding multiple substituted or unsubstituted arylene groups each having 5 to 50 ring atoms through (II-1) a single bond, (II-2) an oxygen atom (—O—), (II-3) a sulfur atom (—S—), (II-4) a nitrogen atom (—NH— or —NR— [where R represents a substituent]), or (II-5) a saturated or unsaturated, divalent aliphatic hydrocarbon group having 1 to 20 ring carbon atoms.

Examples of the arylene group having 5 to 50 ring atoms in each of the above-mentioned items (I) and (II) include a 1,4-phenylene group, a 1,2-phenylene group, a 1,3-phenylene group, a 1,4-naphthylene group, a 2,6-naphthylene group, a 1,5-naphthylene group, a 9,10-anthranylene group, a 9,10-phenanthrenylene group, a 3,6-phenanthrenylene group, a 1,6-pyrenylene group, a 2,7-pyrenylene group, a 6,12-chrysenylene group, a 1,1'-biphenylene group, a 4,4'-biphenylene group, a 3,3'-biphenylene group, a 2,2'-biphenylene group, a 2,7-fluorenylene group, a 2,5-thiophenylene group, a 2,5-silolylene group, a 2,5-oxadiazolylene group, and a terphenylene group. Of those, a 1,4-phenylene group, a 1,2-phenylene group, a 1,3-phenylene group, a 1,4-naphthylene group, a 9,10-anthranylene group, a 6,12-chrysenylene group, a 4,4'-biphenylene group, a 3,3'-biphenylene group, a 2,2'-biphenylene group, and a 2,7-fluorenylene group are preferable.

The saturated or unsaturated, divalent aliphatic hydrocarbon group having 1 to 20 ring carbon atoms in the above-mentioned item (II-5) may be linear, branched, or cyclic, and examples of the group include a methylene group, an ethylene group, a propylene group, an isopropylene group, an ethylidene group, a cyclohexylidene group, and an adamantylene group.

L preferably represents a phenylene group, a biphenylene group, a terphenylene group, or a fluorenylene group, more preferably represents a biphenylene group, or particularly preferably represents a 1,1'-biphenylene group.

In the general formula (1), A represents a diarylamino group represented by the following general formula (2).

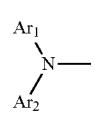
(2)

In the general formula (1), B represents a diarylamino group represented by the following general formula (3).

(3)

It should be noted that A and B in the general formula (1) are not identical to each other.

In the general formulae (2) and (3), $Ar_1$ to $Ar_4$ each independently represent a substituted or unsubstituted aryl group having 5 to 50 ring atoms.

Examples of the aryl groups of $Ar_1$ to $Ar_4$ include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, a fluoranthenyl group, a fluorenyl group, a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, and a 4-t-butyl-3-indolyl group.

Of those, a phenyl group, a naphthyl group, a biphenyl group, an anthranyl group, a phenanthryl group, a pyrenyl group, a chrysenyl group, a fluoranthenyl group, and a fluorenyl group are preferable.

The aromatic amine derivative of the present invention is preferably such that $Ar_1$ to $Ar_4$ in the general formulae (1) to (3) represent groups different from one another.

The aromatic amine derivative of the present invention is preferably such that at least two of $Ar_2$ to $Ar_4$ in the general formulae (1) to (3) each represent an aryl group represented by the following general formula (4), and is more preferably such that at least two of them each represent an aryl group represented by the following general formula (5):

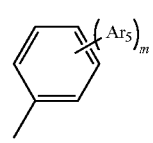
(4)

where $Ar_5$ represents a substituted or unsubstituted aryl group having 5 to 50 ring atoms, examples of the aryl group include the same examples as those described for the aryl group represented by any one of $Ar_1$ to $Ar_4$, and m represents an integer of 1 to 5;

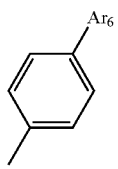 (5)

where Ar₆ represents a substituted or unsubstituted aryl group having to 50 ring atoms.

Examples of a substituent for each of Ar₁ to Ar₆ and L include a substituted or unsubstituted aryl group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 1 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, an amino group substituted by a substituted or unsubstituted aryl group having 5 to 50 ring atoms, a halogen atom, a cyano group, a nitro group, a hydroxyl group, and a carboxyl group.

The substituted or unsubstituted aryl group having 5 to 50 ring atoms, which is a substituent for each of Ar₁ to Ar₆ and L includes the same examples as those described for the above-mentioned Ar₁ to Ar₆.

Examples of the substituted or unsubstituted alkyl group having 1 to 50 carbon atoms, which is a substituent for each of Ar₁ to Ar₆ and L include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 1,3-dihydroxy-2-methyl-2-propyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 1,3-dichloro-2-methyl-2-propyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 1,3-dibromo-2-methyl-2-propyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 1,3-diiodo-2-methyl-2-prpoyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 1,3-diamino-2-methyl-2-propyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 1,3-dicyano-2-methyl-2-propyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 1,3-dinitro-2-methyl-2-propyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group.

The substituted or unsubstituted alkoxy group having 1 to 50 carbon atoms, which is a substituent for each of Ar₁ to Ar₆ and L is represented by —OY, and examples of Y include the same examples as those described for the above-mentioned alkyl group.

Examples of the substituted or unsubstituted aralkyl group having 6 to 50 ring atoms, which is a substituent for each of Ar₁ to Ar₆ and L include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group.

The substituted or unsubstituted aryloxy group having 5 to 50 ring atoms as a substituent for each of Ar₁ to Ar₆ and L is represented by —OY', and examples of Y' include the same examples as those described for the aryl group represented by any one of Ar₁ to Ar₄.

The substituted or unsubstituted arylthio group having 5 to 50 ring atoms as a substituent for each of Ar₁ to Ar₆ and L is represented by —SY', and examples of Y' include the same examples as those described for the aryl group represented by any one of Ar₁ to Ar₄.

The substituted or unsubstituted alkoxycarbonyl group having 1 to 50 carbon atoms as a substituent for each of Ar₁ to Ar₆ and L is a group represented by —COOY, and examples of Y include the same examples as those described for the alkyl group.

Examples of a substituted or unsubstituted aryl group having 5 to 50 ring atoms in the amino group substituted by the aryl group as a substituent for each of Ar₁ to Ar₆ and L include the same examples as those described for the aryl group represented by any one of Ar₁ to Ar₄.

Examples of the halogen atom as a substituent for each of Ar₁ to Ar₆ and L include a fluorine atom, a chlorine atom, a bromine atom, and an iodine atom.

The aromatic amine derivative of the present invention is preferably a material for an organic EL device, and more preferably a hole transporting material for an organic EL device.

Specific examples of the aromatic amine derivative represented by the general formula (1) of the present invention are shown below. However, the present invention is not limited to these exemplified compounds.

Specific Example 1
Specific Example 2
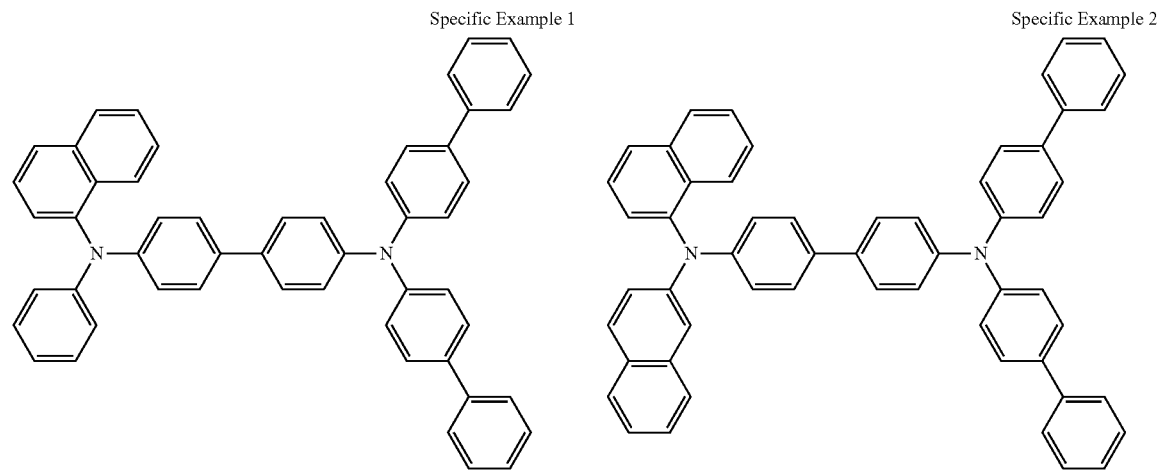
Specific Example 3
Specific Example 4
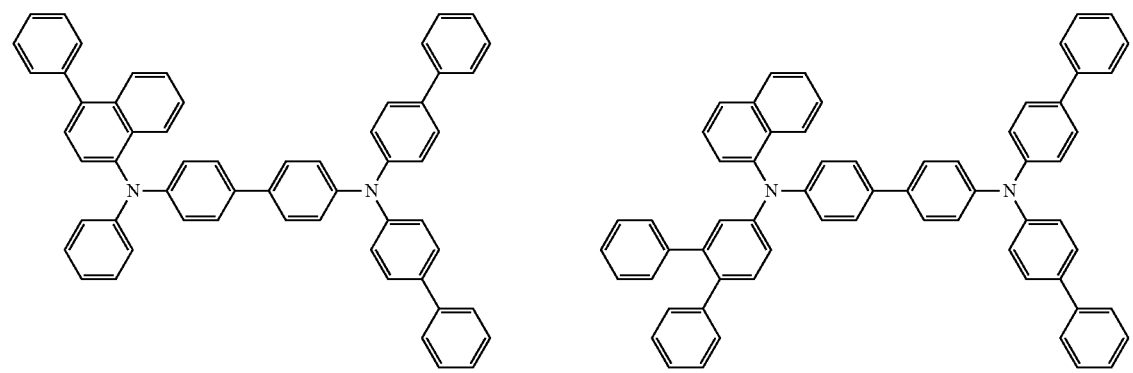
Specific Example 5
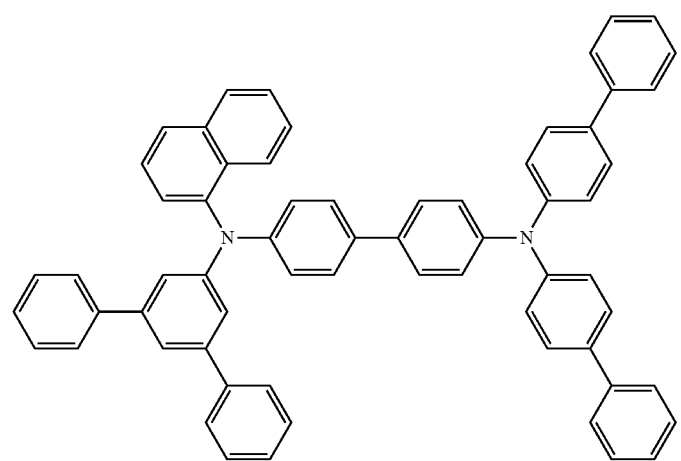

Specific Example 6
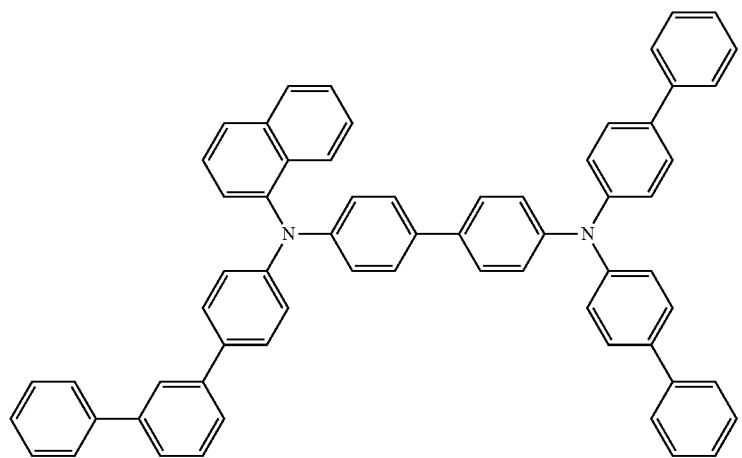
Specific Example 7
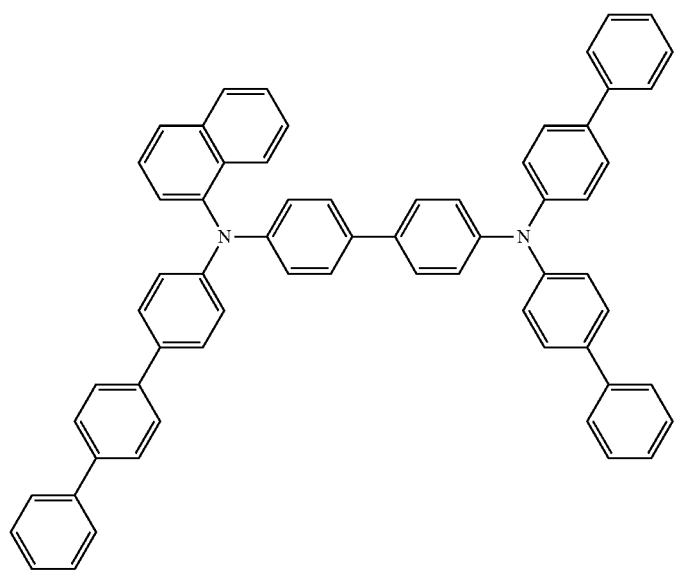
Specific Example 8
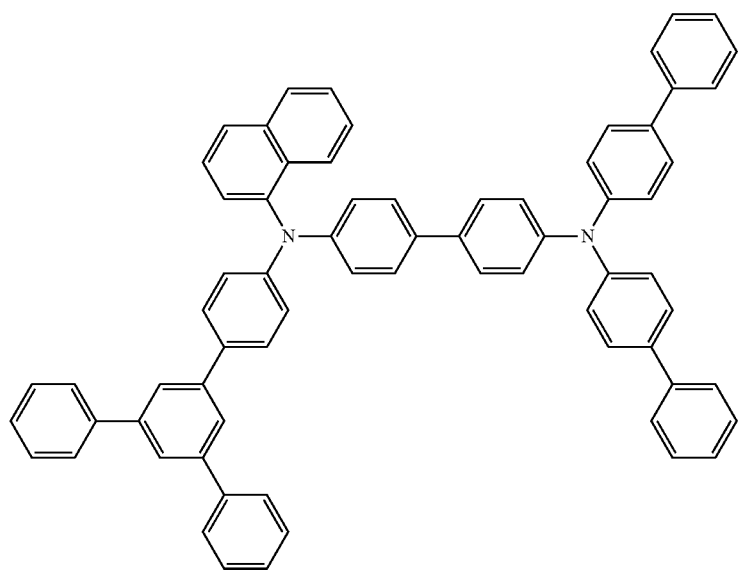

-continued
Specific Example 9
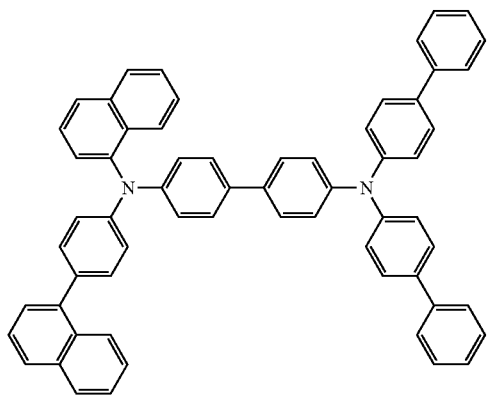
Specific Example 10
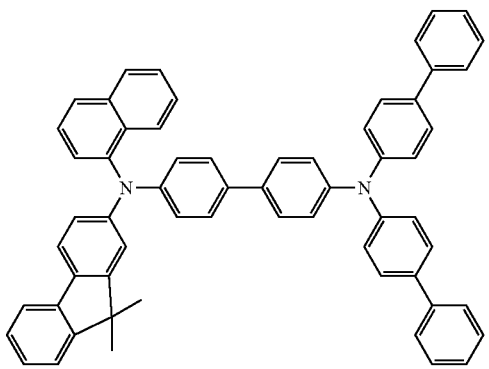
Specific Example 11
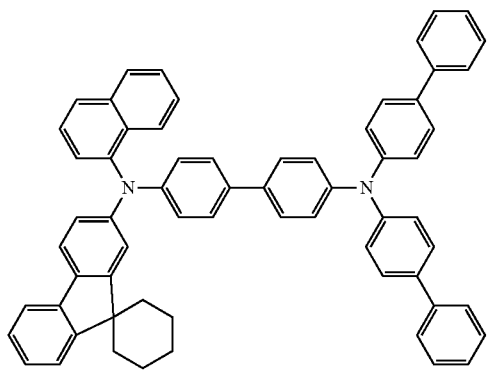
Specific Example 12
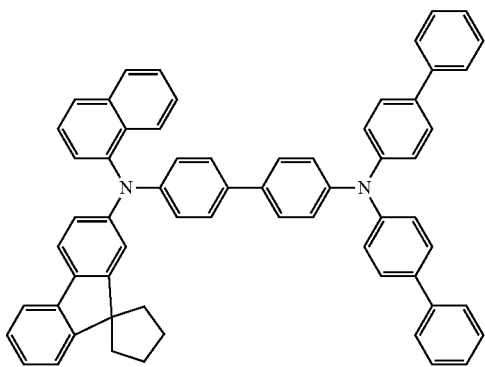
Specific Example 13
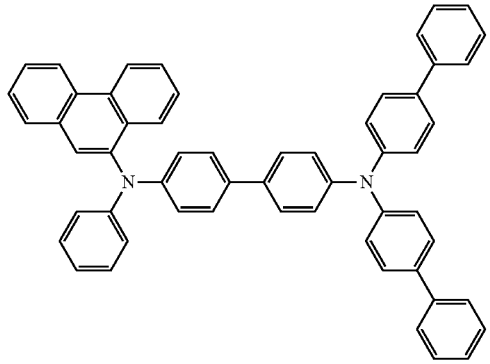
Specific Example 14
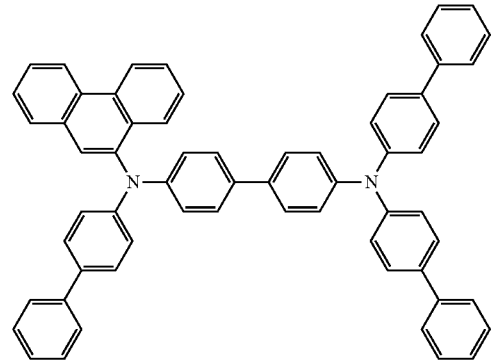
Specific Example 15
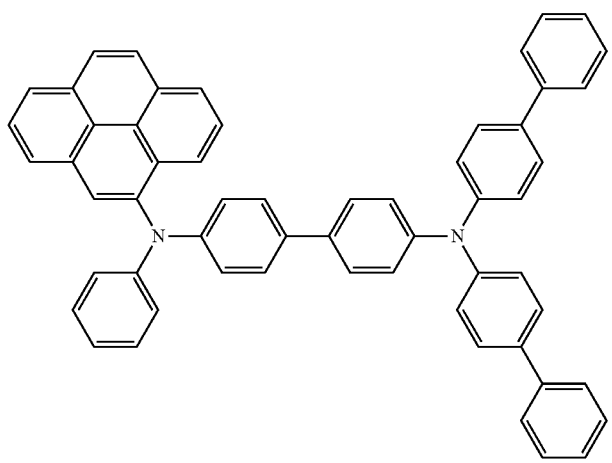

Specific Example 16
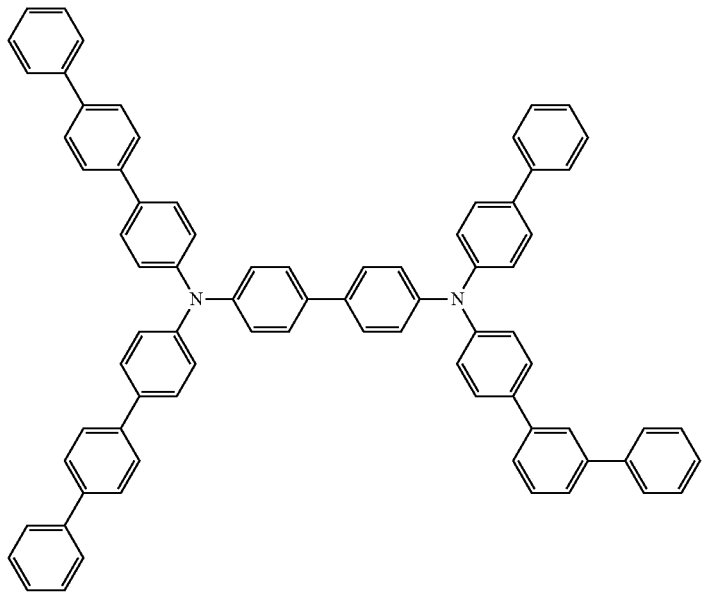
Specific Example 17
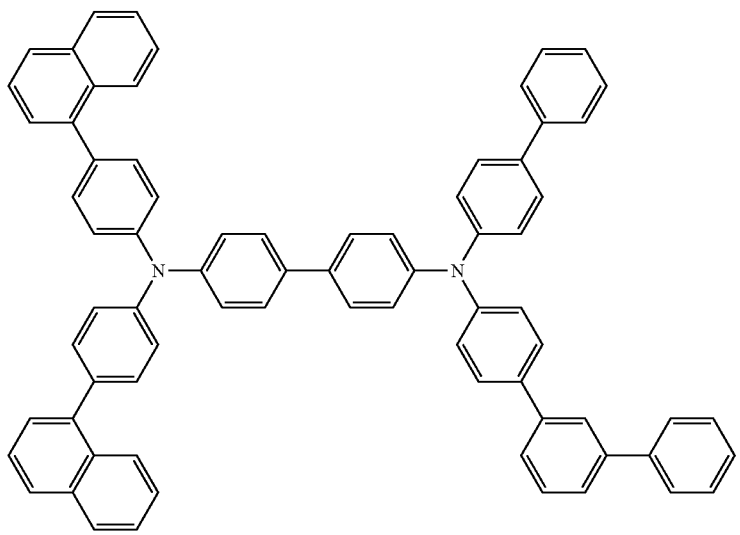
Specific Example 18
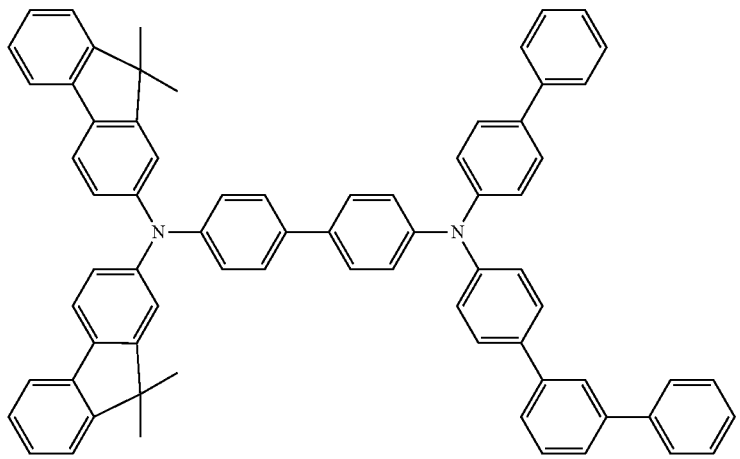

Specific Example 19
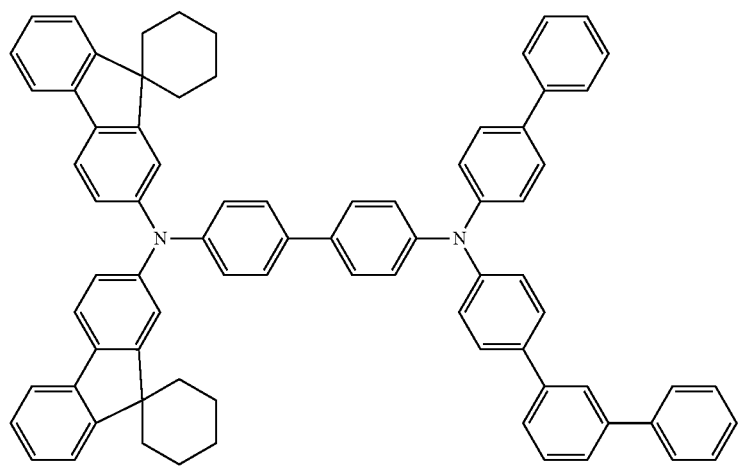
Specific Example 20
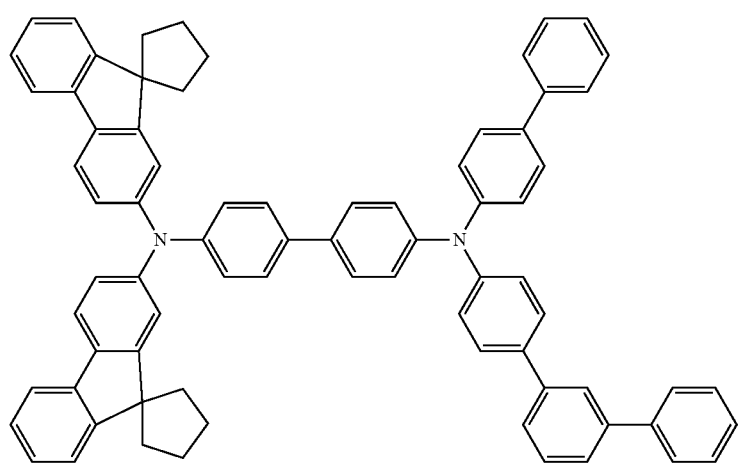
Specific Example 21
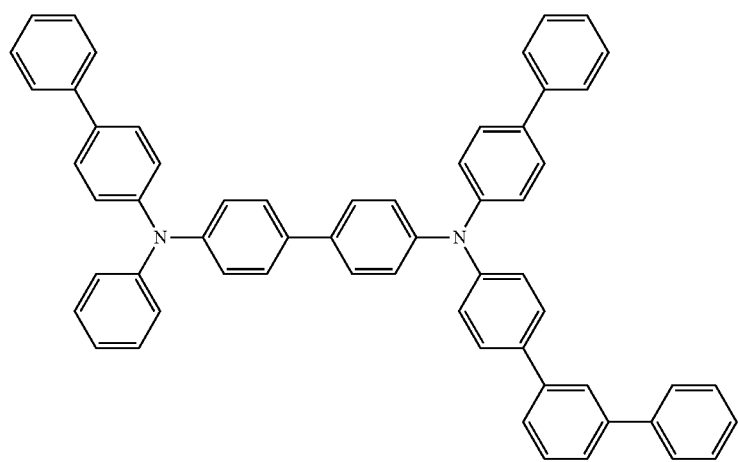

-continued
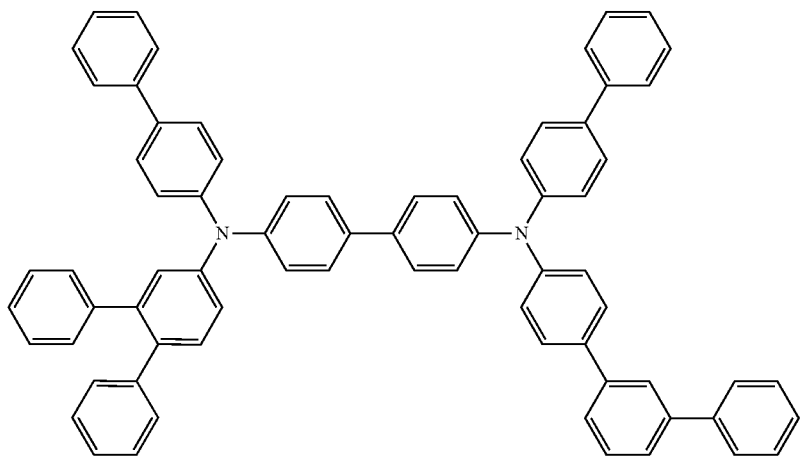
Specific Example 22
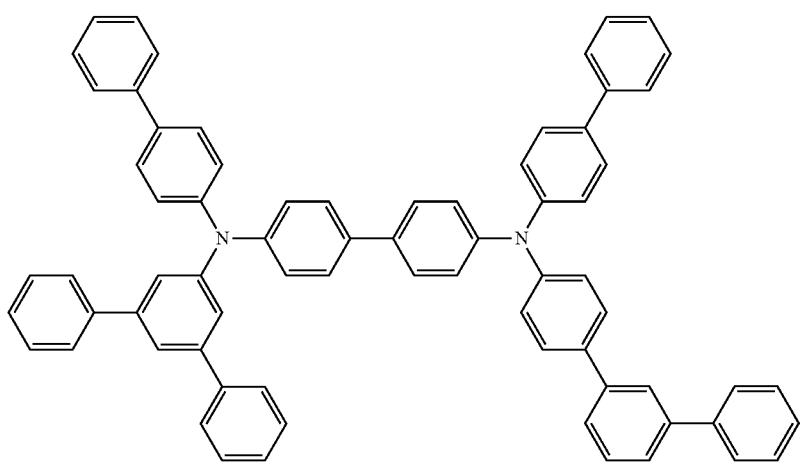
Specific Example 23
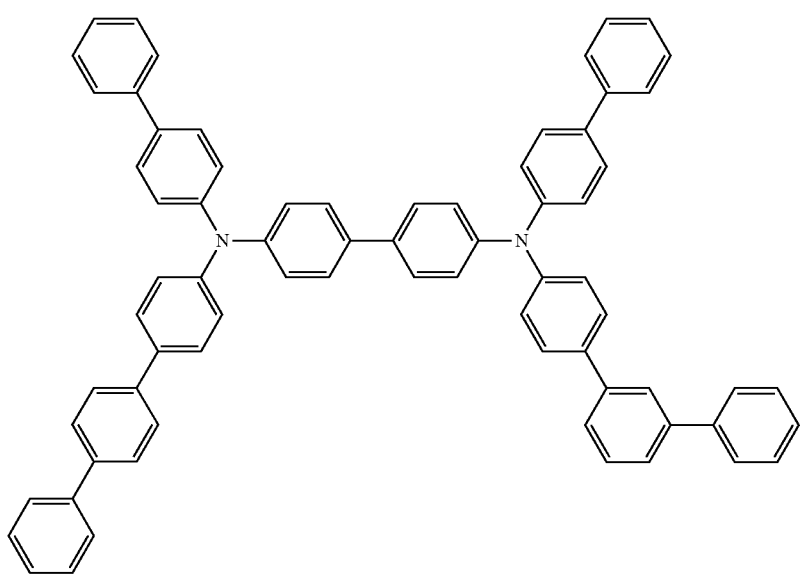
Specific Example 24

-continued
Specific Example 25
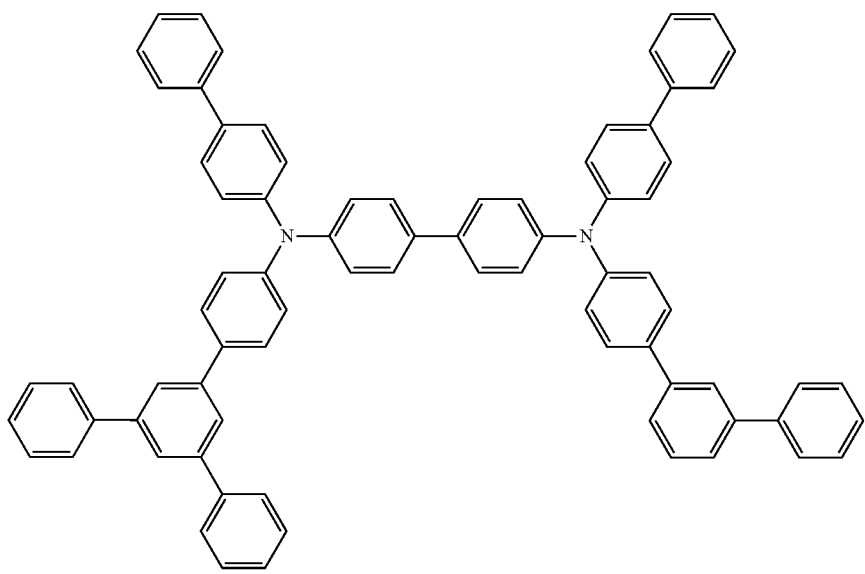
Specific Example 26
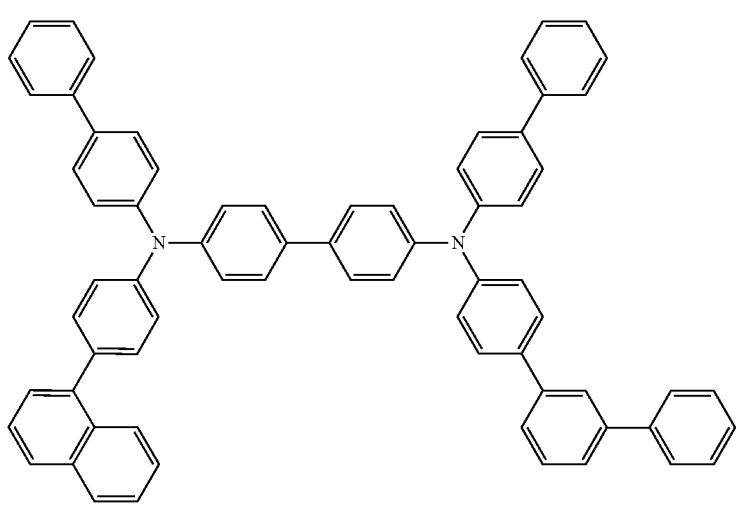
Specific Example 27
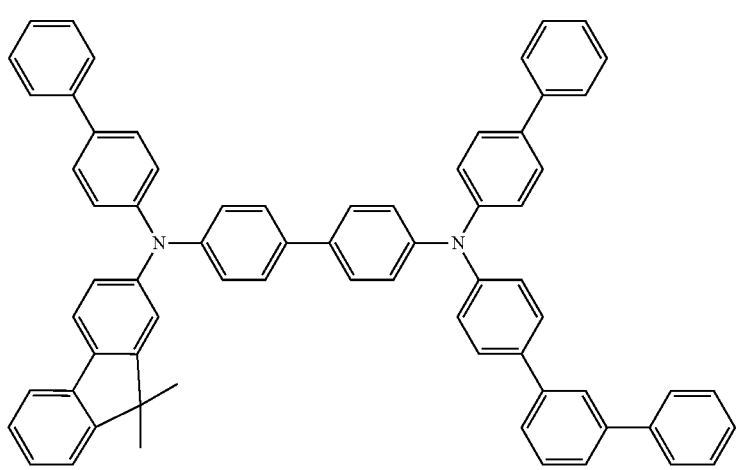

Specific Example 28
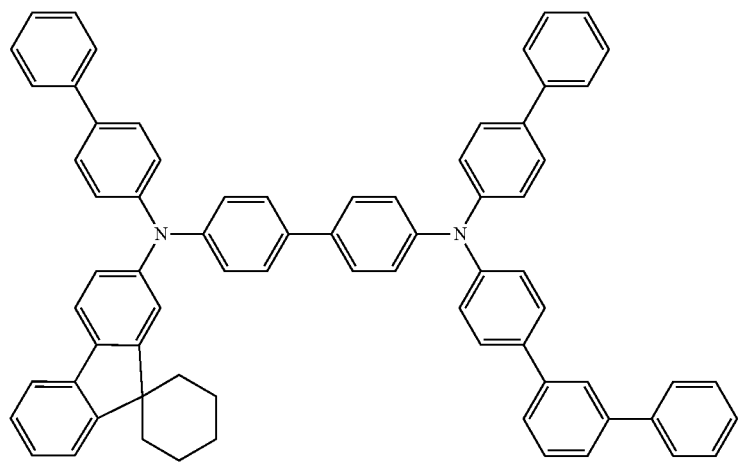
Specific Example 29
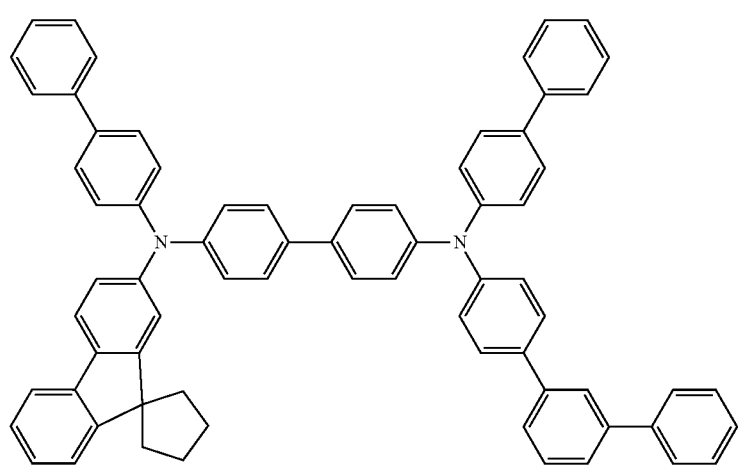
Specific Example 30
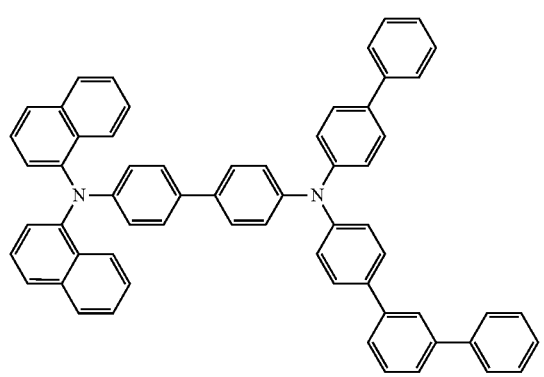
Specific Example 31
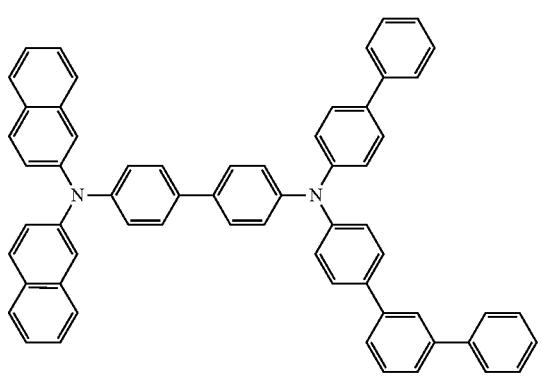

-continued
Specific Example 32
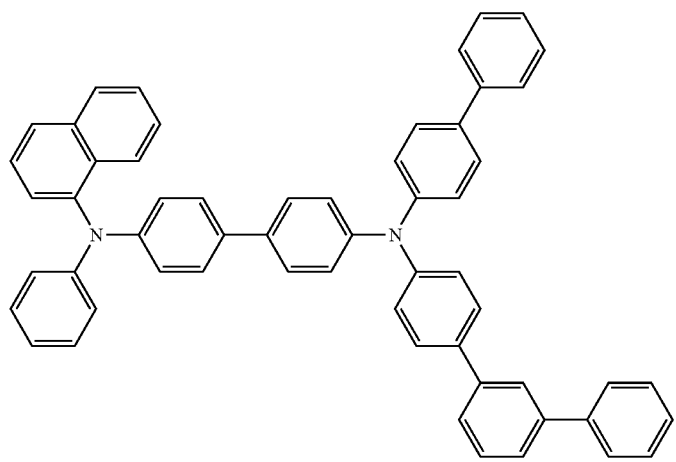
Specific Example 33
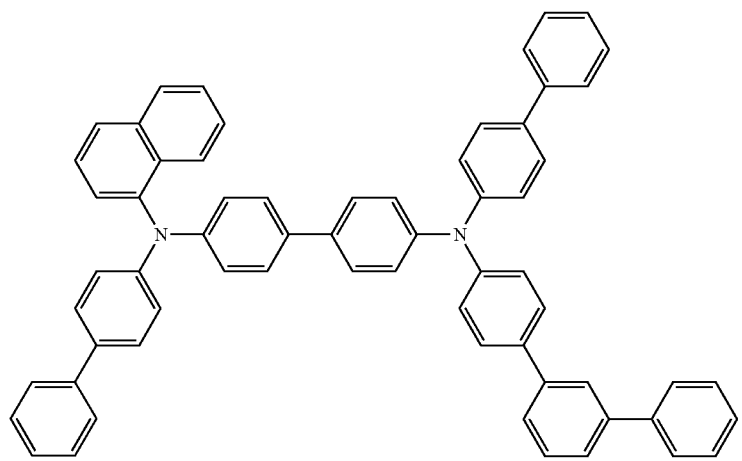
Specific Example 34
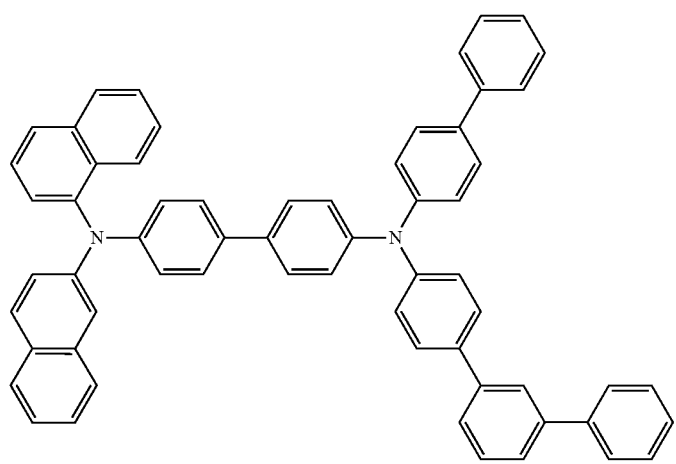

Specific Example 35
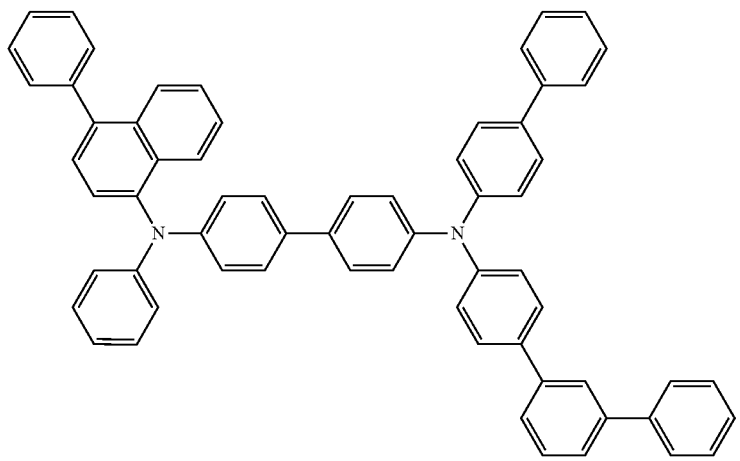
Specific Example 36
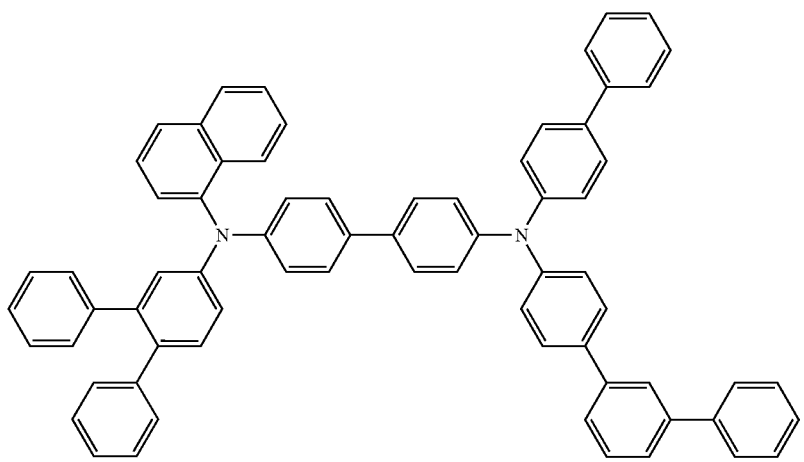
Specific Example 37
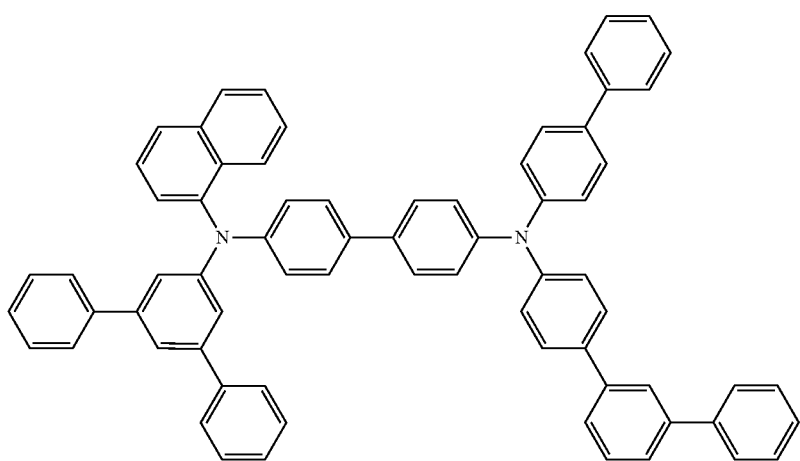

-continued
Specific Example 38
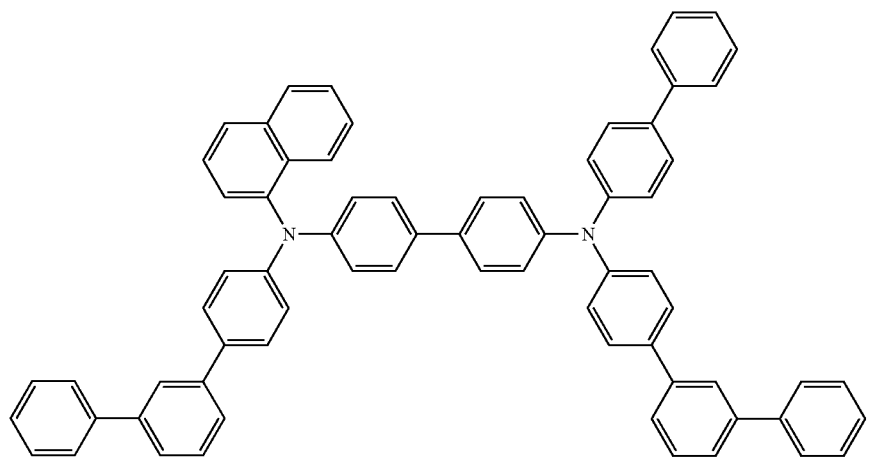
Specific Example 39
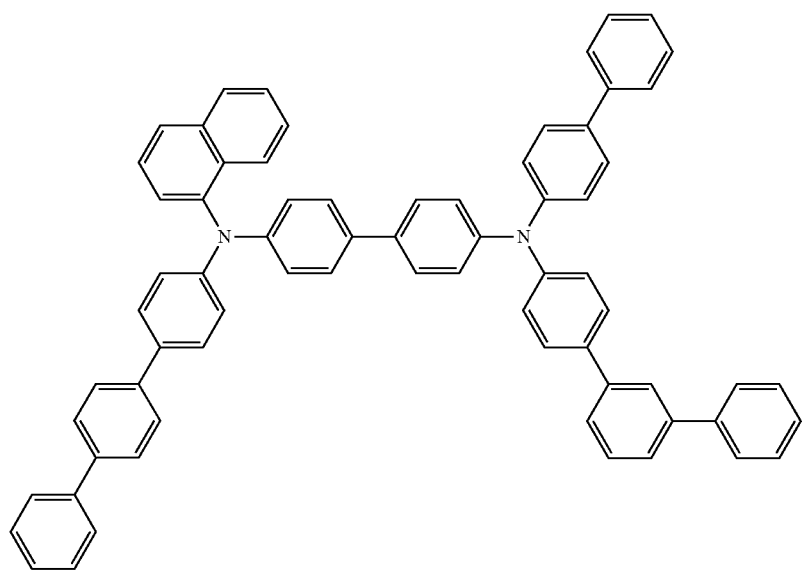
Specific Example 40
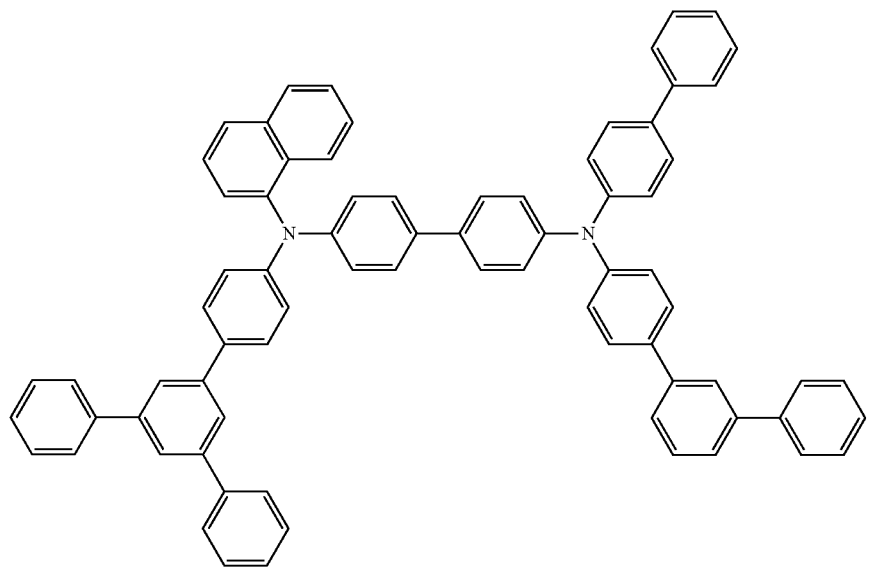

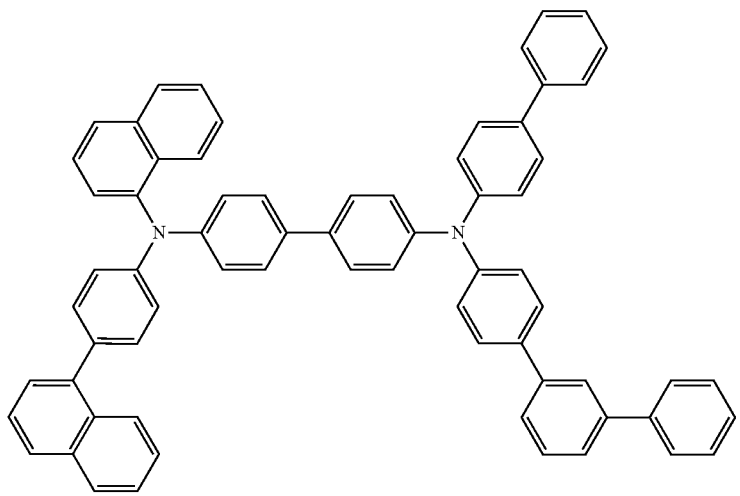
Specific Example 41
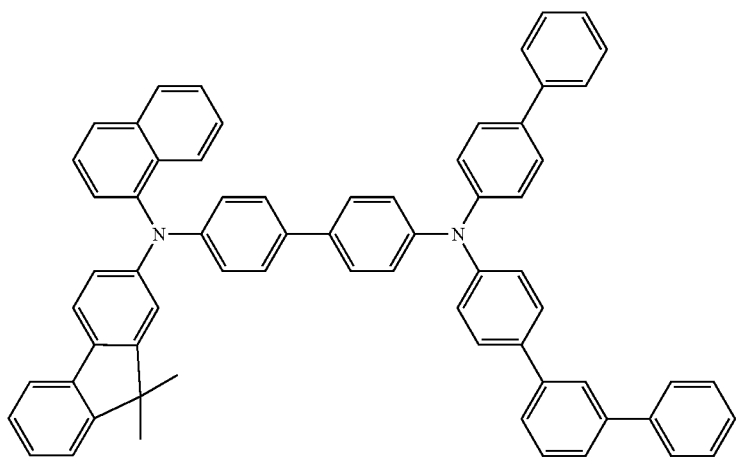
Specific Example 42
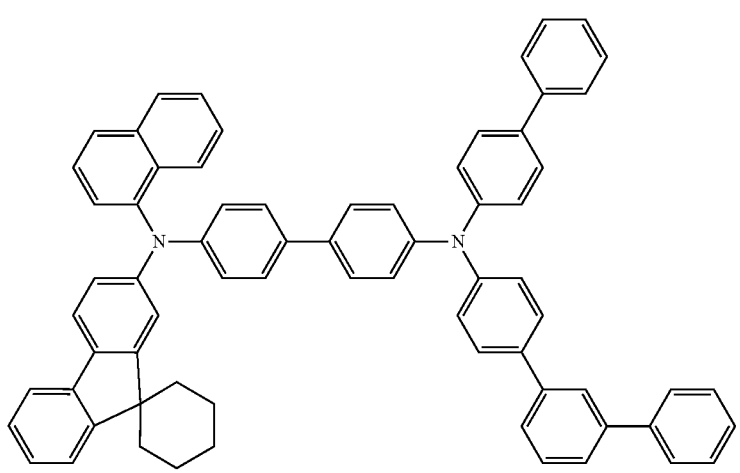
Specific Example 43

-continued
Specific Example 44
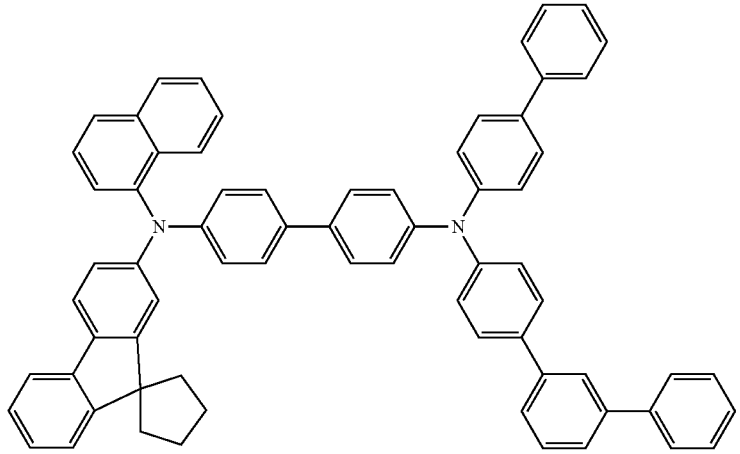
Specific Example 45
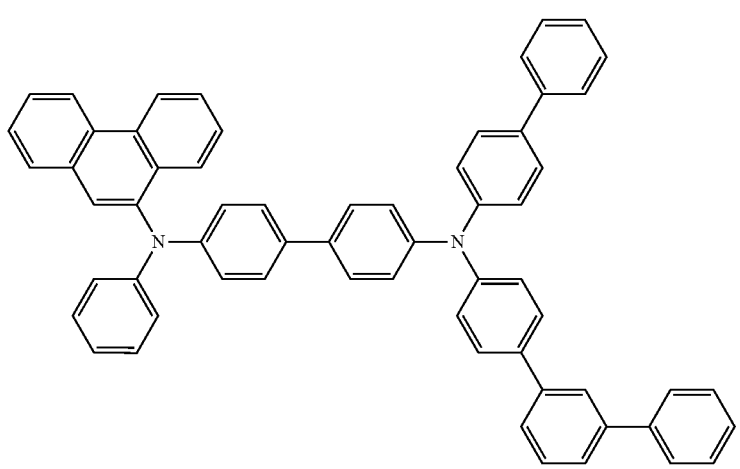
Specific Example 46
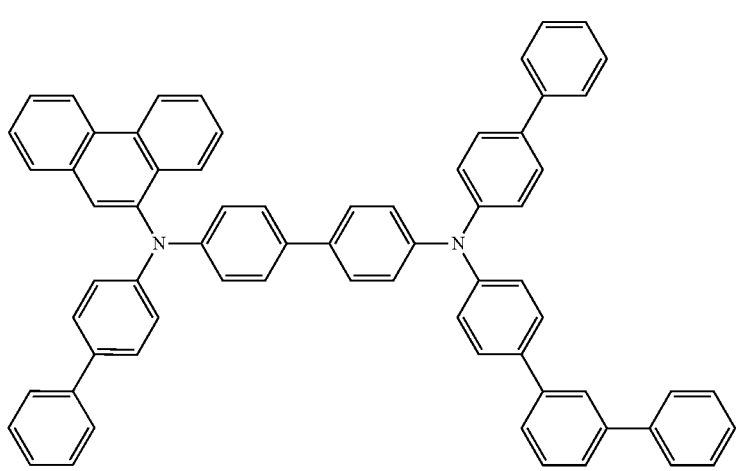

Specific Example 47
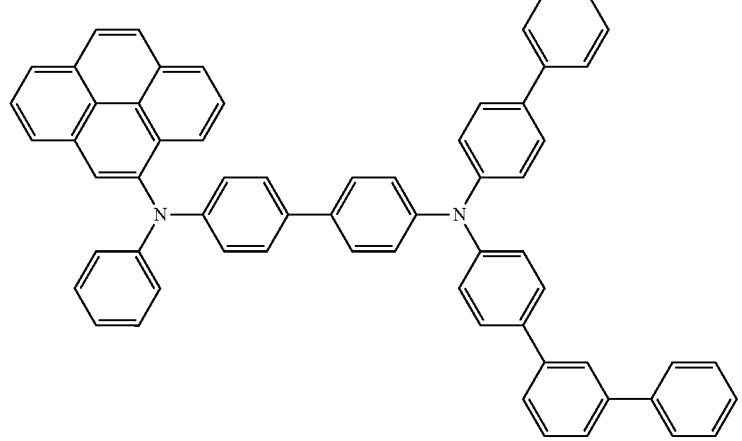
Specific Example 48
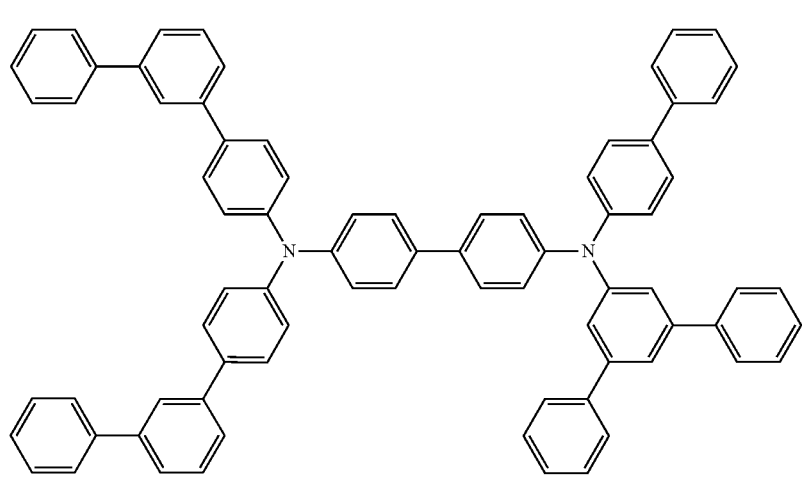
Specific Example 49
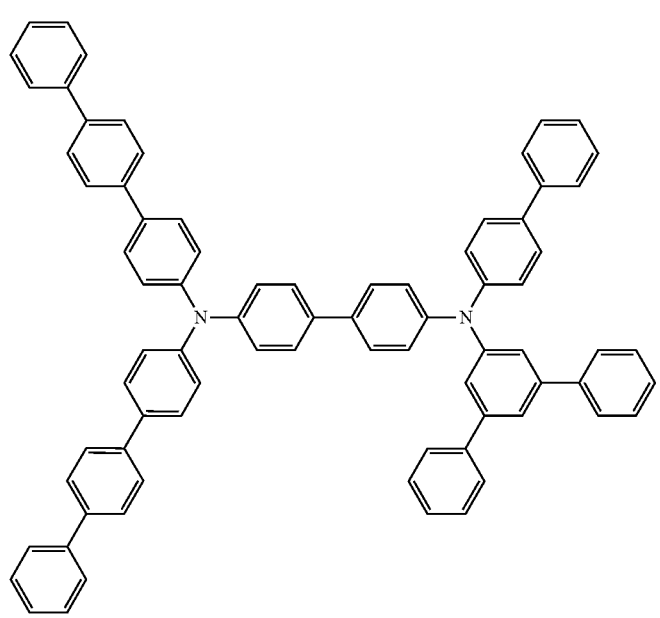

-continued
Specific Example 50
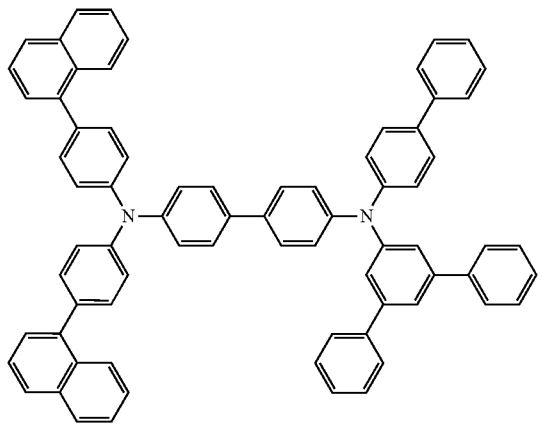
Specific Example 51
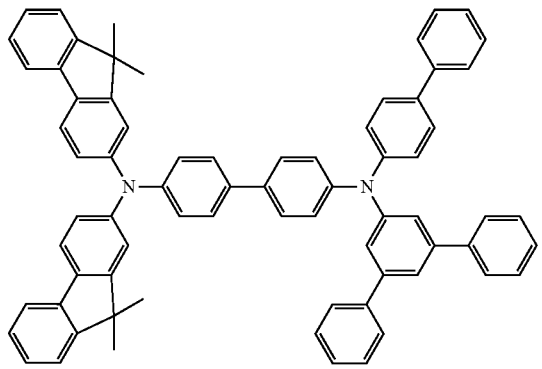
Specific Example 52
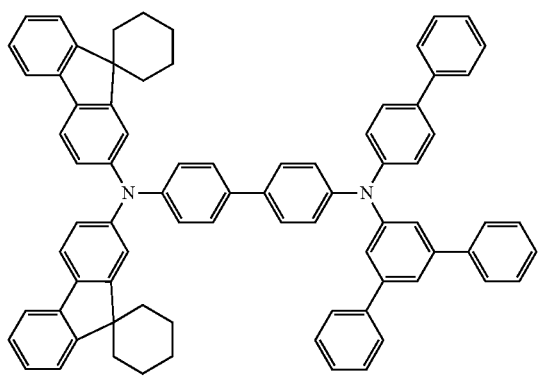
Specific Example 53
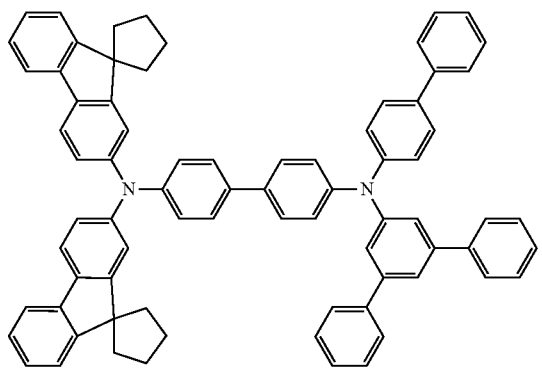
Specific Example 54
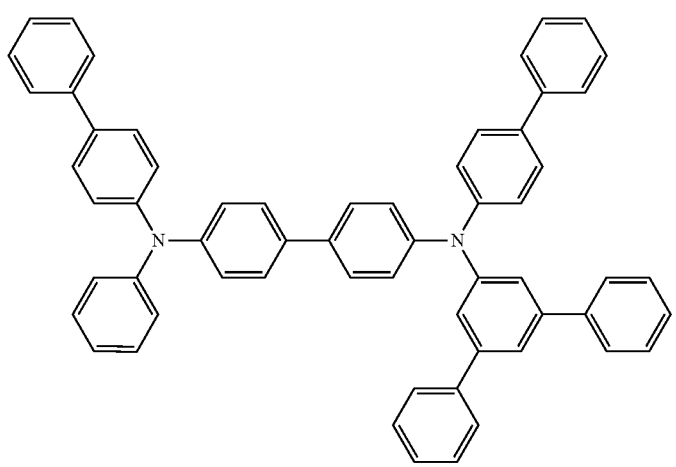

Specific Example 55
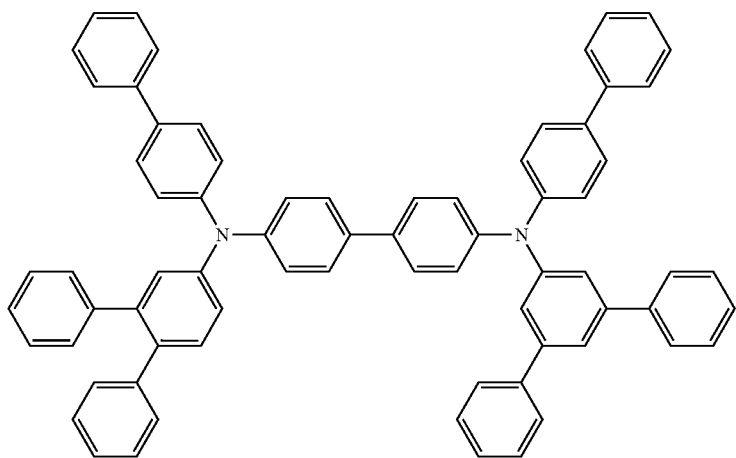
Specific Example 56
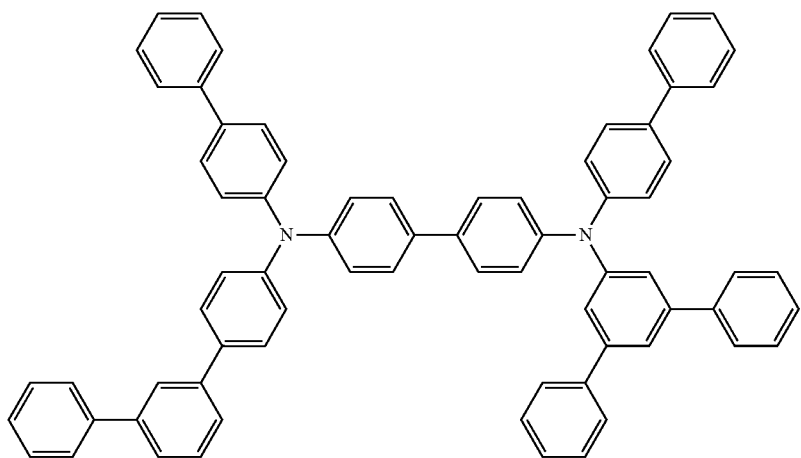
Specific Example 57
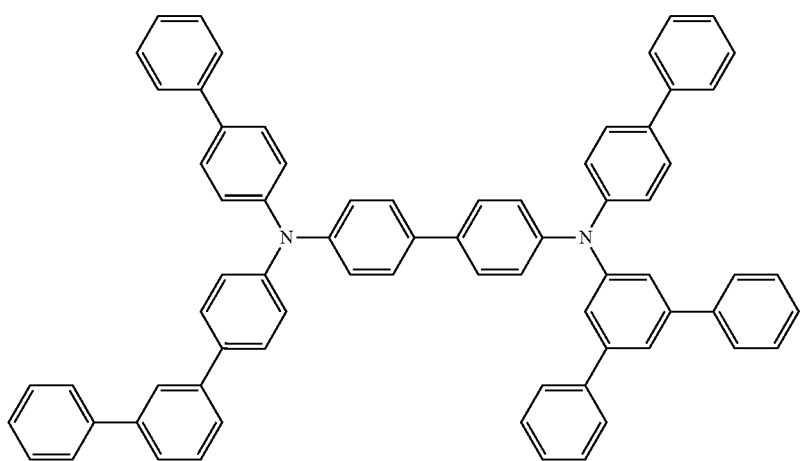

Specific Example 58
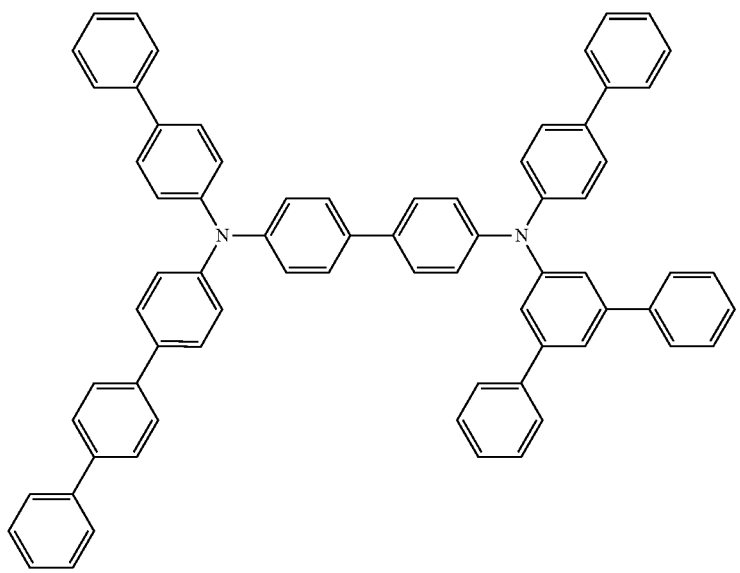
Specific Example 59
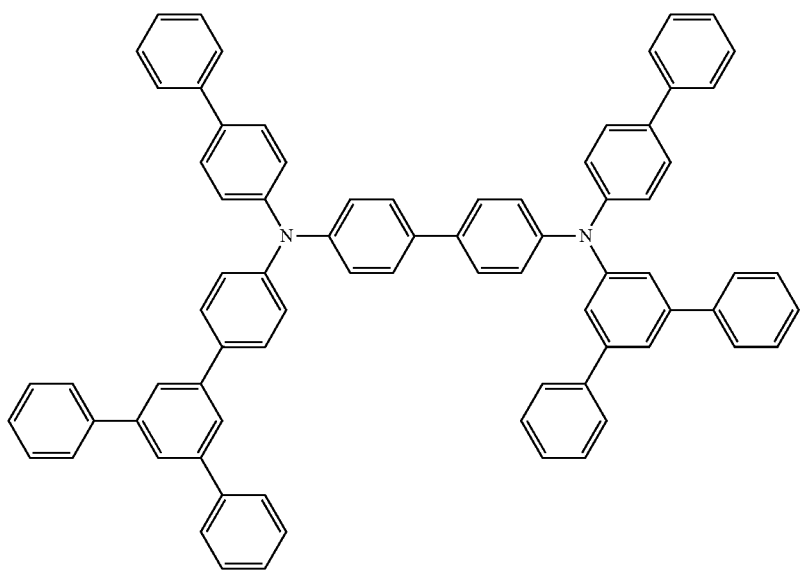
Specific Example 60
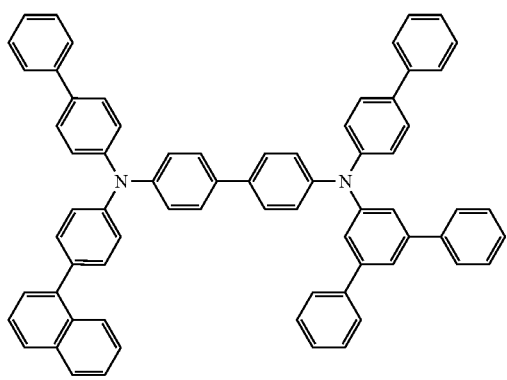
Specific Example 61
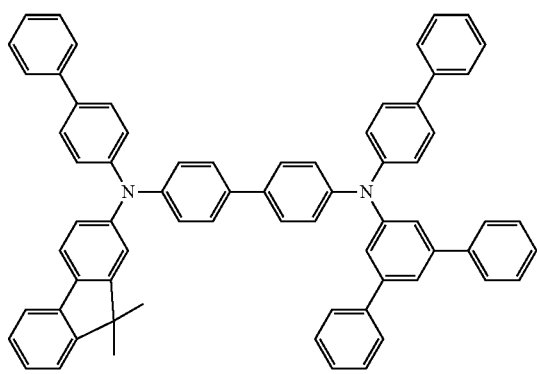

-continued
Specific Example 62
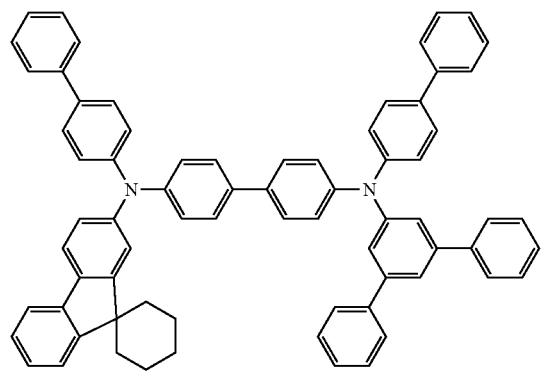
Specific Example 63
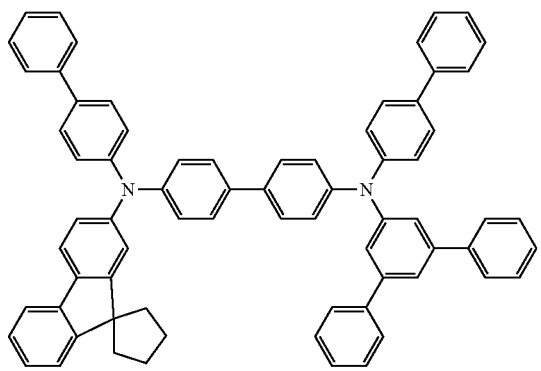
Specific Example 64
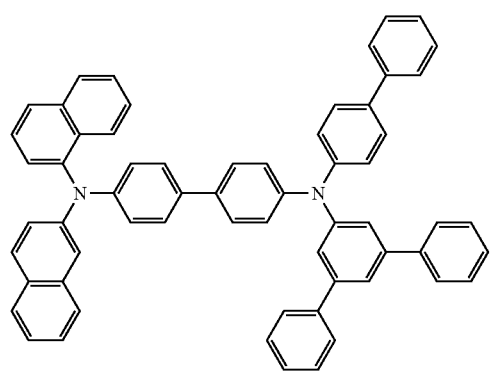
Specific Example 65
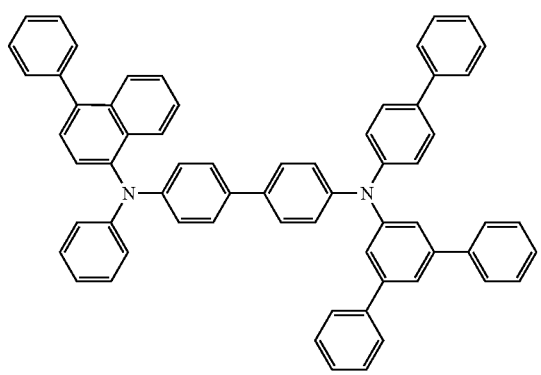
Specific Example 66
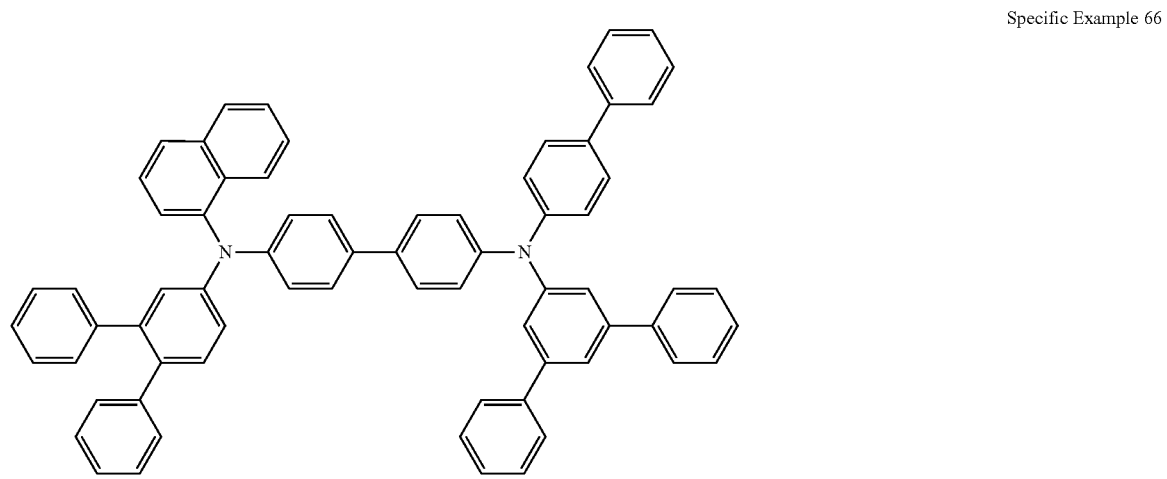

Specific Example 67
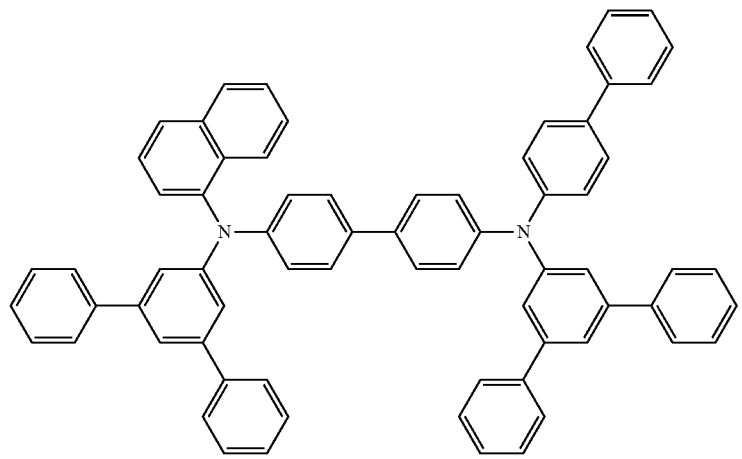
Specific Example 68
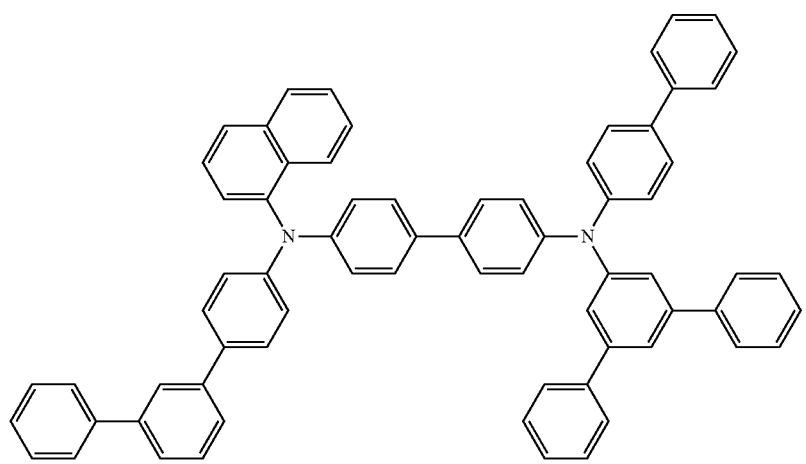
Specific Example 69
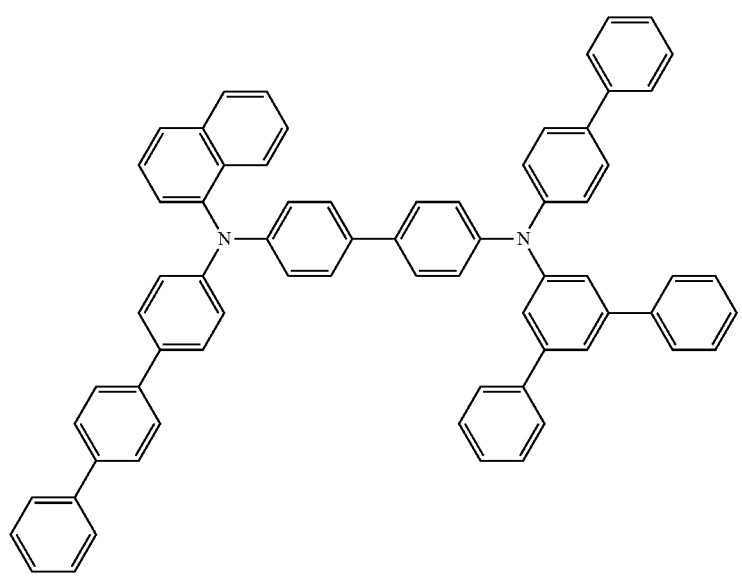

-continued
Specific Example 70
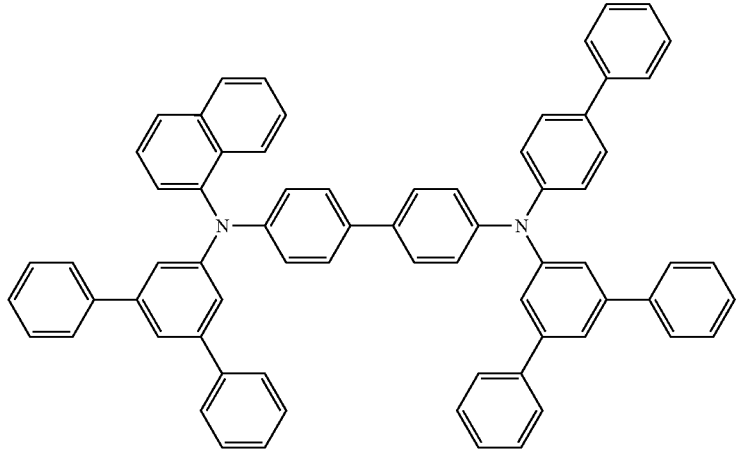
Specific Example 71
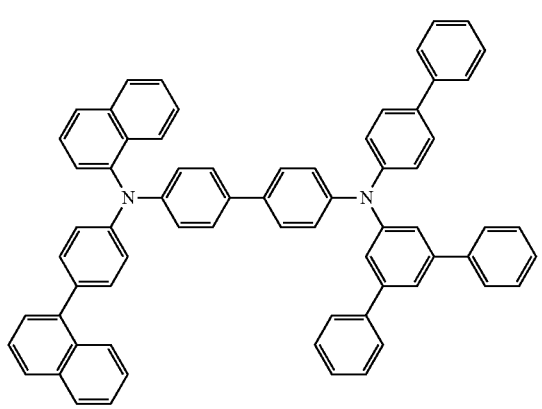
Specific Example 72
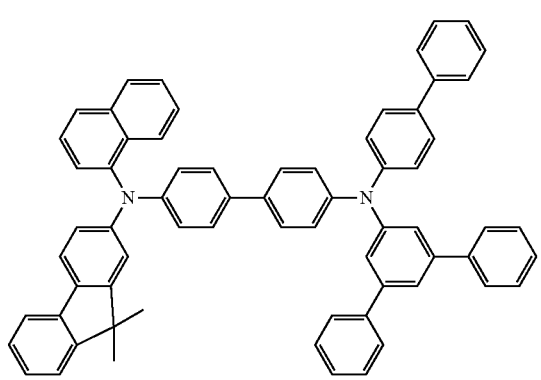
Specific Example 73
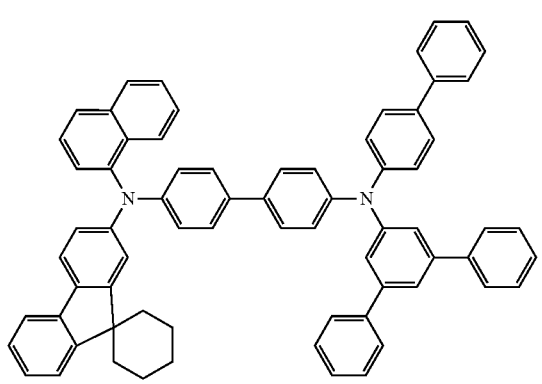
Specific Example 74
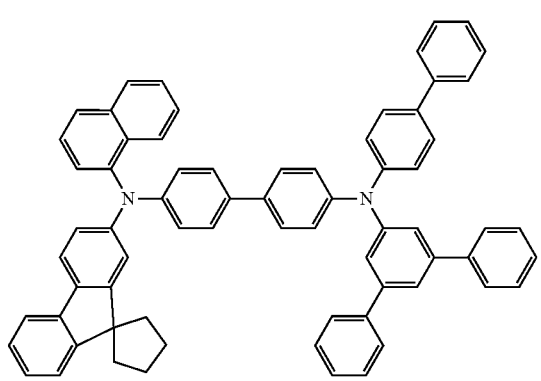
Specific Example 75
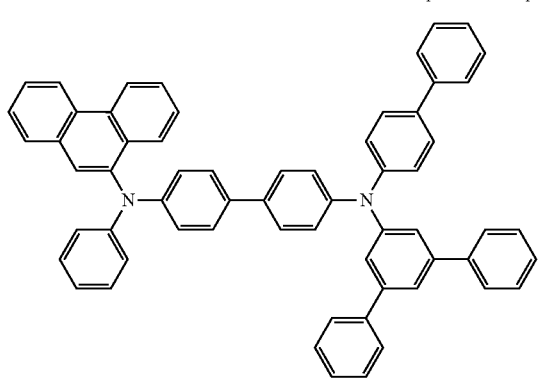
Specific Example 76
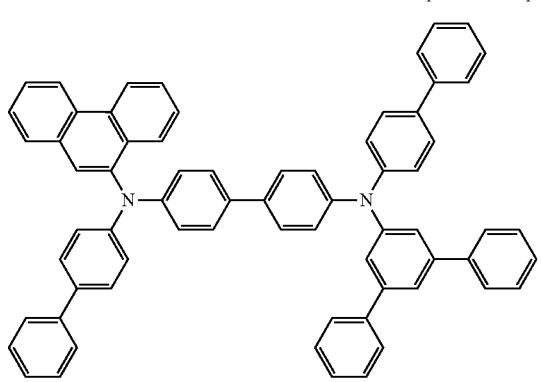

-continued
Specific Example 77
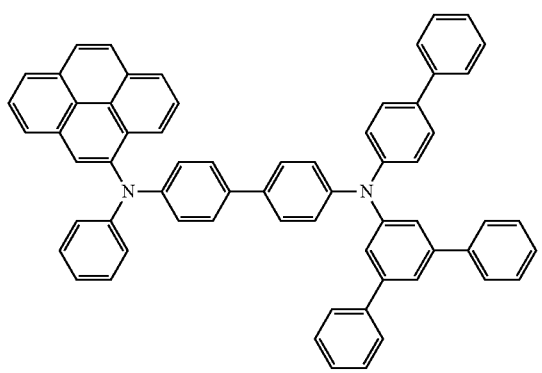
Specific Example 78
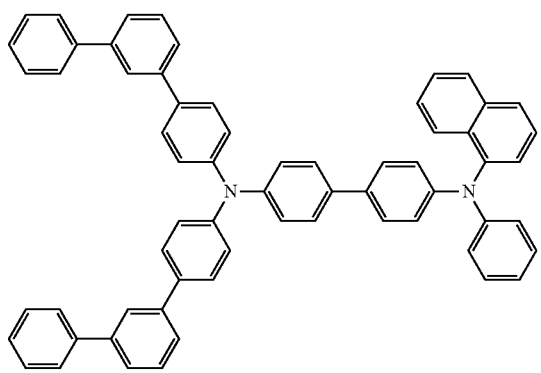
Specific Example 79
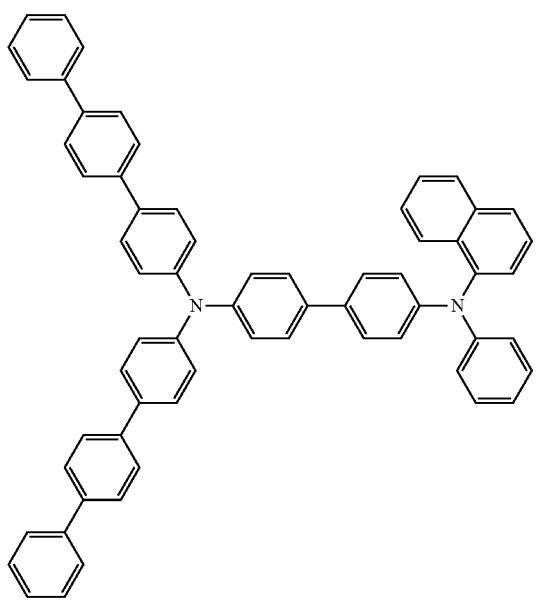
Specific Example 80
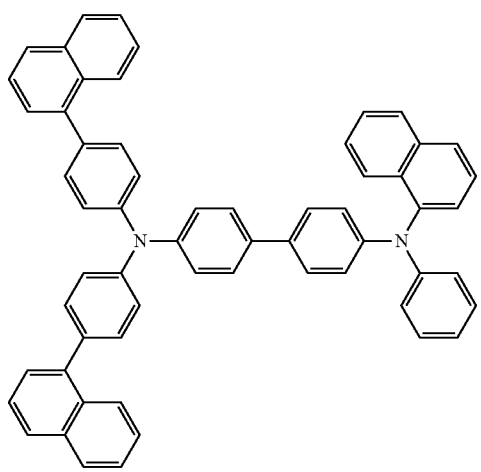
Specific Example 81
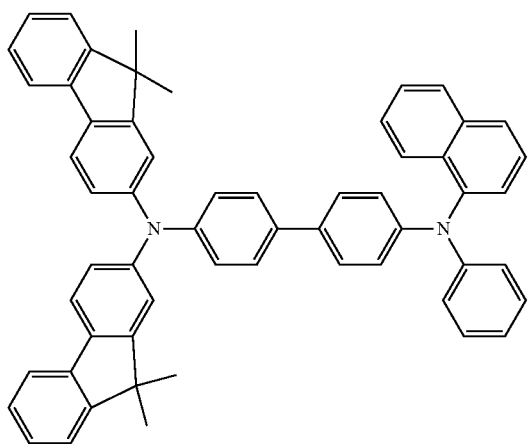
Specific Example 82
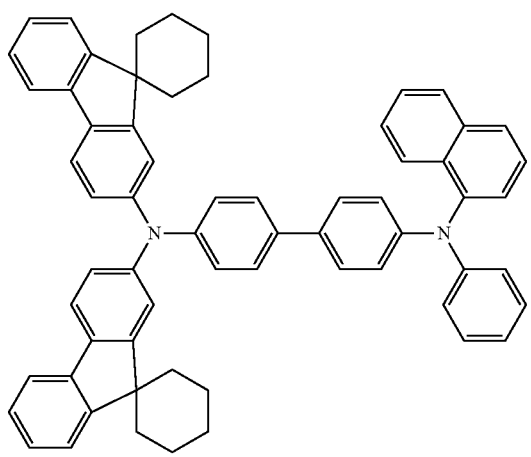

-continued
Specific Example 83
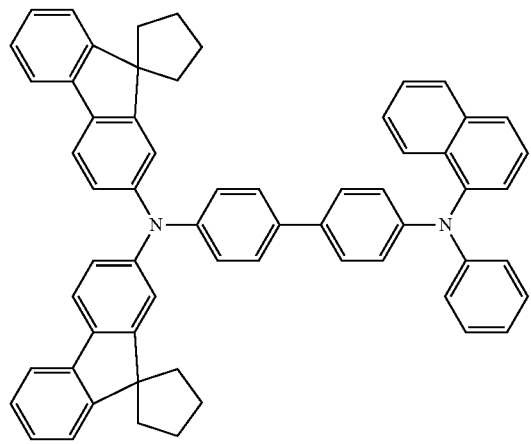
Specific Example 84
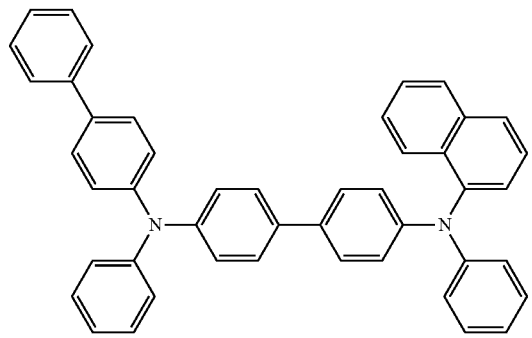
Specific Example 85
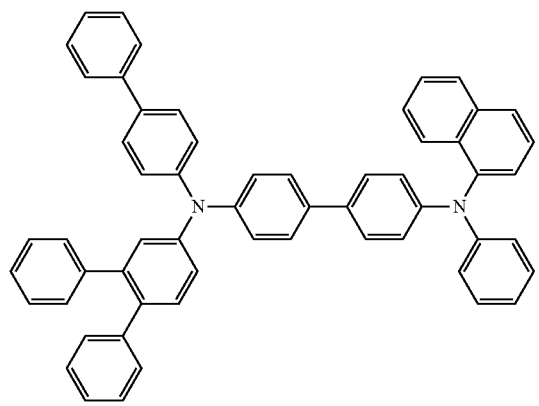
Specific Example 86
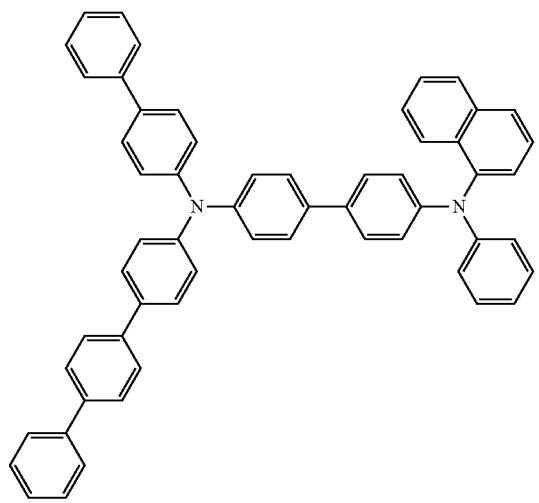
Specific Example 87
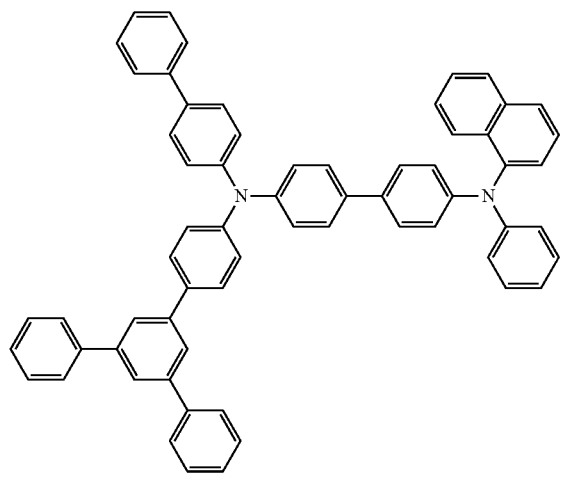
Specific Example 88
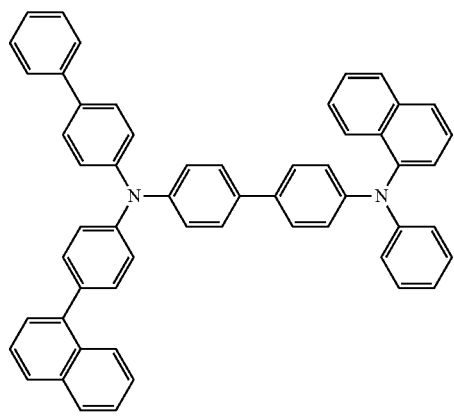

-continued
Specific Example 89
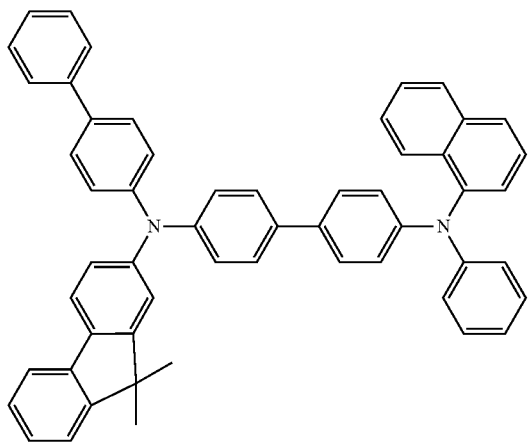
Specific Example 90
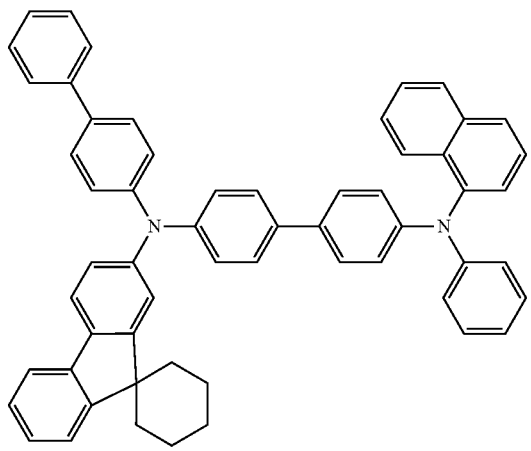
Specific Example 91
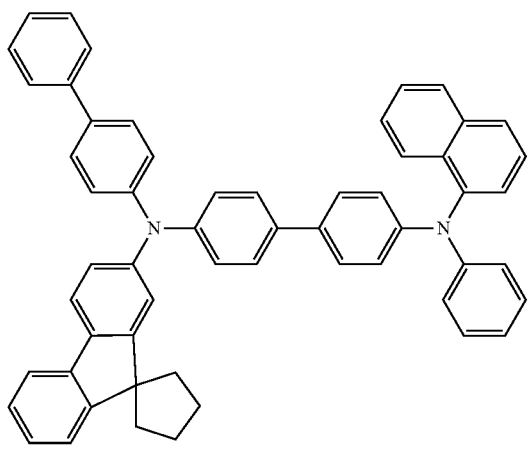
Specific Example 92
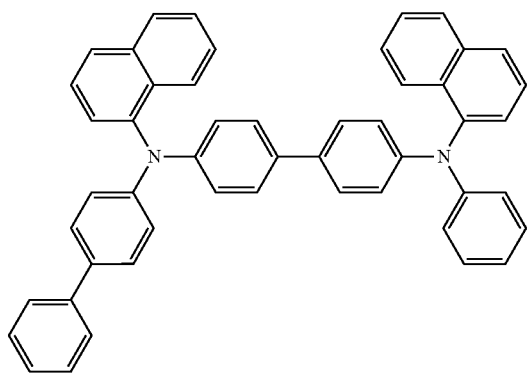
Specific Example 93
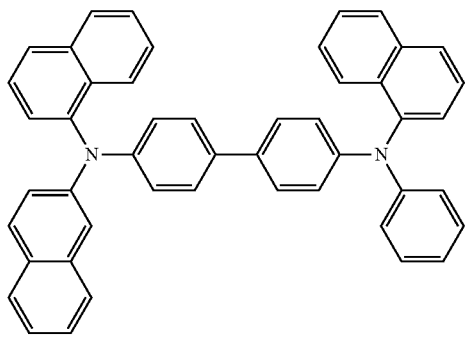
Specific Example 94
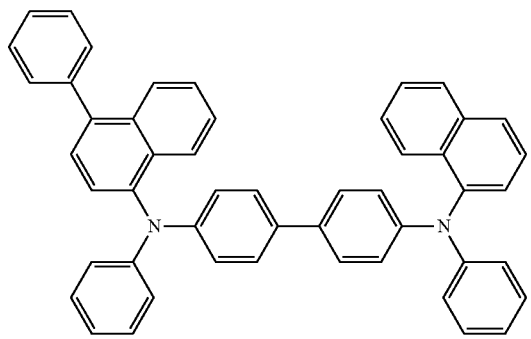

-continued
Specific Example 95
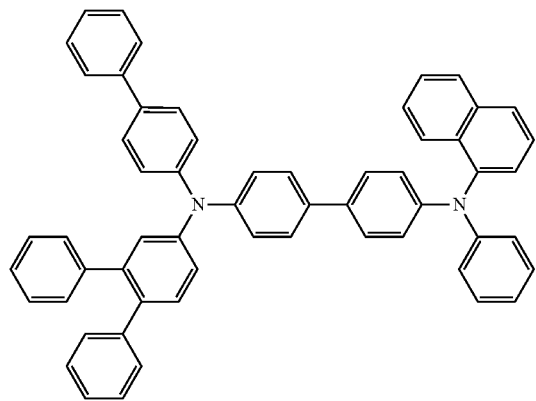
Specific Example 96
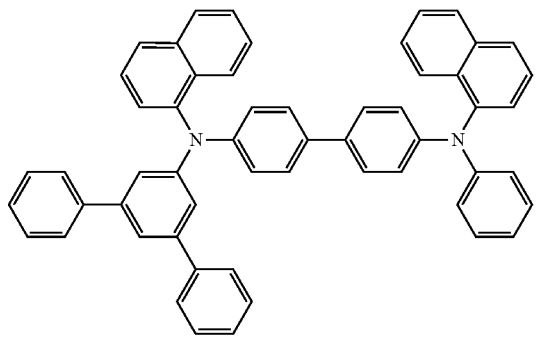
Specific Example 97
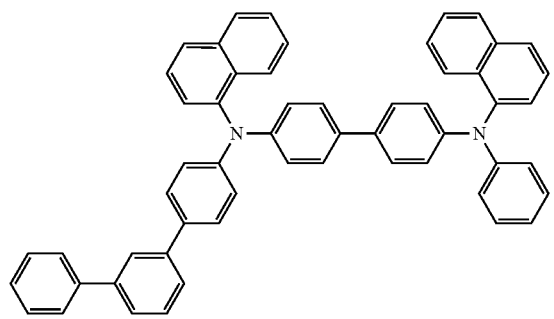
Specific Example 98
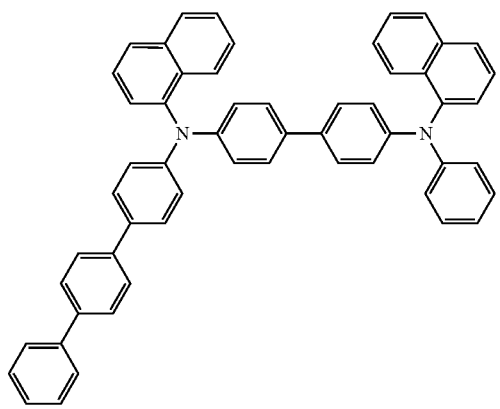
Specific Example 99
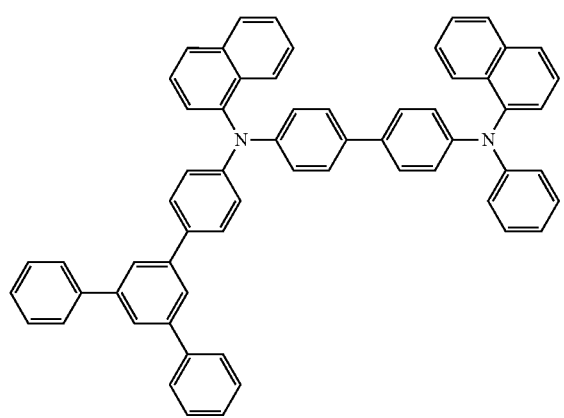
Specific Example 100
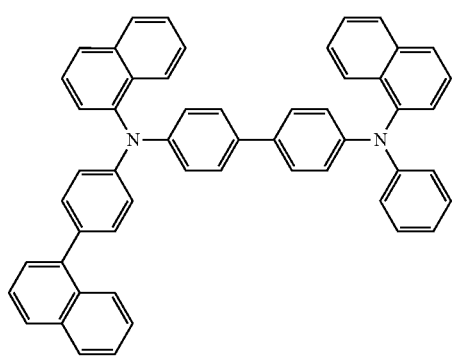

-continued
Specific Example 101
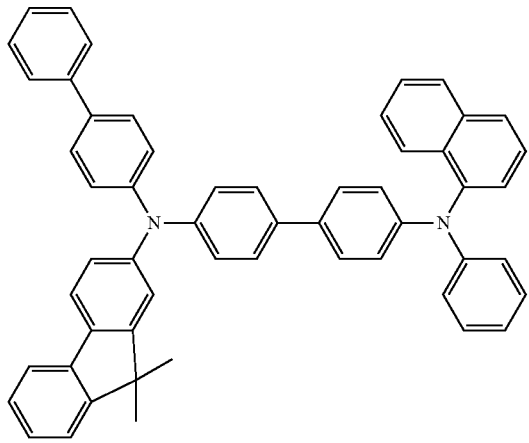
Specific Example 102
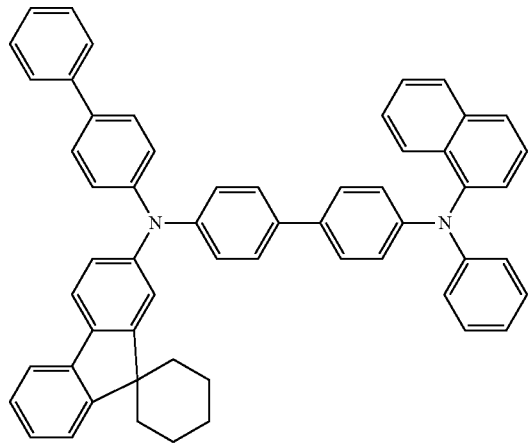
Specific Example 103
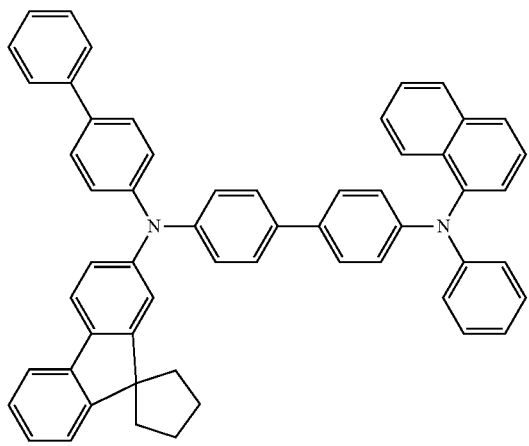
Specific Example 104
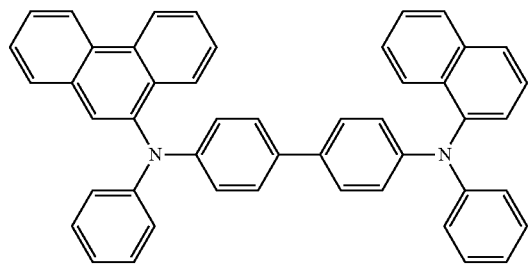
Specific Example 105
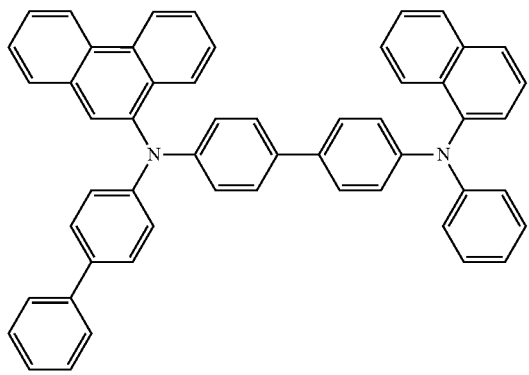
Specific Example 106
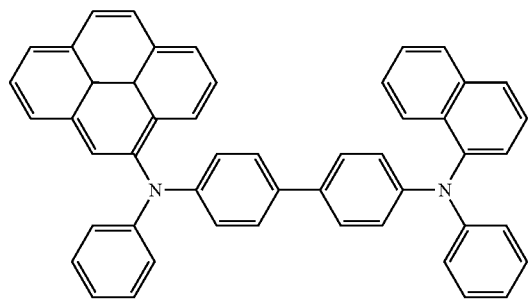

-continued
Specific Example 107
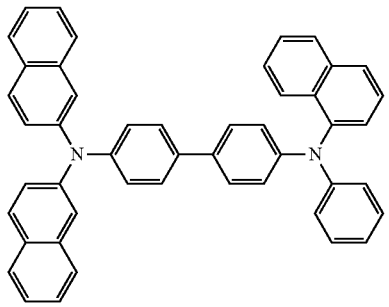
Specific Example 108
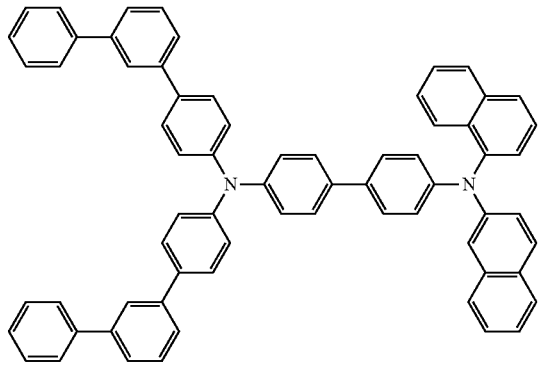
Specific Example 109
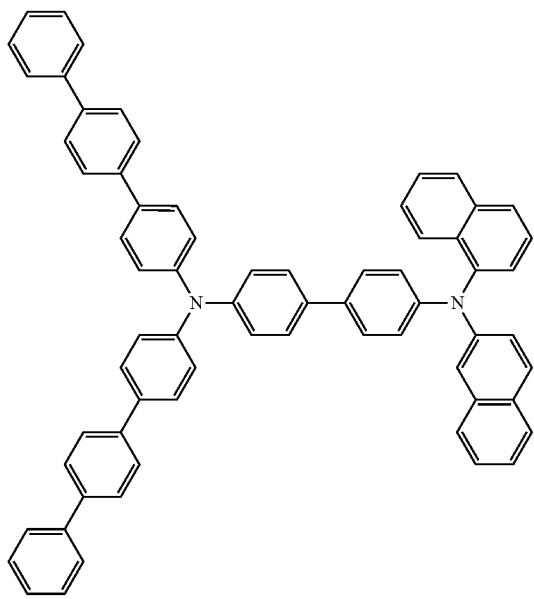
Specific Example 110
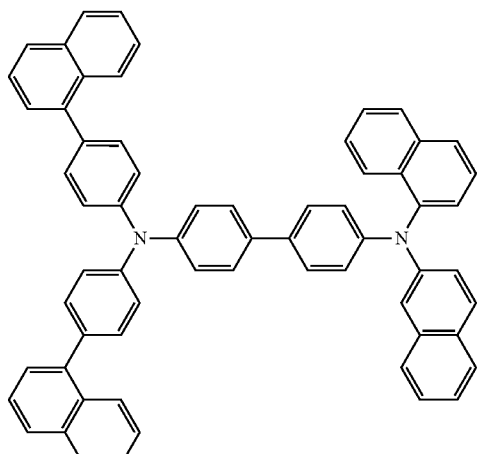
Specific Example 111
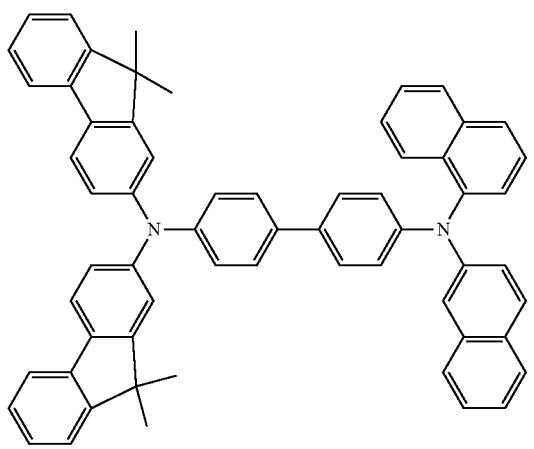
Specific Example 112
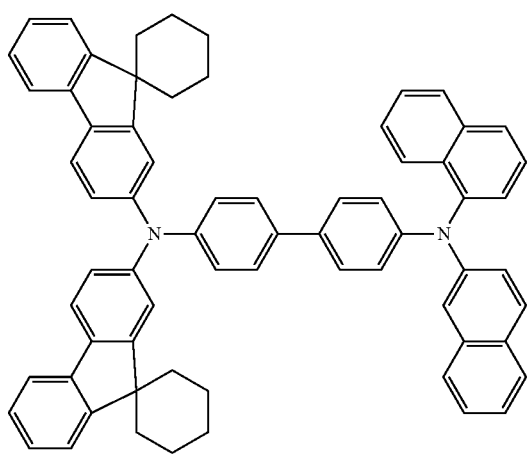

-continued
Specific Example 113
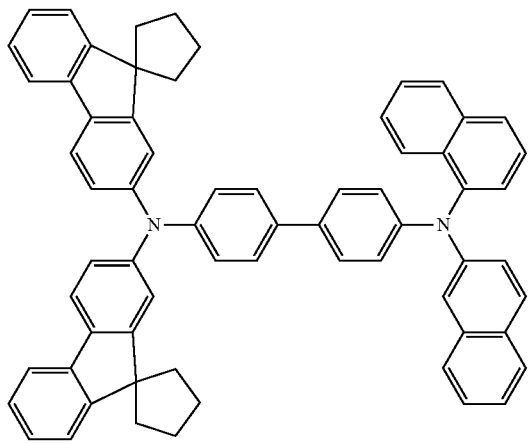
Specific Example 114
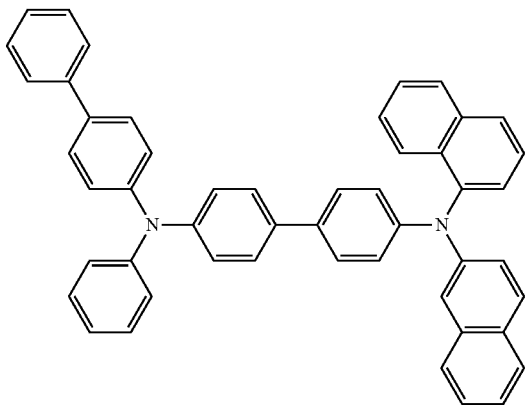
Specific Example 115
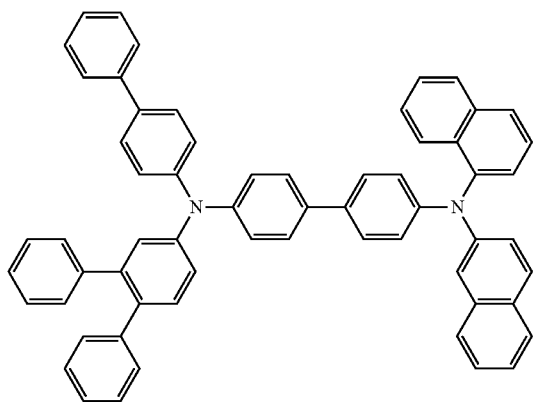
Specific Example 116
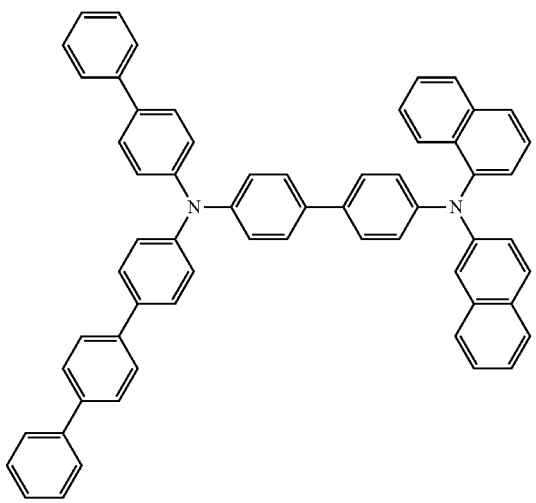
Specific Example 117
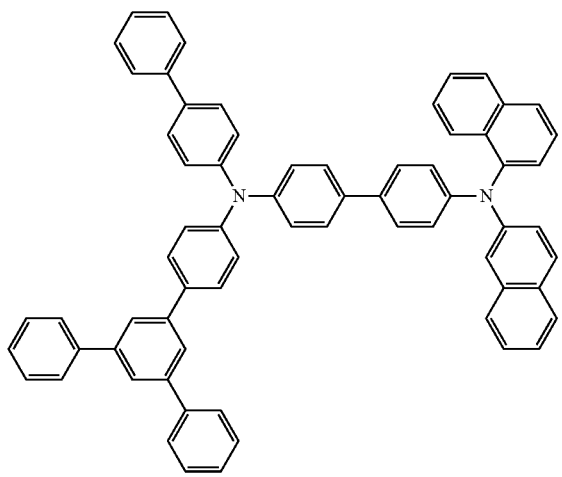
Specific Example 118
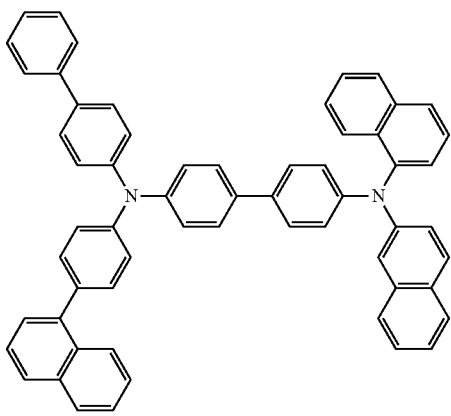

-continued
Specific Example 119
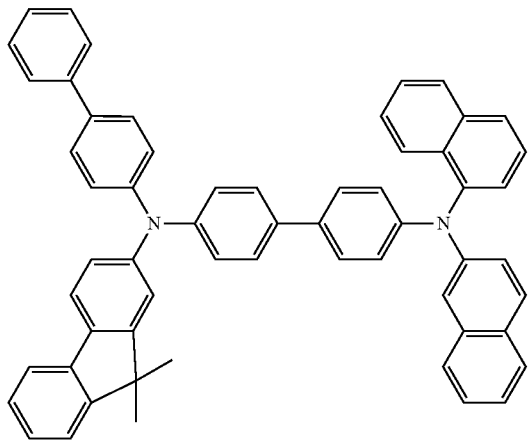
Specific Example 120
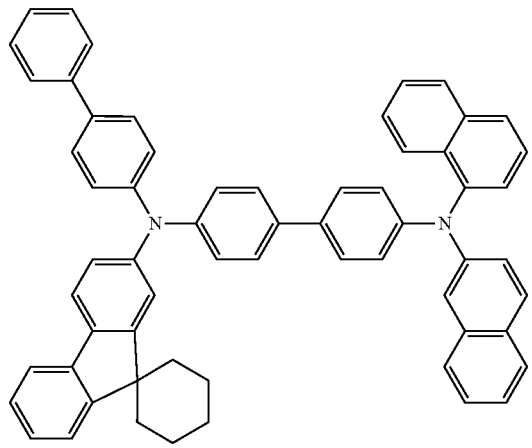
Specific Example 121
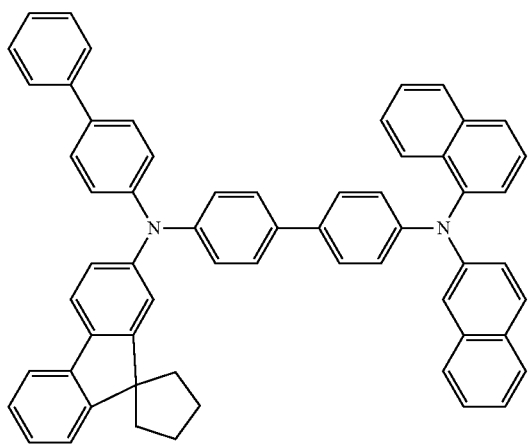
Specific Example 122
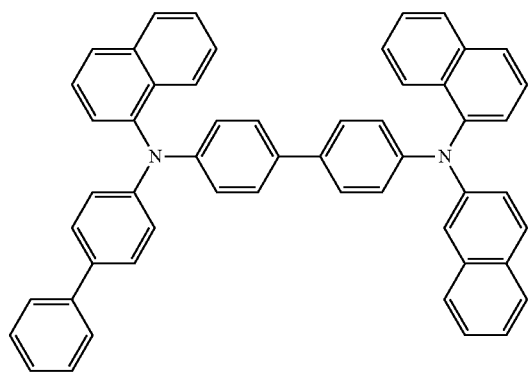
Specific Example 123
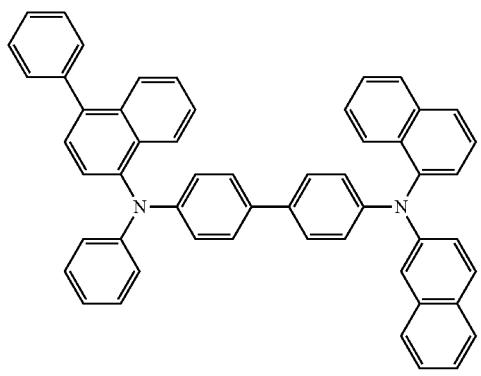
Specific Example 124
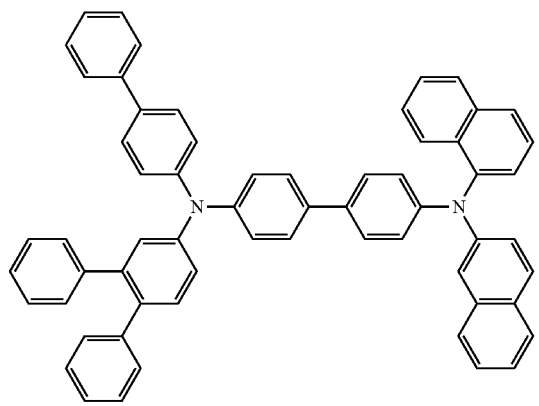

Specific Example 125
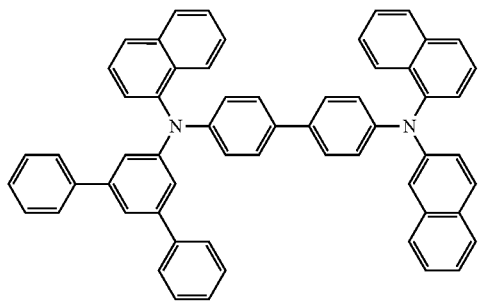
Specific Example 126
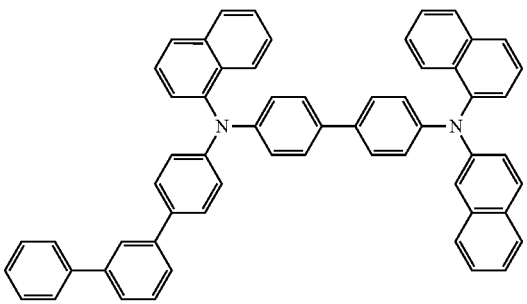
Specific Example 127
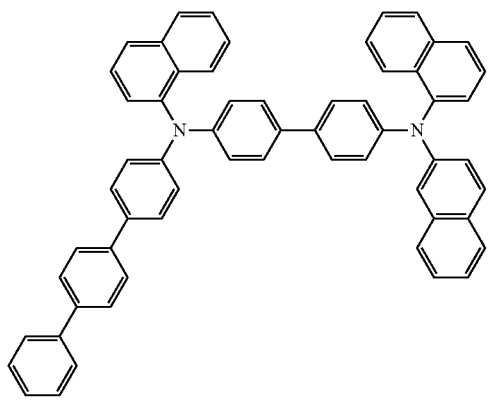
Specific Example 128
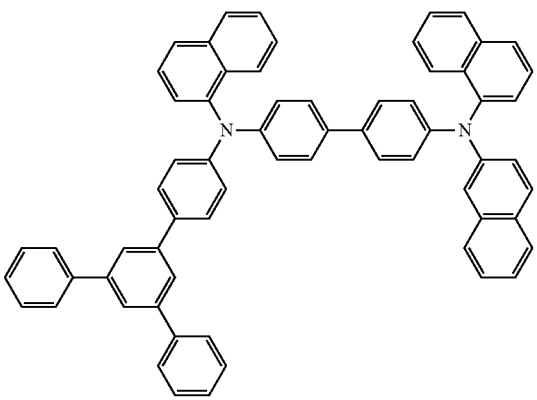
Specific Example 129
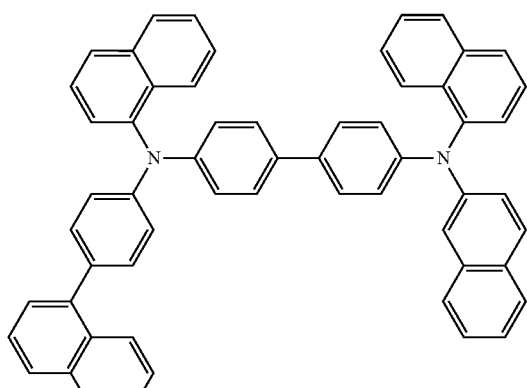
Specific Example 130
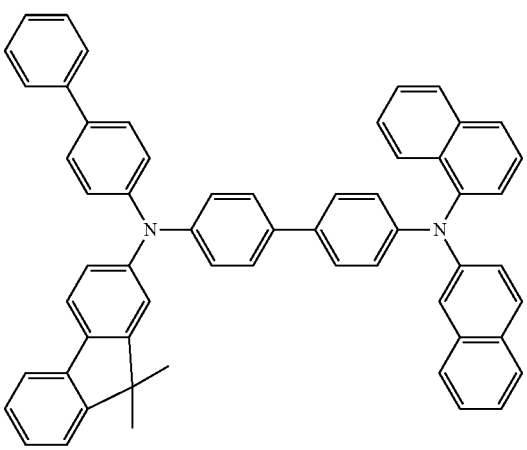

-continued
Specific Example 131
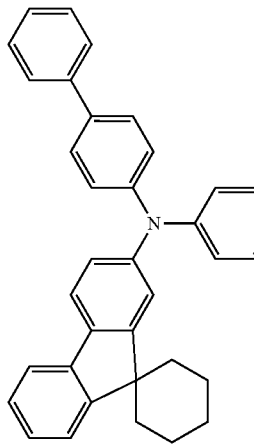
Specific Example 132
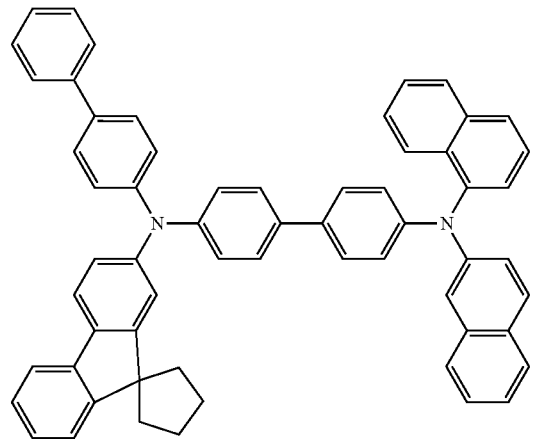
Specific Example 133
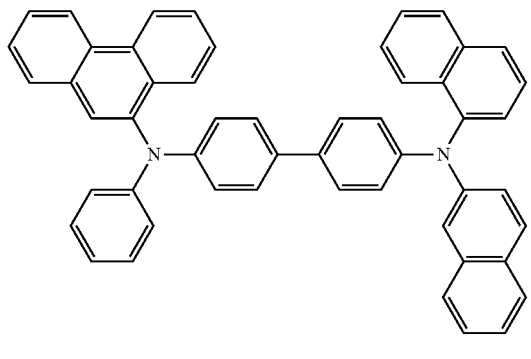
Specific Example 134
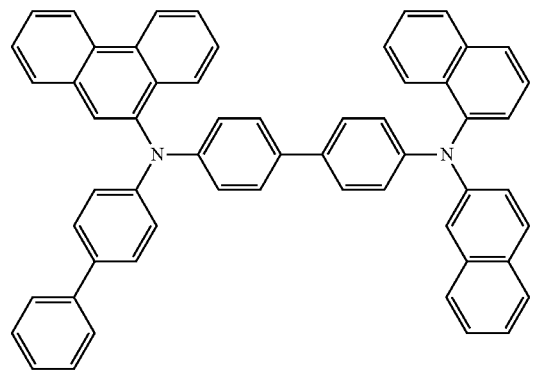
Specific Example 135
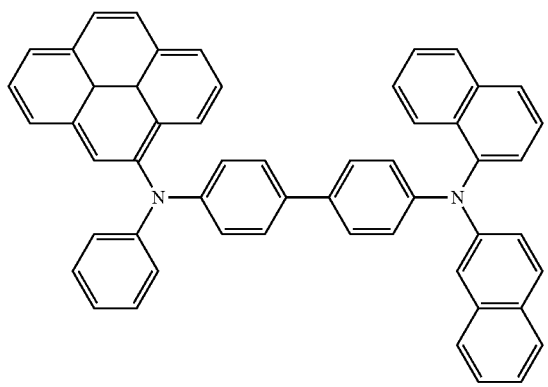
Specific Example 136
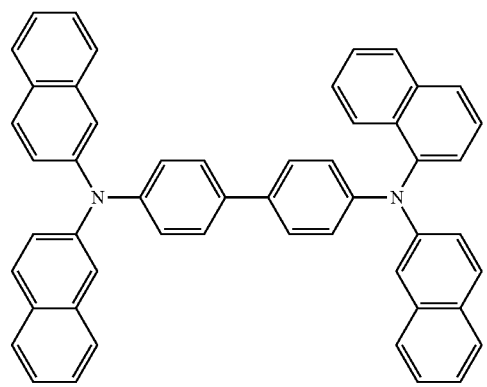

Specific Example 137
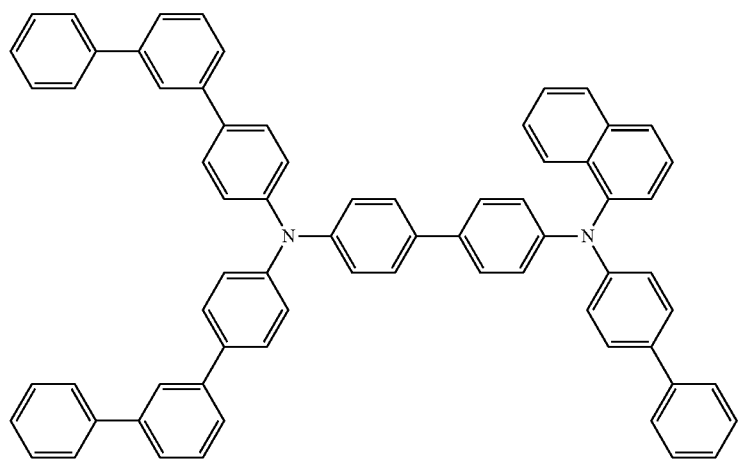
Specific Example 138
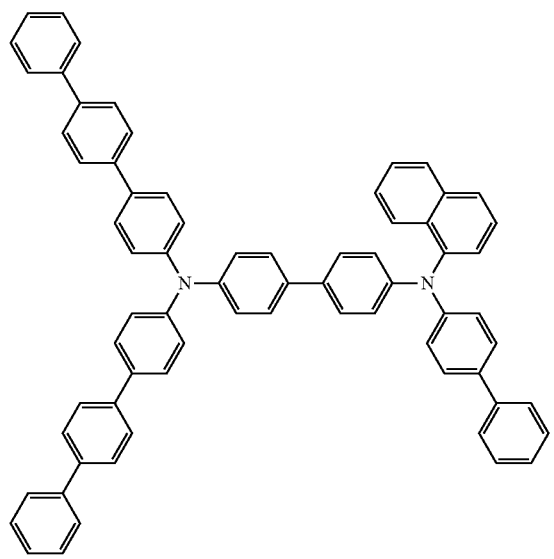
Specific Example 139
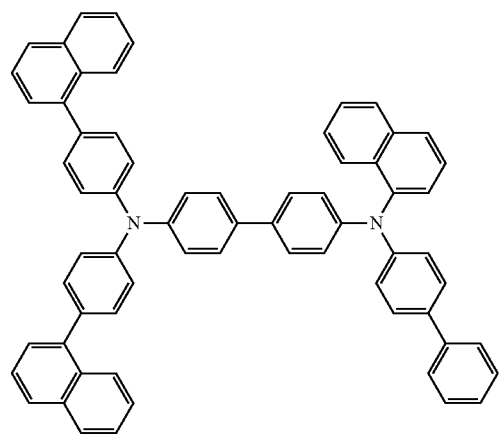
Specific Example 140
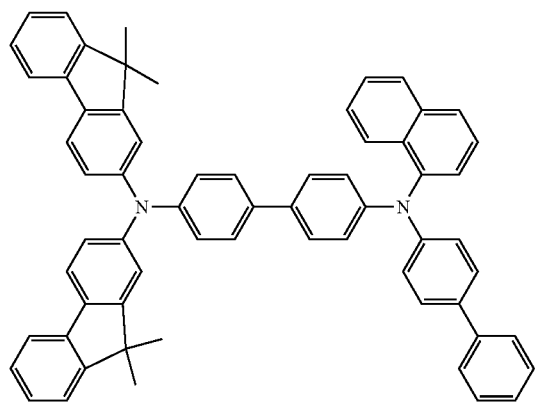
Specific Example 141
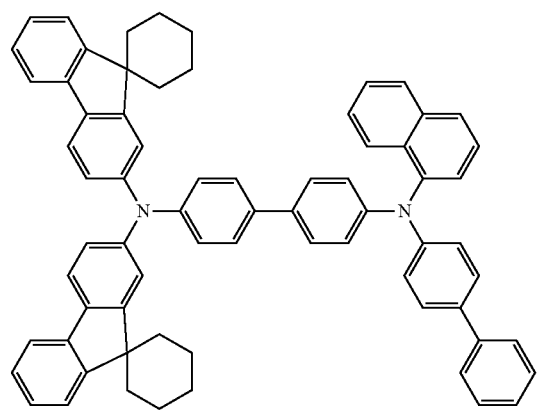

-continued
Specific Example 142
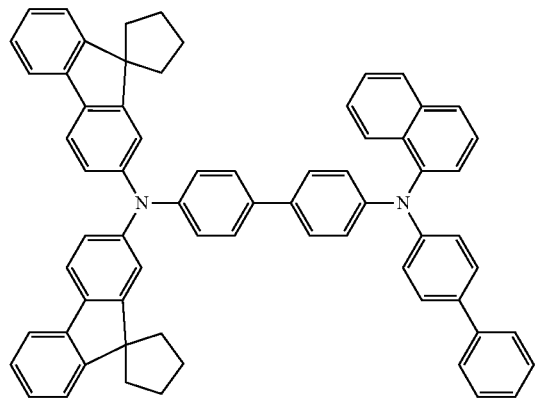
Specific Example 143
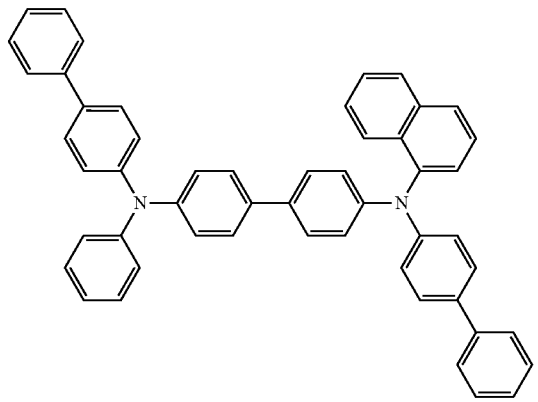
Specific Example 144
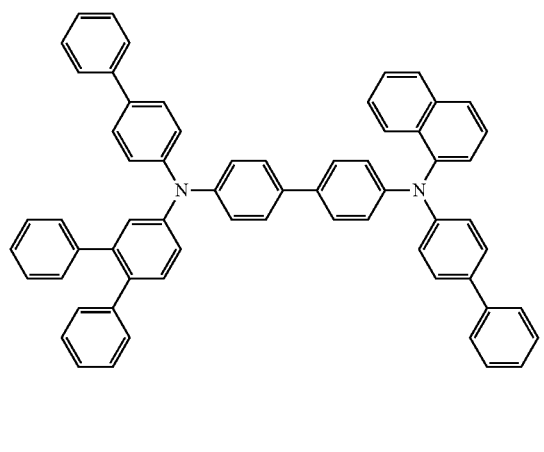
Specific Example 145
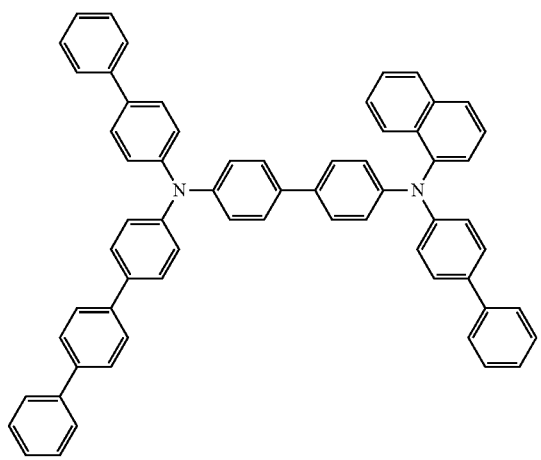
Specific Example 146
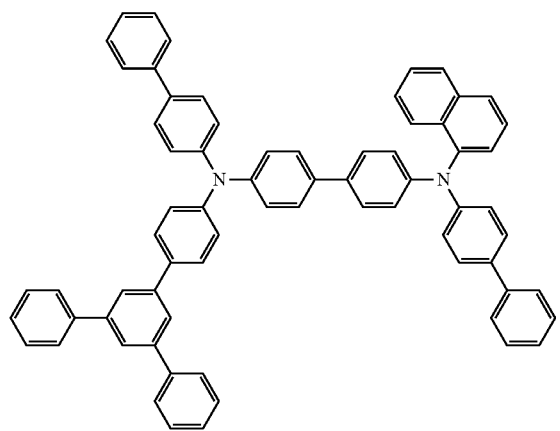
Specific Example 147
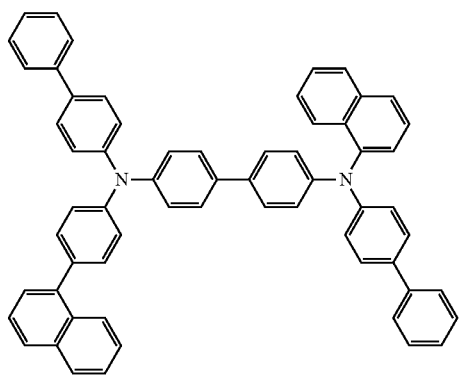

-continued
Specific Example 148
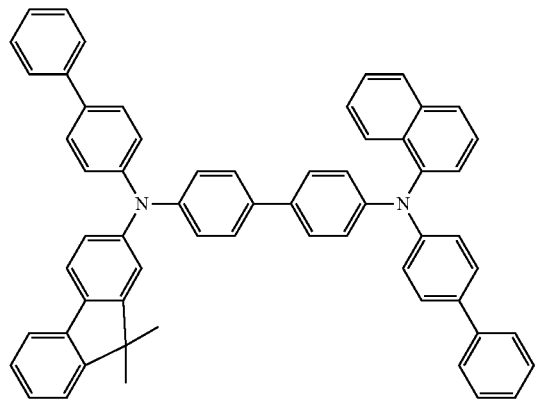
Specific Example 149
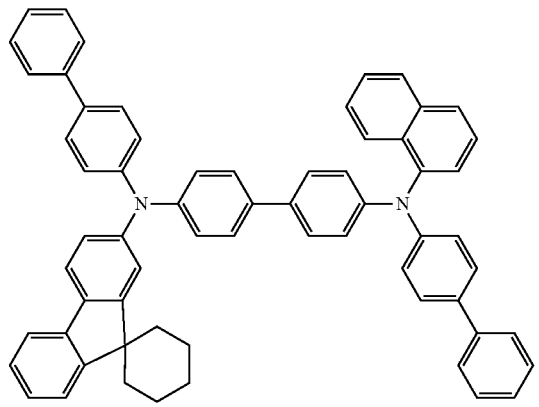
Specific Example 150
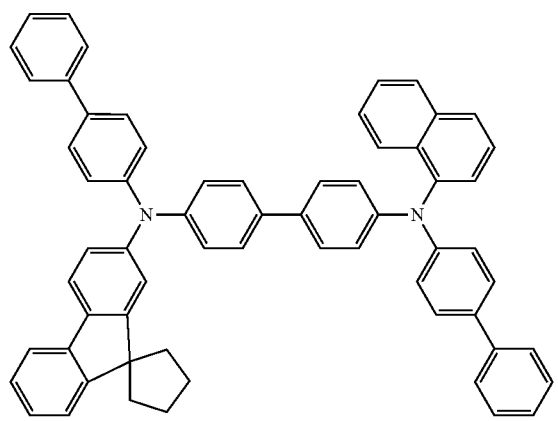
Specific Example 151
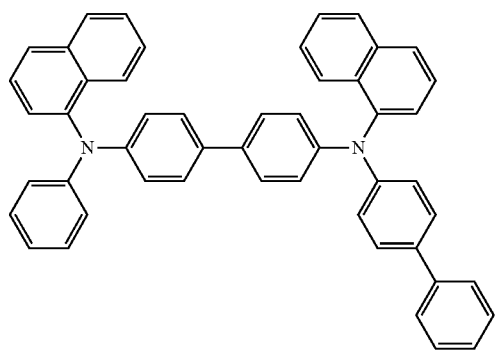
Specific Example 152
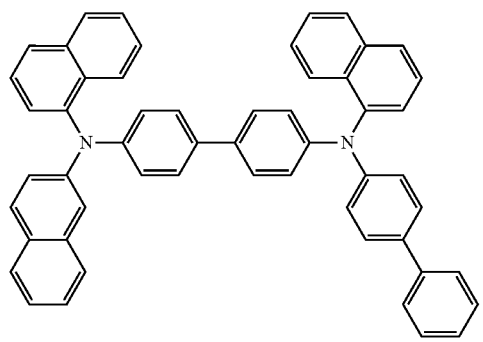
Specific Example 153
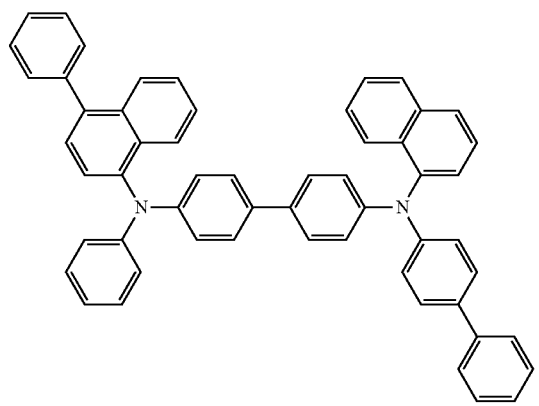

Specific Example 154
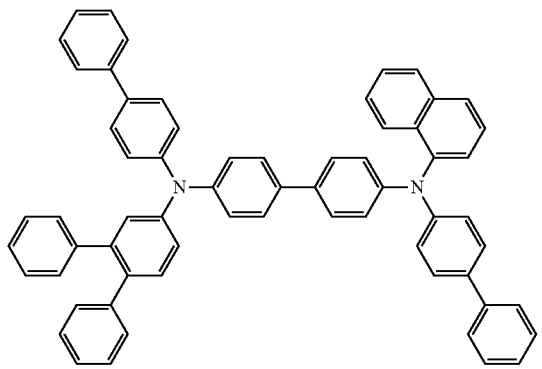
Specific Example 155
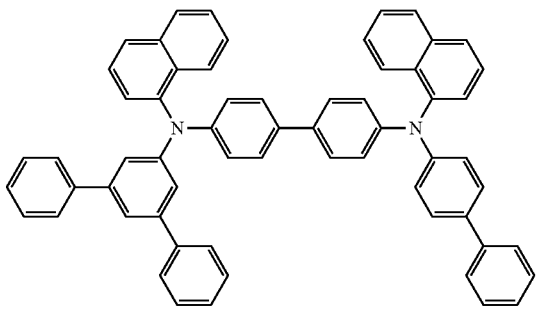
Specific Example 156
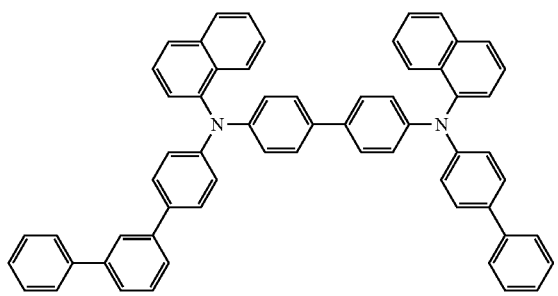
Specific Example 157
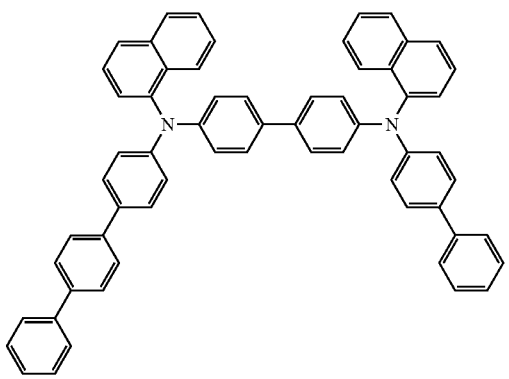
Specific Example 158
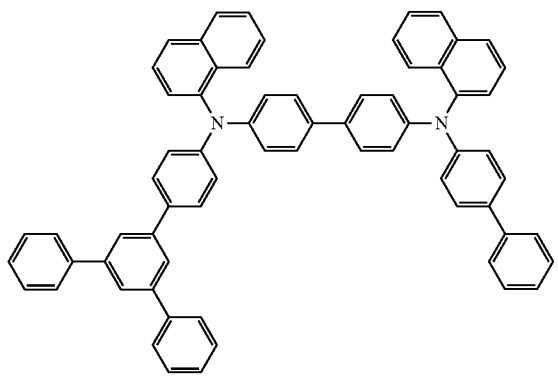
Specific Example 159
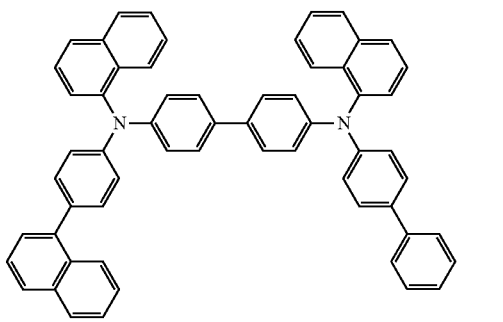
Specific Example 160
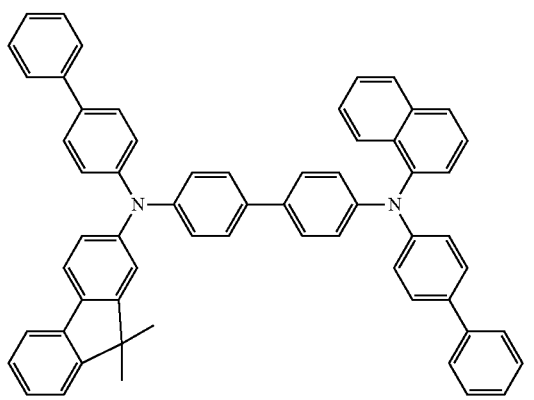
Specific Example 161
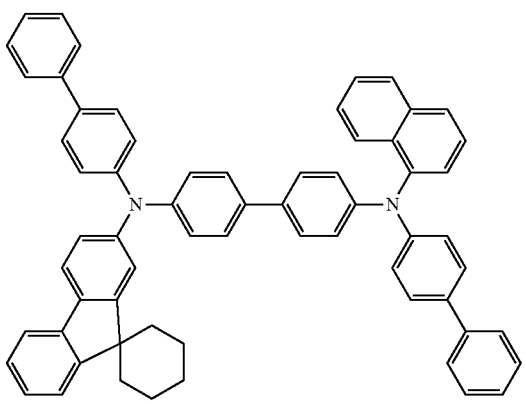

-continued
Specific Example 162
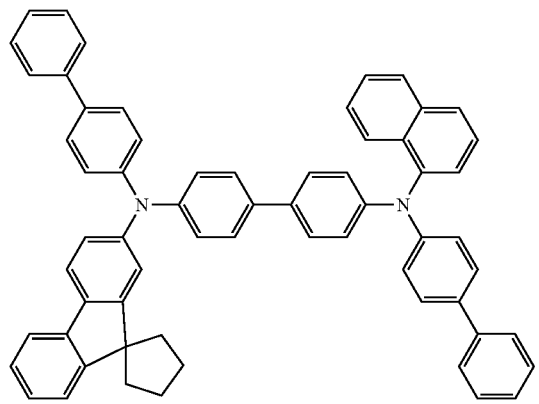
Specific Example 163
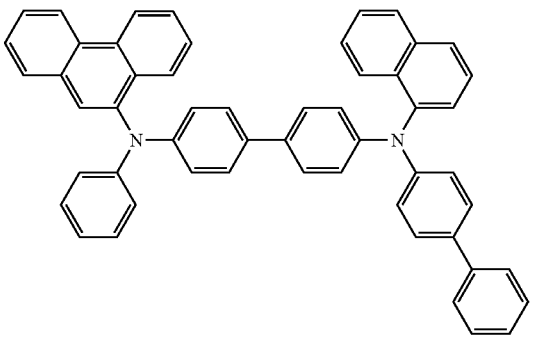
Specific Example 164
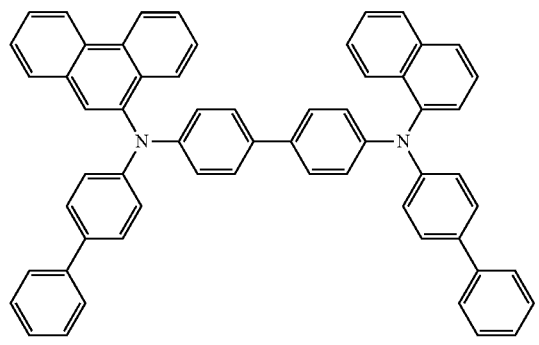
Specific Example 165
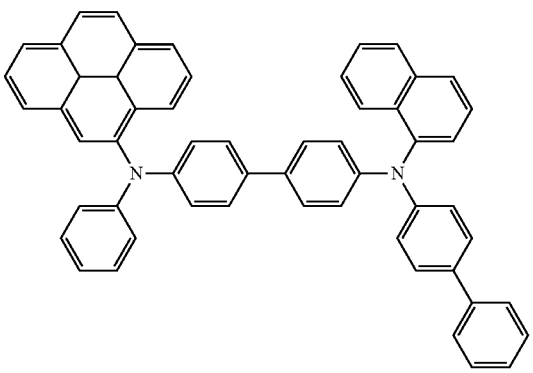
Specific Example 166
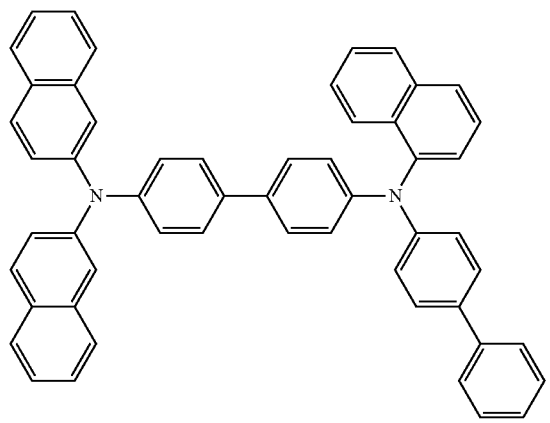

-continued
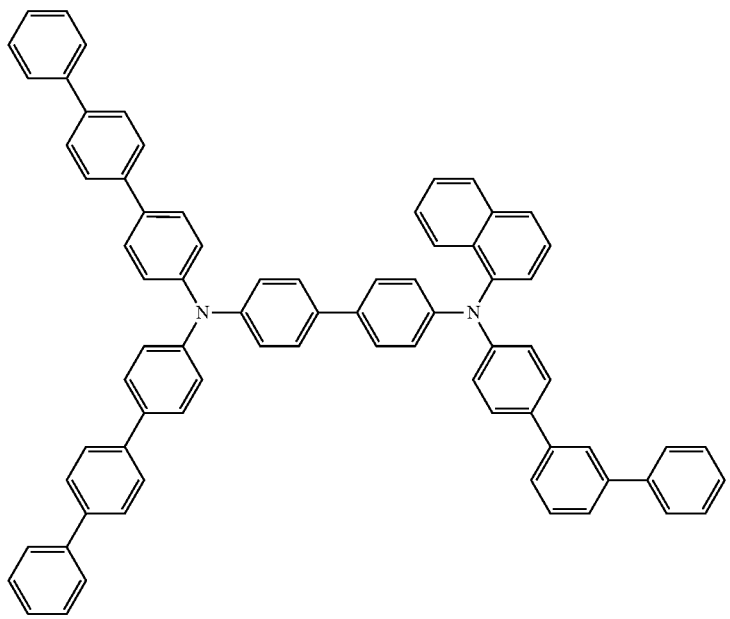
Specific Example 167
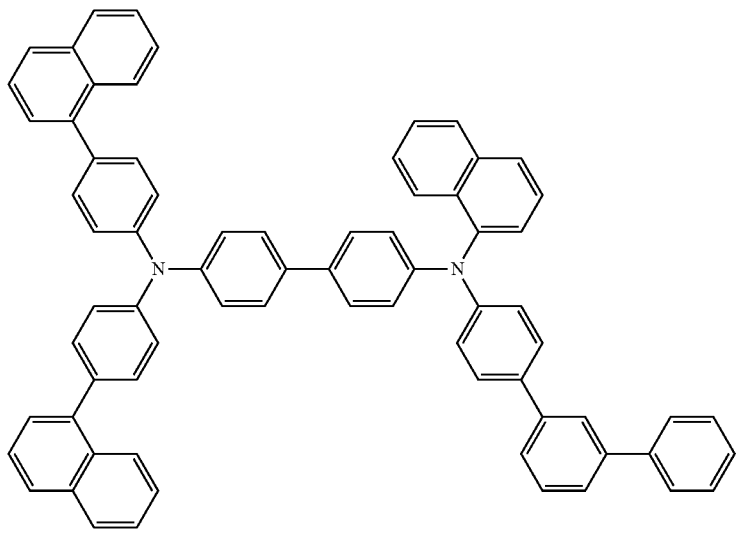
Specific Example 168
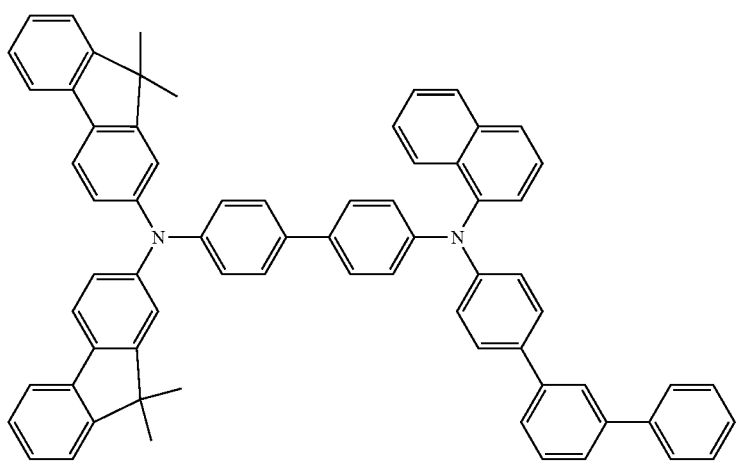
Specific Example 169

Specific Example 170
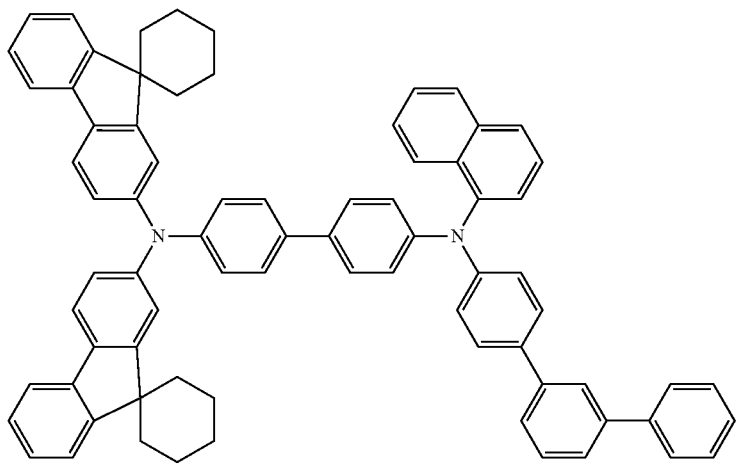
Specific Example 171
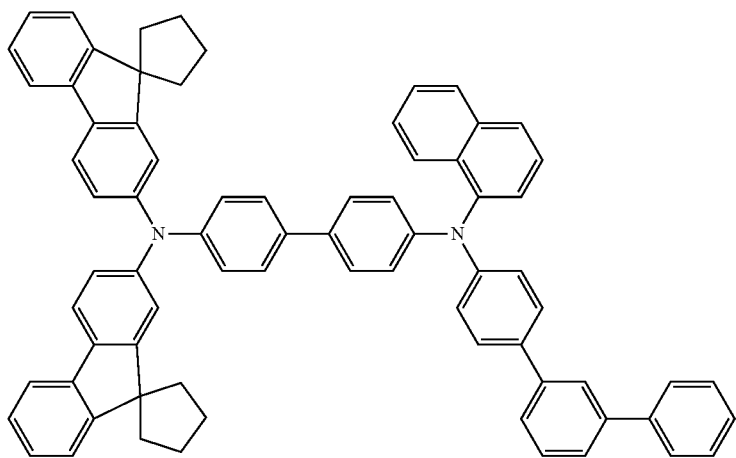
Specific Example 172
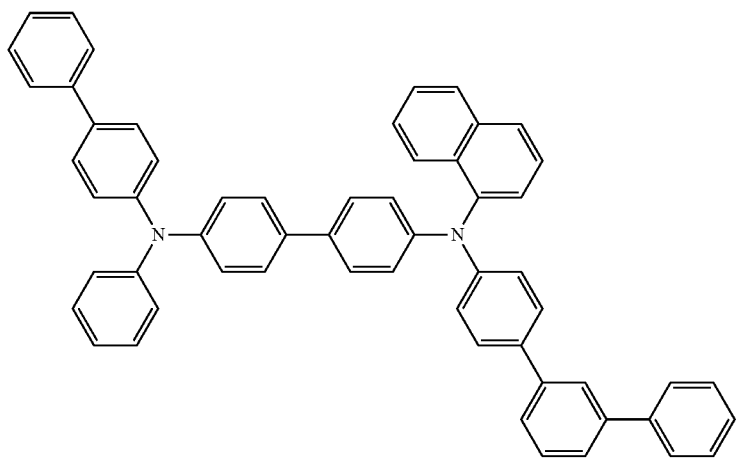

Specific Example 173
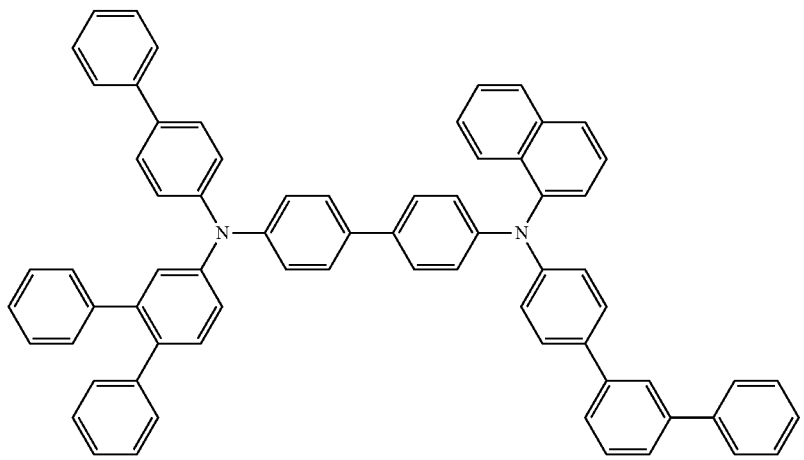
Specific Example 174
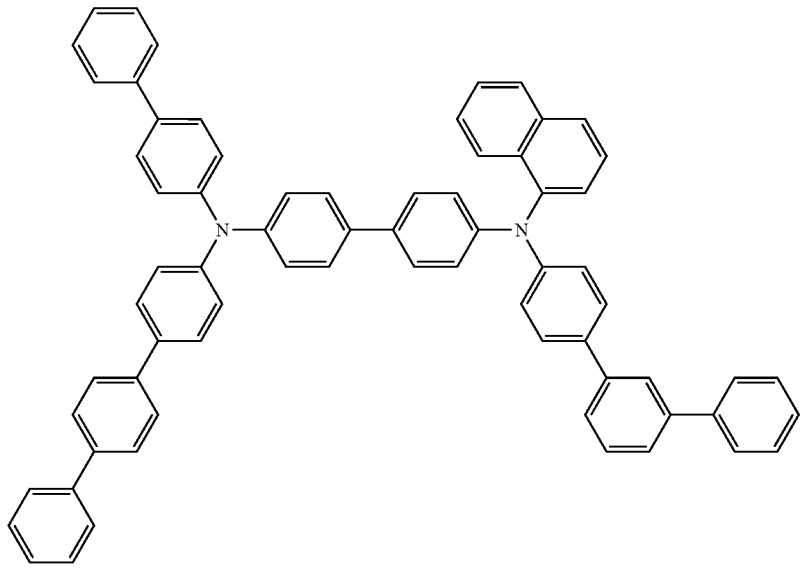
Specific Example 175
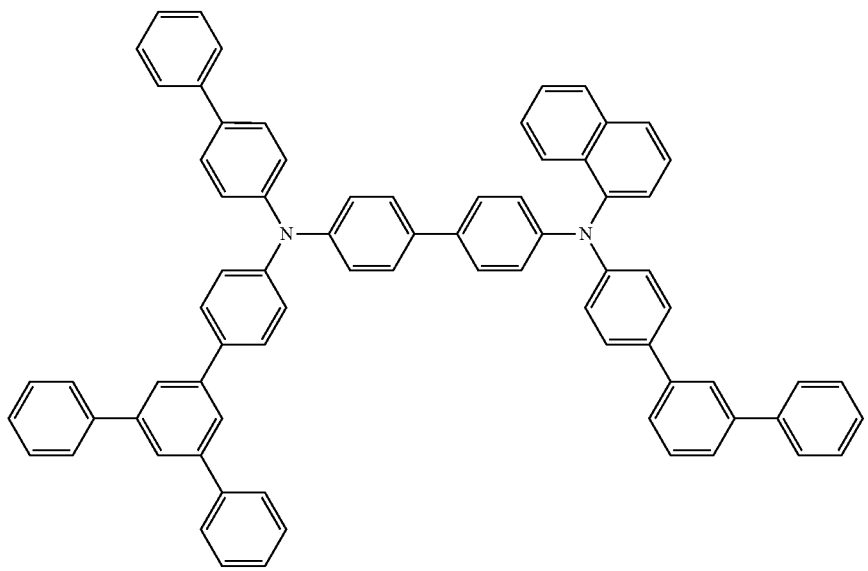

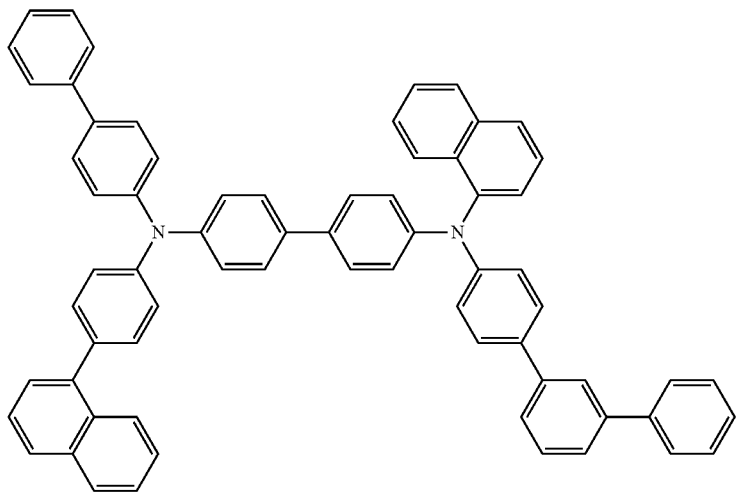
Specific Example 176
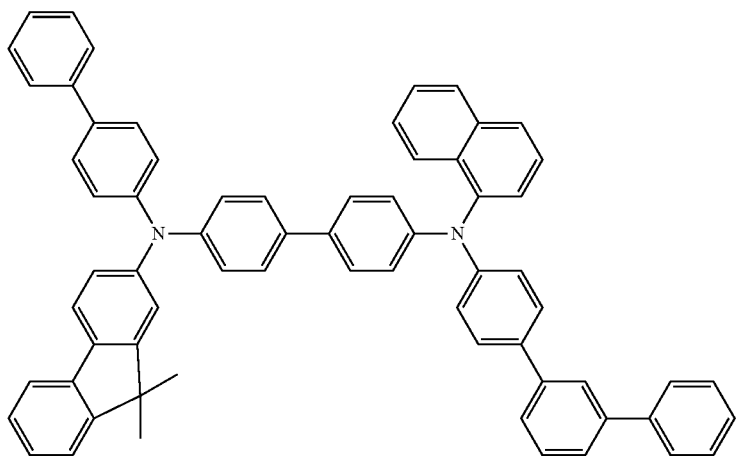
Specific Example 177
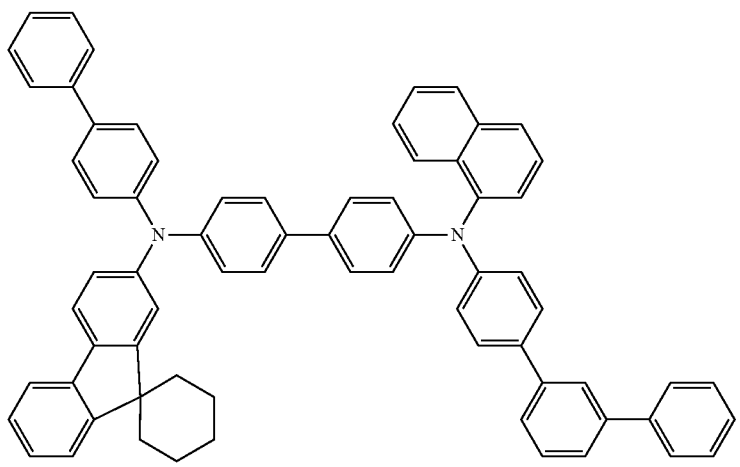
Specific Example 178

-continued
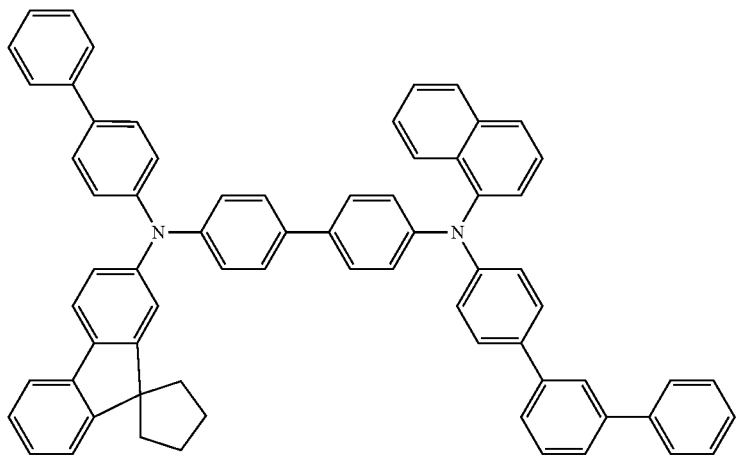
Specific Example 179
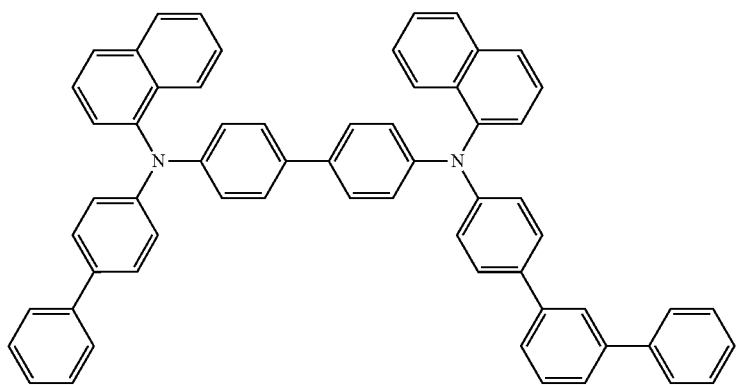
Specific Example 180
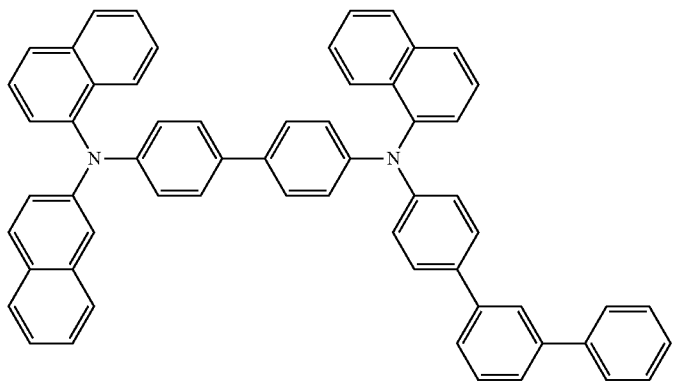
Specific Example 181

Specific Example 182
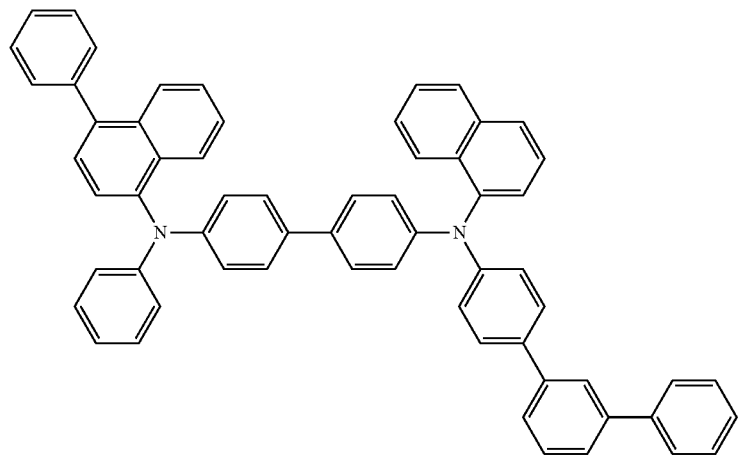
Specific Example 183
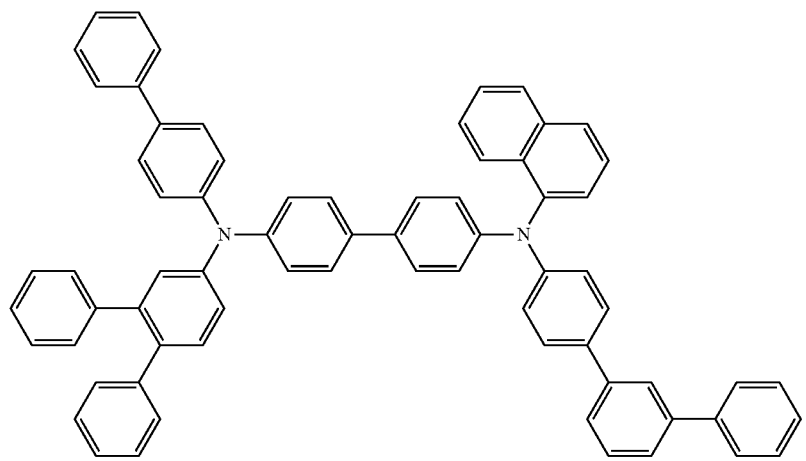
Specific Example 184
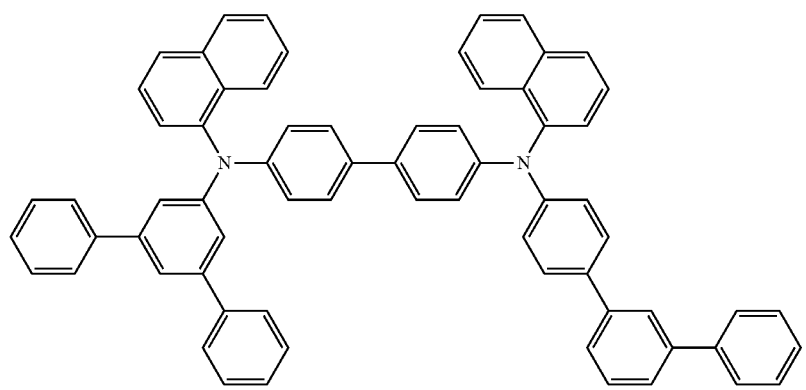

-continued
Specific Example 185
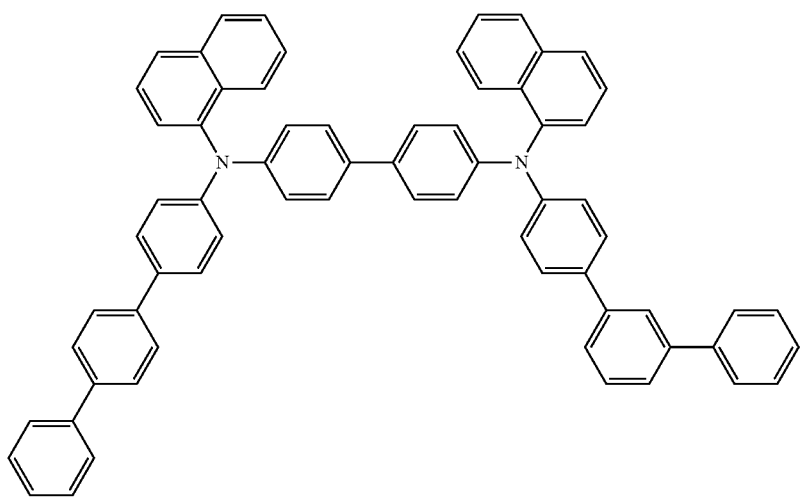
Specific Example 186
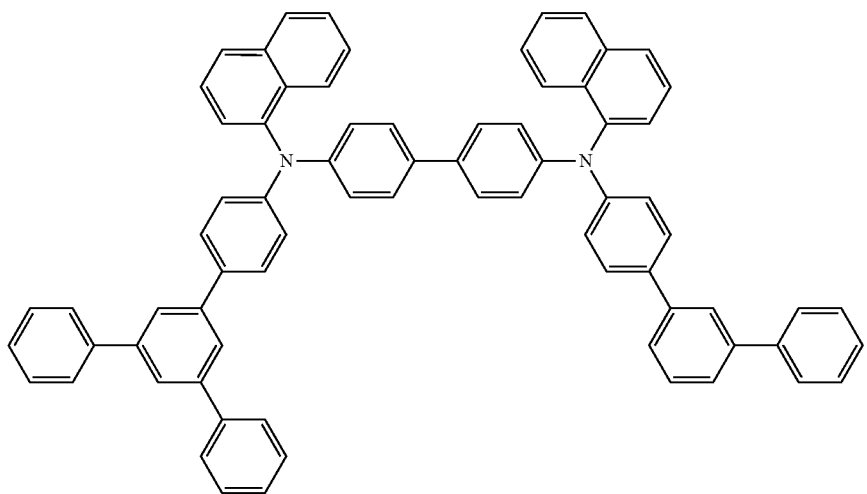
Specific Example 187
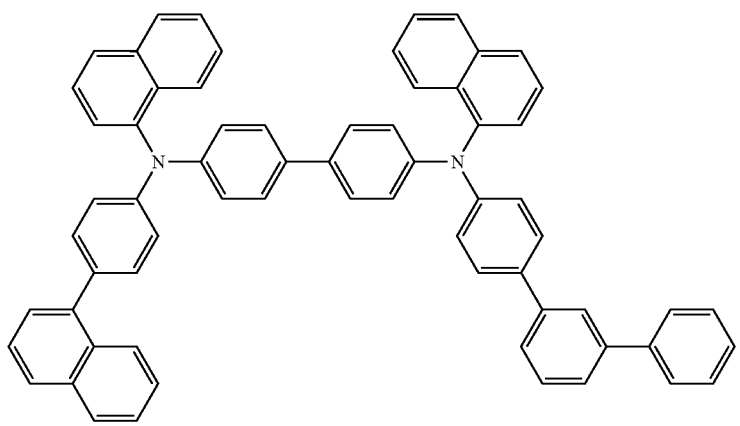

Specific Example 188
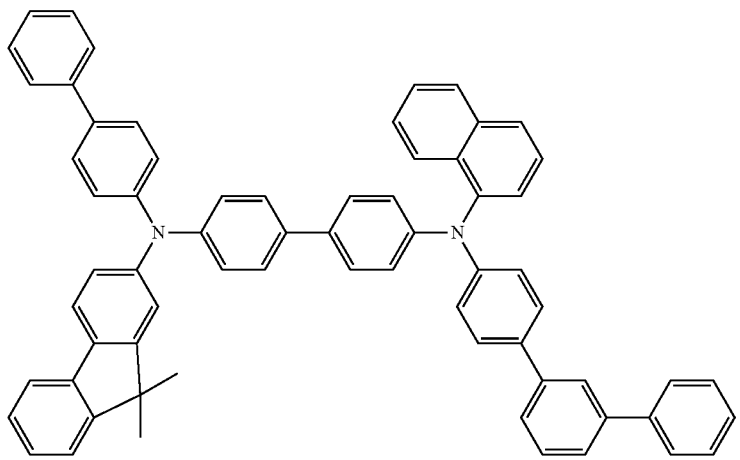
Specific Example 189
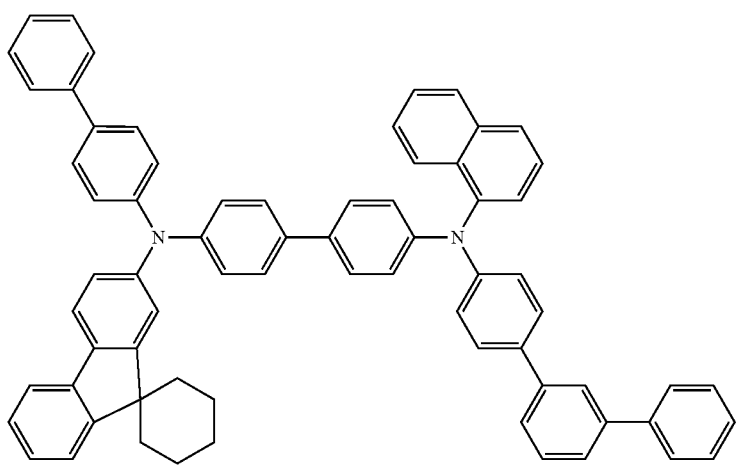
Specific Example 190
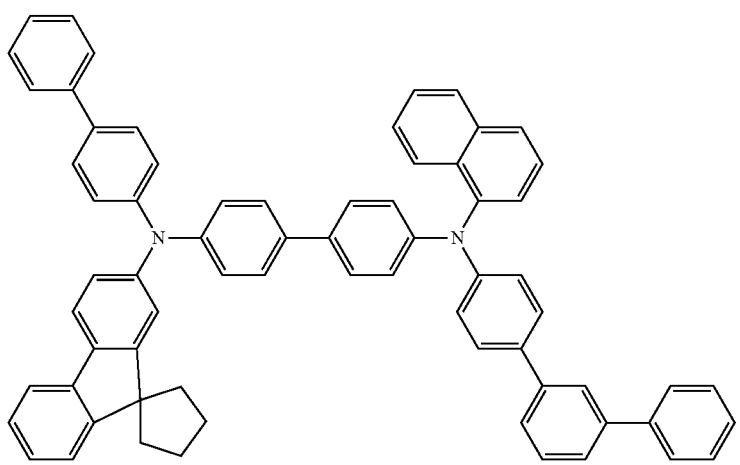

Specific Example 191
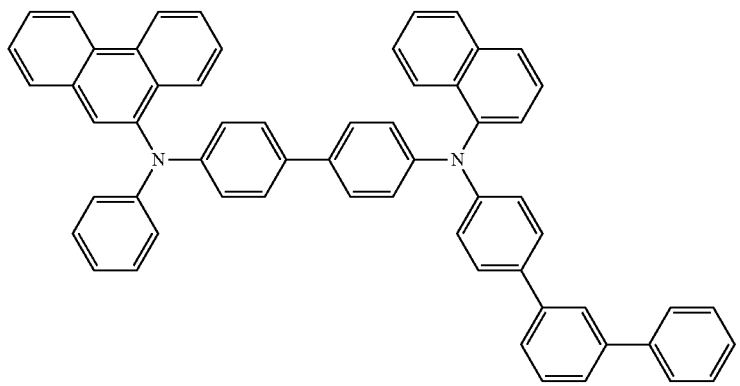
Specific Example 192
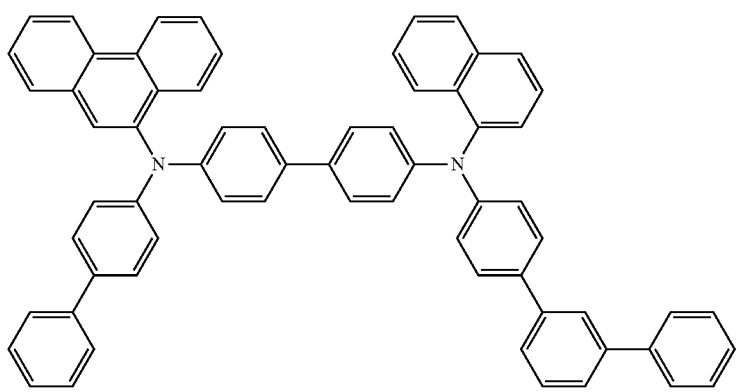
Specific Example 193
Specific Example 194
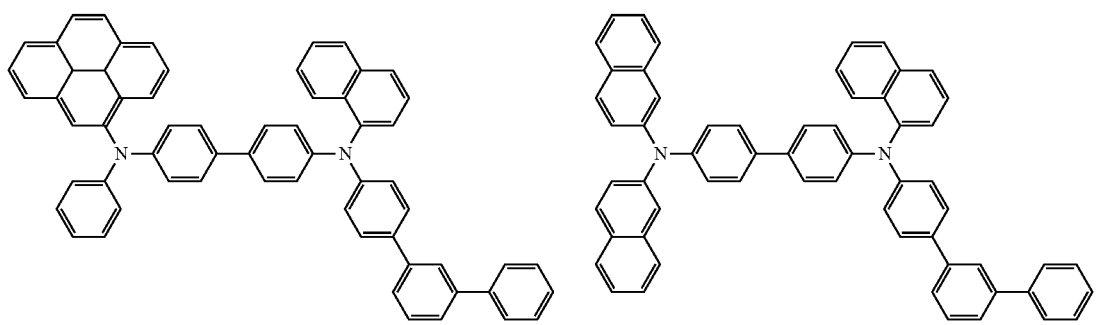
Specific Example 195
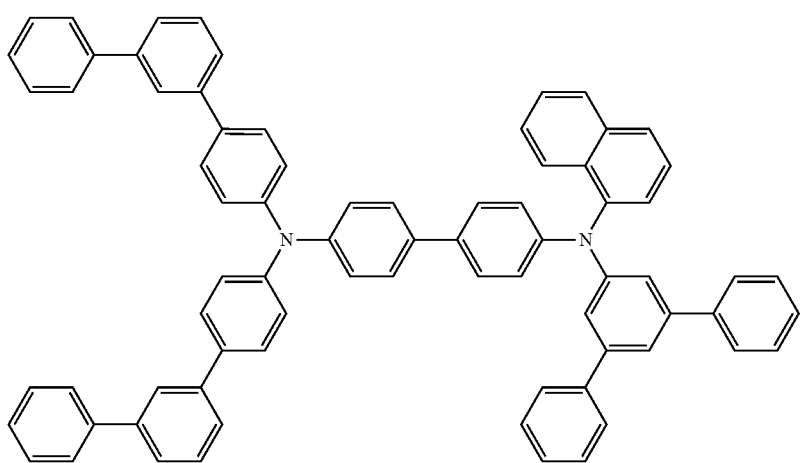

Specific Example 196
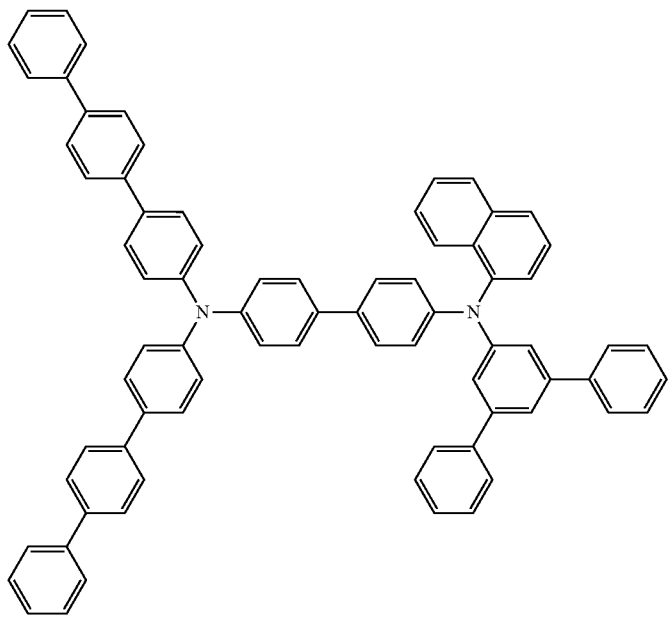
Specific Example 197
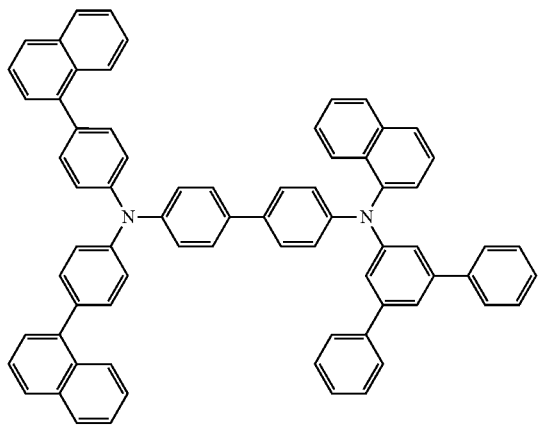
Specific Example 198
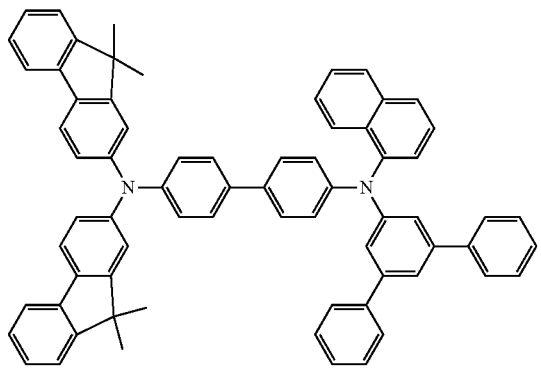
Specific Example 199
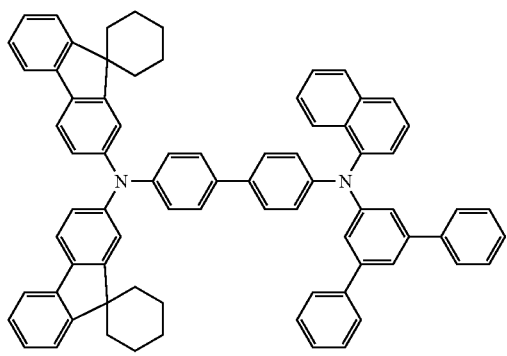
Specific Example 200
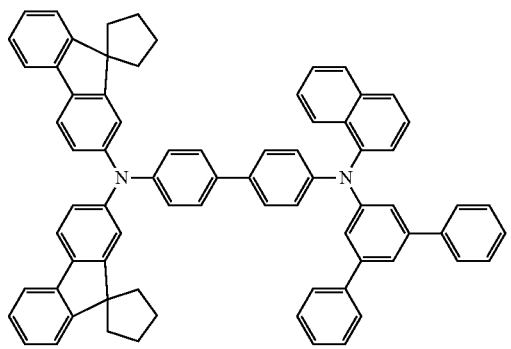

-continued
Specific Example 201
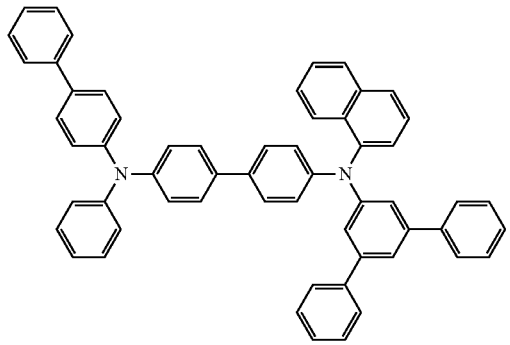
Specific Example 202
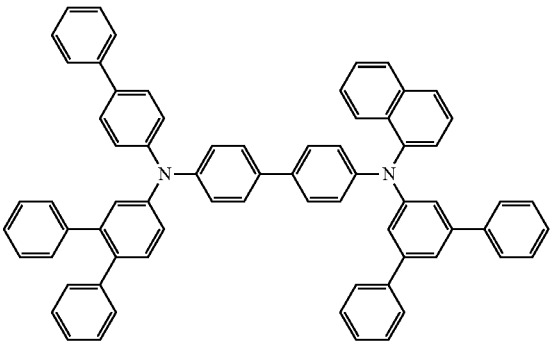
Specific Example 203
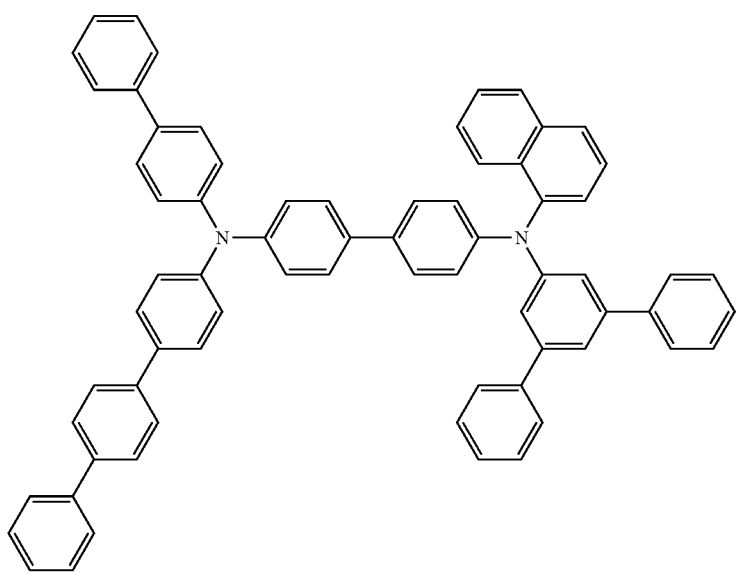
Specific Example 204
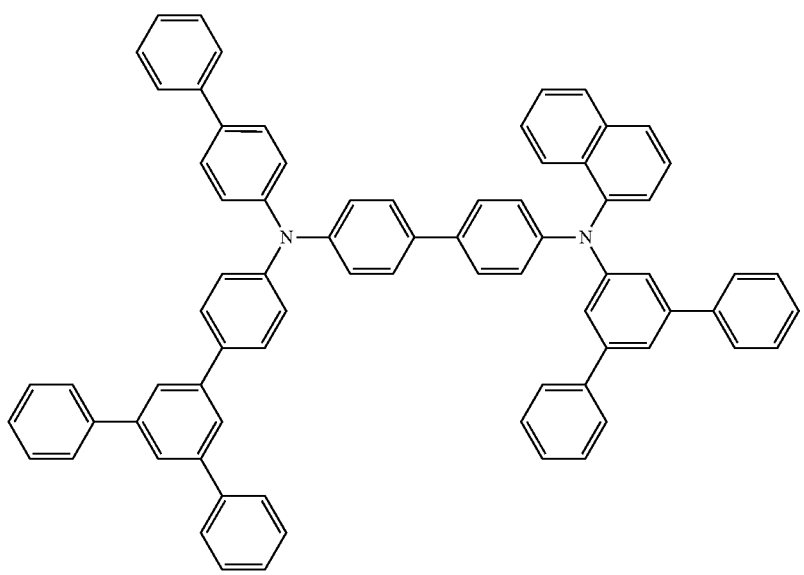

-continued
Specific Example 205
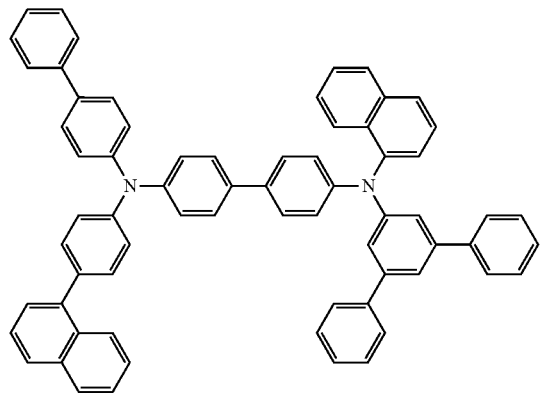
Specific Example 206
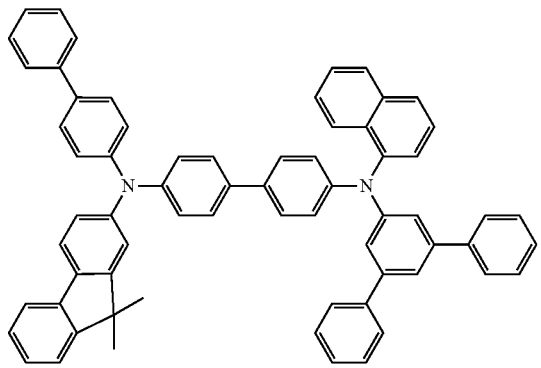
Specific Example 207
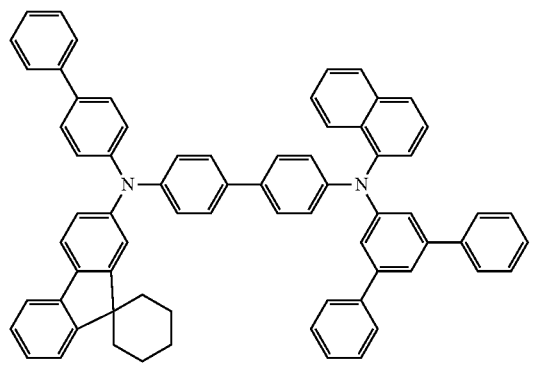
Specific Example 208
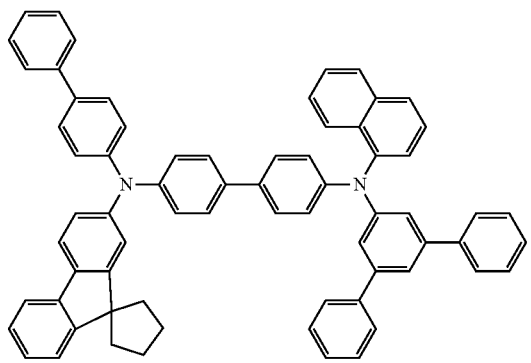
Specific Example 209
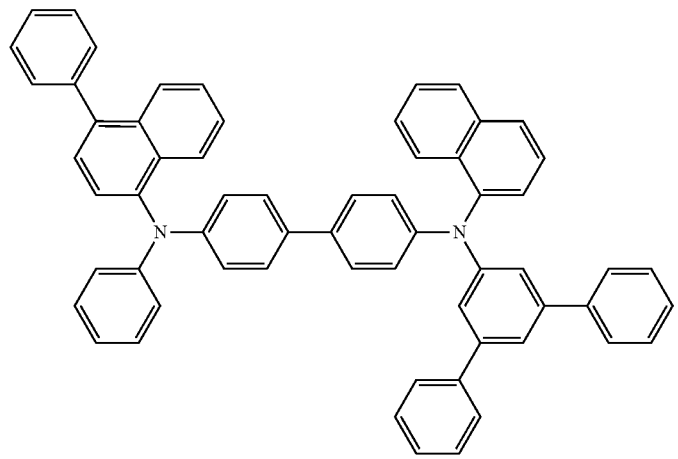

Specific Example 210
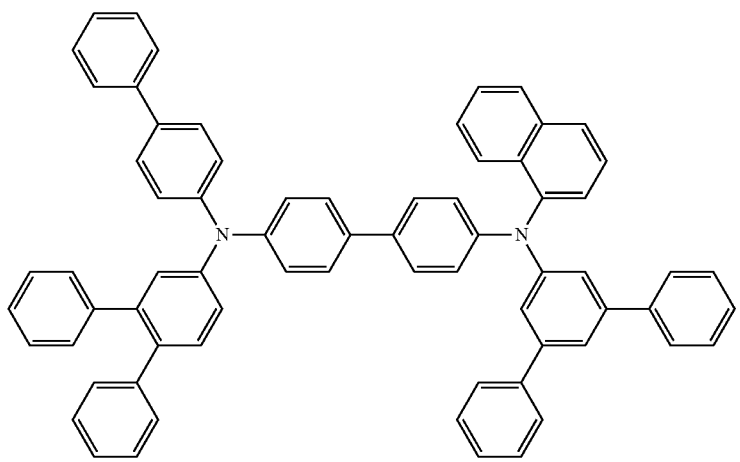
Specific Example 211
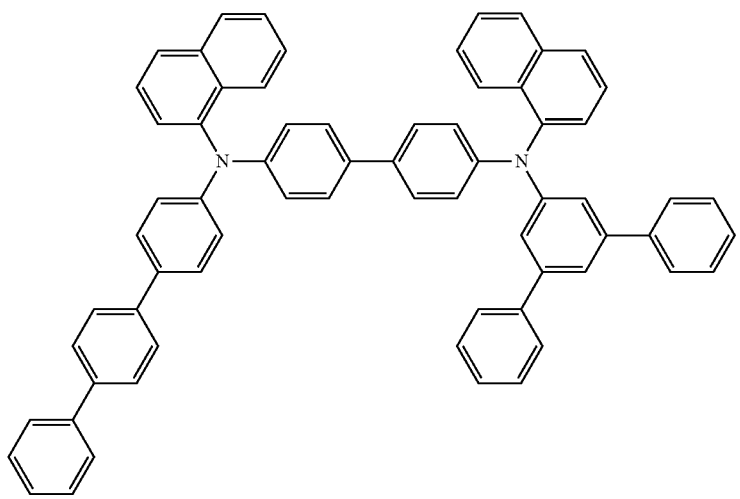
Specific Example 212
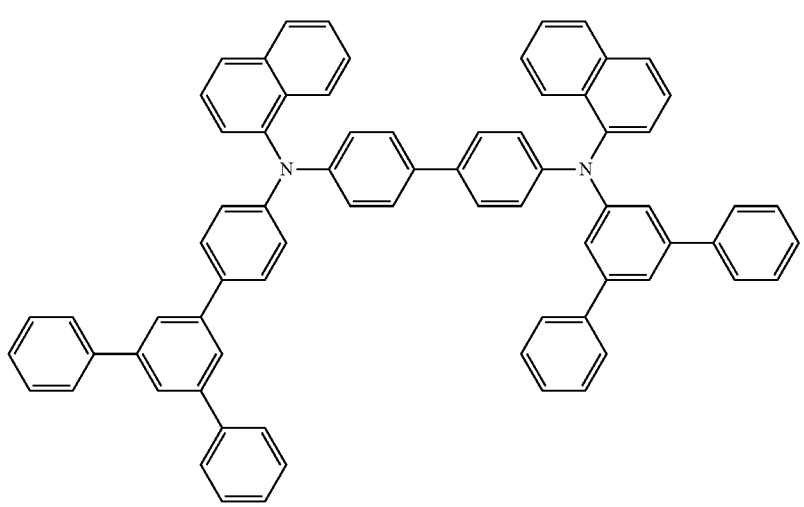

-continued
Specific Example 213
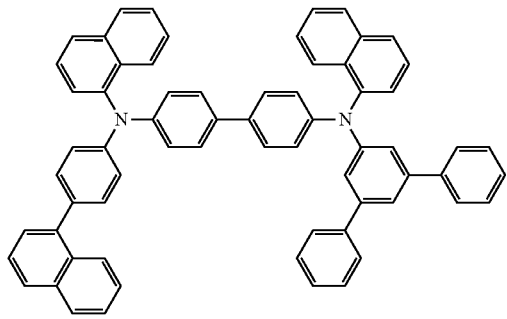
Specific Example 214
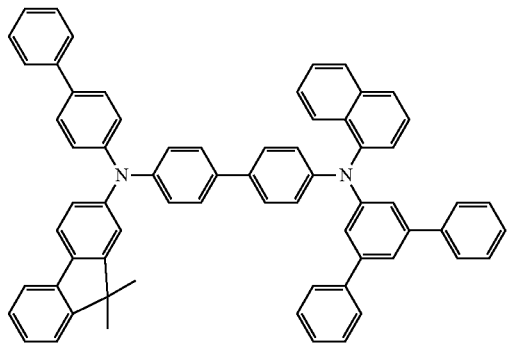
Specific Example 215
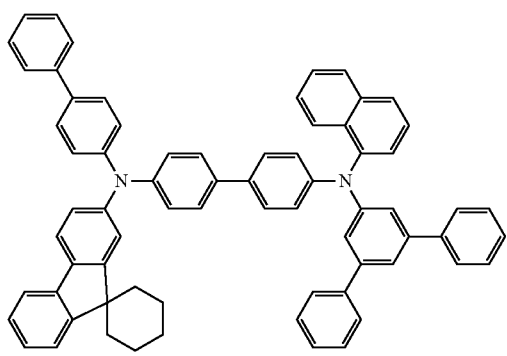
Specific Example 216
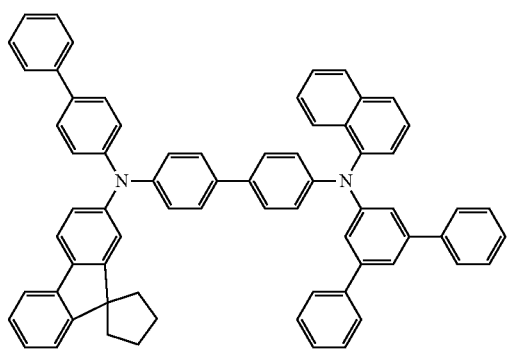
Specific Example 217
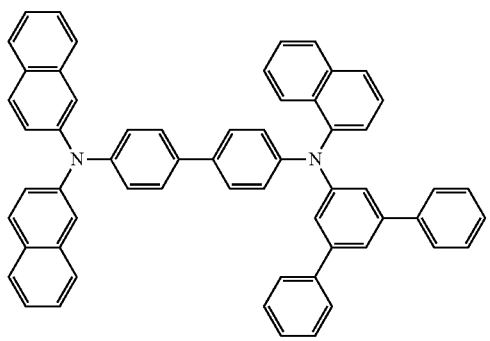
Specific Example 218
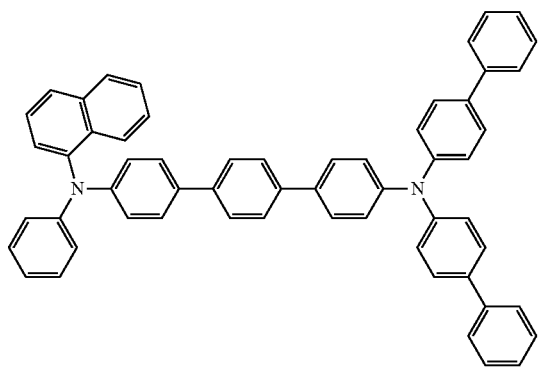
Specific Example 219
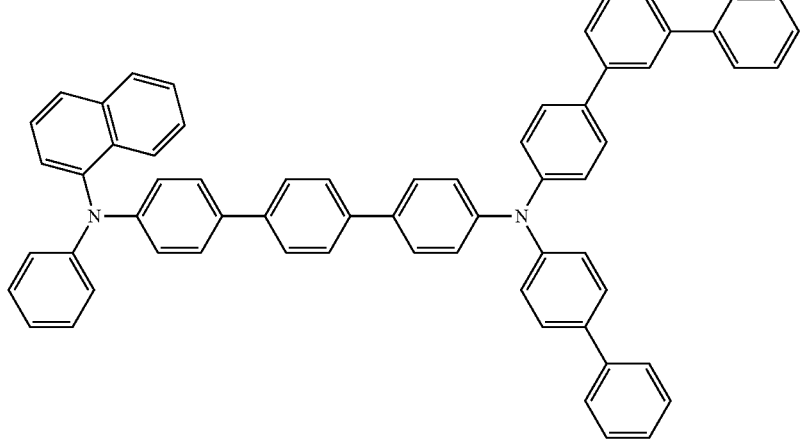

Specific Example 220
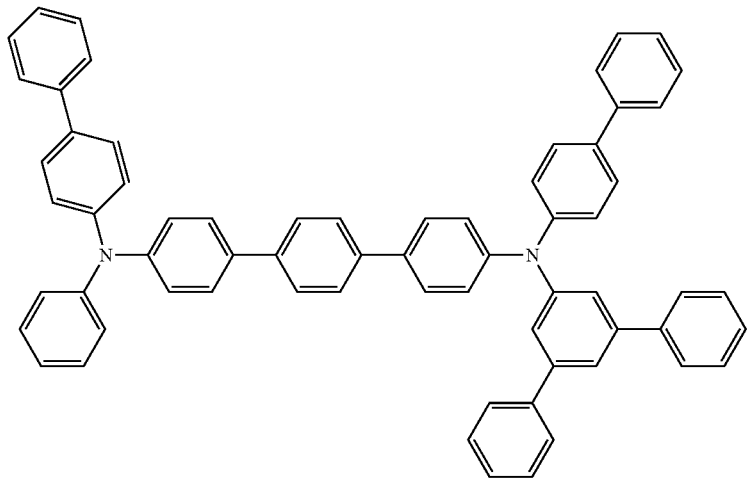
Specific Example 221
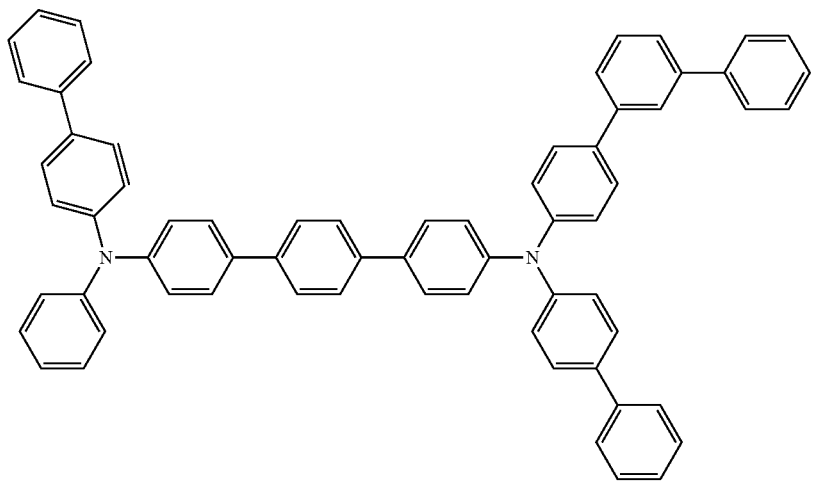
Specific Example 222              Specific Example 223
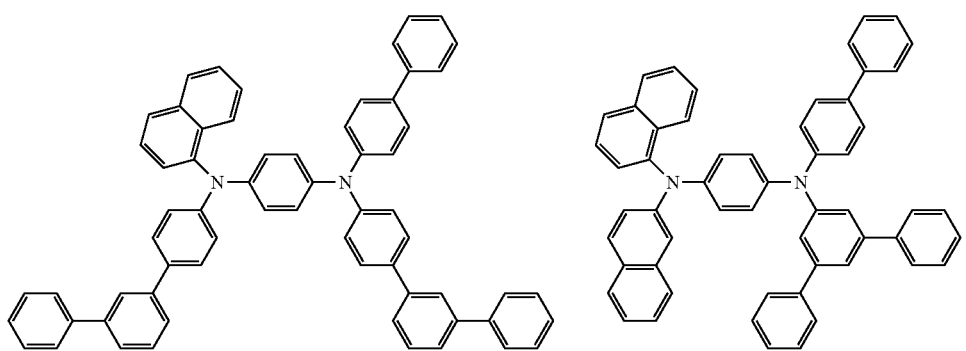

-continued
Specific Example 224
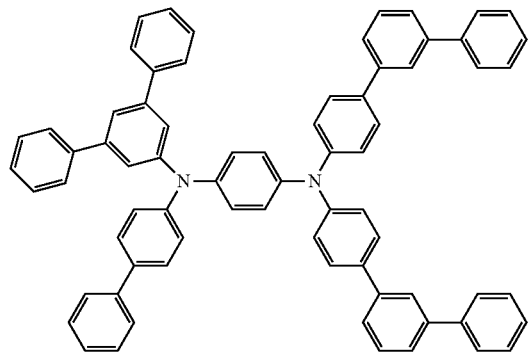
Specific Example 225
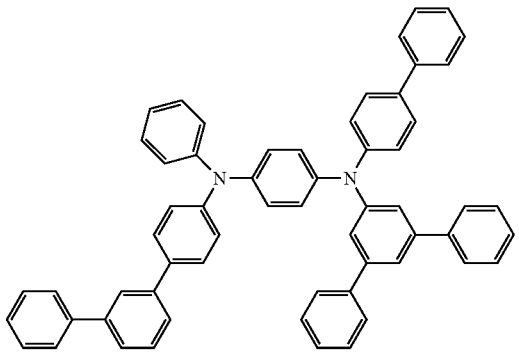
Specific Example 226
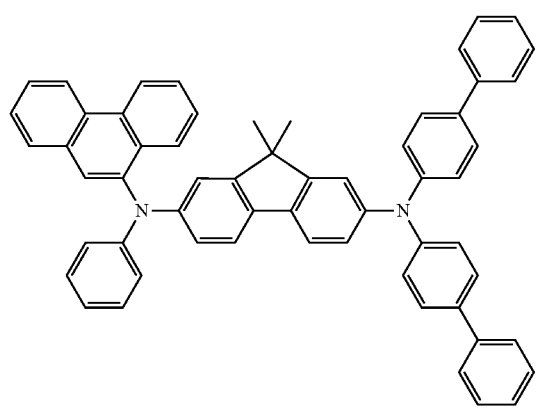
Specific Example 227
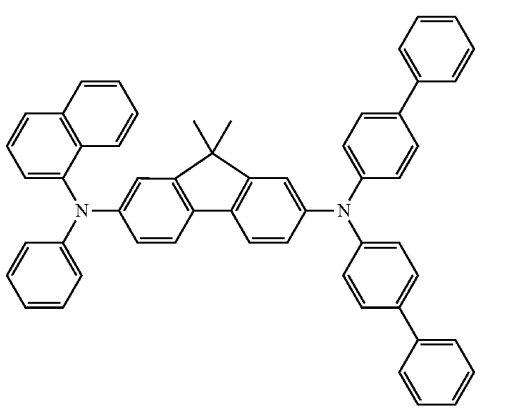
Specific Example 228
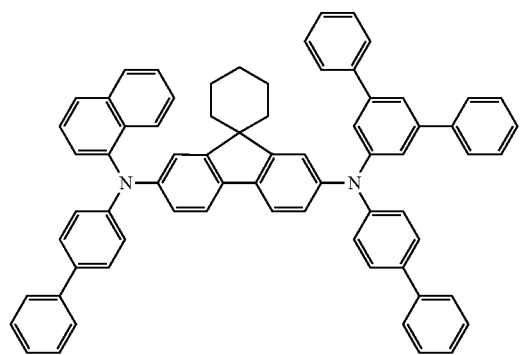
Specific Example 229
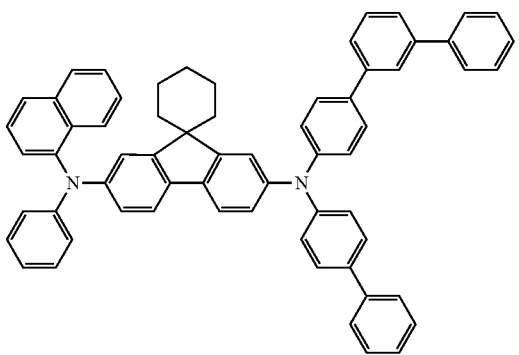
Specific Example 230
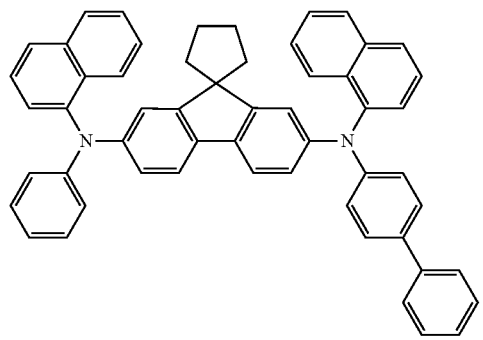
Specific Example 231
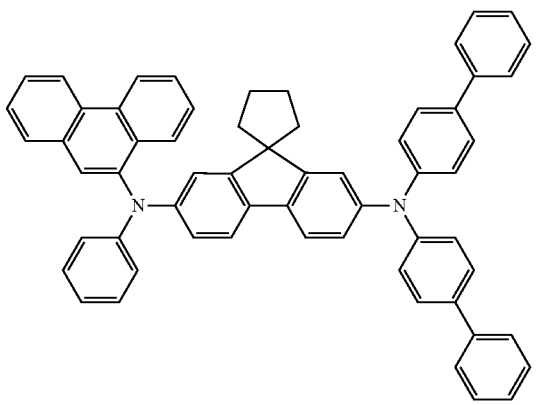

Next, the organic EL device of the present invention will be described.

An organic EL device of the present invention includes one or multiple organic thin film layers including at least a light emitting layer, the one or multiple organic thin film layers being interposed between a cathode and an anode, in which at least one layer of the one or more multiple organic thin film layers contains the aromatic amine derivative alone or as a component of a mixture.

In the organic EL device of the present invention, it is preferable that: the one or multiple organic thin film layers have a hole transporting layer; and the hole transporting layer contain the aromatic amine derivative of the present invention alone or as a component of a mixture. It is more preferable that the hole transporting layer contain the aromatic amine derivative of the present invention as a main component.

The aromatic amine derivative of the present invention is particularly preferably used in an organic EL device that emits blue-based light.

In addition, in the organic EL device of the present invention, the light emitting layer preferably contains an aryl amine compound and/or a styrylamine compound.

Examples of the arylamine compound include compounds each represented by the following general formula (A), and examples of the styrylamine compound include compounds each represented by the following general formula (B).

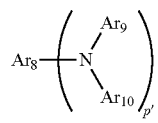
(A)

In the general formula (A), $Ar_8$ represents a group selected from phenyl, biphenyl, terphenyl, stilbene, and distyrylaryl groups, $Ar_9$ and $Ar_{10}$ each represent a hydrogen atom or an aromatic group having 6 to 20 carbon atoms, each of $Ar_9$ and $Ar_{10}$ may be substituted, p' represents an integer of 1 to 4, and $Ar_9$ and/or $Ar_{10}$ are/is more preferably substituted by a styryl group.

Here, the aromatic group having 6 to 20 carbon atoms is preferably a phenyl group, a naphthyl group, an anthranyl group, a phenanthryl group, a terphenyl group, or the like.

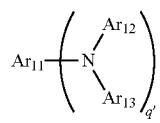
(B)

In the general formula (B), $Ar_{11}$ to $Ar_{13}$ each represent an aryl group which has 5 to 40 ring carbon atoms and which may be substituted, and q' represents an integer of 1 to 4.

Here, examples of the aryl group having 5 to 40 ring atoms preferably include phenyl, naphthyl, anthranyl, phenanthryl, pyrenyl, coronyl, biphenyl, terphenyl, pyrrolyl, furanyl, thiophenyl, benzothiophenyl, oxadiazolyl, diphenylanthranyl, indolyl, carbazolyl, pyridyl, benzoquinolyl, fluoranthenyl, acenaphthofluoranthenyl, and stilbene. In addition, the aryl group having 5 to 40 ring atoms may further be substituted by a substituent. Examples of the substituent preferably include: an alkyl group having 1 to 6 carbon atoms such as an ethyl group, a methyl group, an isopropyl group, an n-propyl group, an s-butyl group, a t-butyl group, a pentyl group, a hexyl group, a cyclopentyl group, or a cyclohexyl group; an alkoxy group having 1 to 6 carbon atoms such as an ethoxy group, a methoxy group, an isopropoxy group, an n-propoxy group, an s-butoxy group, a t-butoxy group, a pentoxy group, a hexyloxy group, a cyclopentoxy group, or a cyclohexyloxy group; an aryl group having 5 to 40 ring atoms; an amino group substituted by an aryl group having 5 to 40 ring atoms; an ester group containing an aryl group having 5 to 40 ring atoms; an ester group containing an alkyl group having 1 to 6 carbon atoms; a cyano group; a nitro group; and a halogen atom such as chlorine, bromine, or iodine.

The structure of the organic EL device of the present invention will be described in the following.

(1) Organic EL Device Structure

Typical examples of the structure of the organic EL device of the present invention include the following:

(1) an anode/light emitting layer/cathode;

(2) an anode/hole injecting layer/light emitting layer/cathode;

(3) an anode/light emitting layer/electron injecting layer/cathode;

(4) an anode/hole injecting layer/light emitting layer/electron injecting layer/cathode;

(5) an anode/organic semiconductor layer/light emitting layer/cathode;

(6) an anode/organic semiconductor layer/electron barrier layer/light emitting layer/cathode;

(7) an anode/organic semiconductor layer/light emitting layer/adhesion improving layer/cathode;

(8) an anode/hole injecting layer/hole transporting layer/light emitting layer/electron injecting layer/cathode;

(9) an anode/insulating layer/light emitting layer/insulating layer/cathode;

(10) an anode/inorganic semiconductor layer/insulating layer/light emitting layer/insulating layer/cathode;

(11) an anode/organic semiconductor layer/insulating layer/light emitting layer/insulating layer/cathode;

(12) an anode/insulating layer/hole injecting layer/hole transporting layer/light emitting layer/insulating layer/cathode; and

(13) an anode/insulating layer/hole injecting layer/hole transporting layer/light emitting layer/electron injecting layer/cathode.

Of those, the structure (8) is preferably used in ordinary cases. However, the structure is not limited to the foregoing.

The aromatic amine derivative of the present invention may be used in any one of the organic thin film layers of the organic EL device. The derivative can be used in a light emitting zone or a hole transporting zone. The derivative is used preferably in the hole transporting zone, or particularly preferably in a hole transporting layer, thereby making a molecule hardly crystallize and improving yields upon production of the organic EL device.

The amount of the aromatic amine derivative of the present invention to be incorporated into the organic thin film layers is preferably 30 to 100 mol %.

(2) Transparent Substrate

The organic EL device of the present invention is prepared on a transparent substrate. Here, the transparent substrate is the substrate which supports the organic EL device. It is preferable that the transparent substrate have a transmittance of light of 50% or greater in the visible region of 400 to 700 nm and be flat and smooth.

Examples of the transparent substrate include glass plates and polymer plates. Specific examples of the glass plate include plates made of soda-lime glass, glass containing barium and strontium, lead glass, aluminosilicate glass, borosilicate glass, barium borosilicate glass, and quartz. Specific examples of the polymer plate include plates made of polycarbonate resins, acrylic resins, polyethylene terephthalate, polyether sulfide, and polysulfone.

(3) Anode

The anode in the organic EL device of the present invention has the function of injecting holes into the hole transporting layer or the light emitting layer. It is effective that the anode has a work function of 4.5 eV or greater. Specific examples of the material for the anode used in the present invention include indium tin oxide (ITO) alloys, tin oxide (NESA), indium zinc oxide (IZO), gold, silver, platinum, and copper.

The anode can be prepared by forming a thin film of the electrode material described above in accordance with a process such as the vapor deposition process and the sputtering process.

When the light emitted from the light emitting layer is obtained through the anode, it is preferable that the anode have a transmittance of the emitted light greater than 10%. It is also preferable that the sheet resistivity of the anode be several hundred Ω/□ or smaller. The thickness of the anode is, in general, selected in the range of 10 nm to 1 μm and preferably in the range of 10 to 200 nm although the preferable range may be different depending on the used material.

(4) Light Emitting Layer

The light emitting layer in the organic EL device has a combination of the following functions (1) to (3).

(1) The injecting function: the function of injecting holes from the anode or the hole injecting layer and injecting electrons from the cathode or the electron injecting layer when an electric field is applied.

(2) The transporting function: the function of transporting injected charges (i.e., electrons and holes) by the force of the electric field.

(3) The light emitting function: the function of providing the field for recombination of electrons and holes and leading to the emission of light.

However, the easiness of injection may be different between holes and electrons and the ability of transportation expressed by the mobility may be different between holes and electrons. It is preferable that either one of the charges be transferred.

For the process for forming the light emitting layer, a known process such as the vapor deposition process, the spin coating process, and the LB process can be used. It is particularly preferable that the light emitting layer be a molecular deposit film. The molecular deposit film is a thin film formed by deposition of a material compound in the gas phase or a film formed by solidification of a material compound in a solution or in the liquid phase. In general, the molecular deposit film can be distinguished from the thin film formed in accordance with the LB process (i.e., molecular accumulation film) based on the differences in aggregation structure and higher order structure and functional differences caused by those structural differences.

Further, as disclosed in JP-A-57-51781, the light emitting layer can also be formed by dissolving a binder such as a resin and the material compounds into a solvent to prepare a solution, followed by forming a thin film from the prepared solution by the spin coating process or the like.

In the present invention, where desired, the light emitting layer may include other known light emitting materials other than the light emitting material composed of the aromatic amine derivative of the present invention, or a light emitting layer including other known light emitting material may be laminated to the light emitting layer including the light emitting material composed of the aromatic amine derivative of the present invention as long as the object of the present invention is not adversely affected.

Examples of a light emitting material or a doping material which can be used in the light emitting layer together with the aromatic amine derivative of the present invention include, but not limited to, anthracene, naphthalene, phenanthrene, pyrene, tetracene, coronene, chrysene, fluoresceine, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, quinoline metal complexes, aminoquinoline metal complexes, benzoquinoline metal complexes, imine, diphenylethylene, vinylanthracene, diaminocarbazole, pyrane, thiopyrane, polymethine, merocyanine, imidazole-chelated oxynoid compounds, quinacridone, rubrene, and fluorescent dyes.

A host material that can be used in a light emitting layer together with the aromatic amine derivative of the present invention is preferably a compound represented by any one of the following formulae (i) to (ix).

An asymmetric anthracene represented by the following general formula (i):

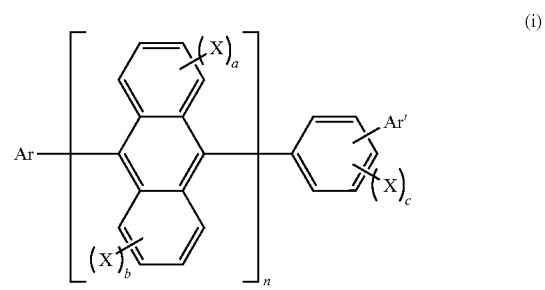

where:

Ar represents a substituted or unsubstituted fused aromatic group having 10 to 50 ring carbon atoms;

Ar' represents a substituted or unsubstituted aromatic group having 6 to 50 ring carbon atoms;

X represents a substituted or unsubstituted aromatic group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a carboxyl group, a halogen atom, a cyano group, a nitro group, or a hydroxyl group.

a, b, and c each represent an integer of 0 to 4; and n represents an integer of 1 to 3. In addition, when n represents 2 or more, anthracene nuclei in [ ] may be identical to or different from each other.

An asymmetric monoanthracene derivative represented by the following general formula (ii):

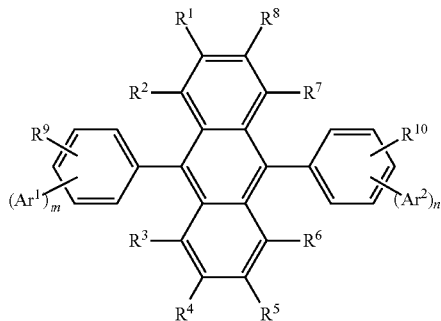

where:

Ar$^1$ and Ar$^2$ each independently represent a substituted or unsubstituted aromatic ring group having 6 to 50 ring carbon atoms. m and n each represent an integer of 1 to 4; provided that Ar$^1$ and Ar$^2$ are not identical to each other when m=n=1 and positions at which Ar$^1$ and Ar$^2$ are bound to a benzene ring are bilaterally symmetric, and m and n represent different integers when m or n represents an integer of 2 to 4; and R$^1$ to R$^{10}$ each independently represent a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group, or a hydroxyl group.

An asymmetric pyrene derivative represented by the following general formula (iii):

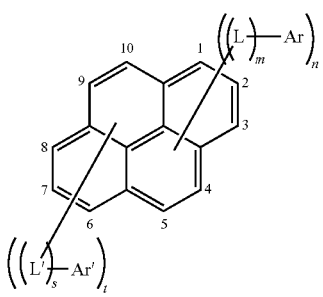

where:

Ar and Ar' each represent a substituted or unsubstituted aromatic group having 6 to 50 ring carbon atoms;

L and L' each represent a substituted or unsubstituted phenylene group, a substituted or unsubstituted naphthalenylene group, a substituted or unsubstituted fluorenylene group, or a substituted or unsubstituted dibenzosilolylene group;

m represents an integer of 0 to 2. n represents an integer of 1 to 4. s represents an integer of 0 to 2. t represents an integer of 0 to 4; and in addition, L or Ar binds to any one of 1- to 5-positions of pyrene, and L' or Ar' binds to any one of 6- to 10-positions of pyrene;

provided that Ar, Ar', L, and L' satisfy the following item (1) or (2) when n+t represents an even number, (1) Ar≠Ar' and/or L≠L' (where the symbol "≠" means that groups connected with the symbol have different structures)

(2) When Ar=Ar' and L=L', (2-1) m≠s and/or n t, or (2-2) when m=s and n=t, (2-2-1) L and L' or pyrene bind or binds to different binding positions on Ar and Ar', or (2-2-2) in the case where L and L' or pyrene bind or binds to the same binding positions on Ar and Ar', the case where the substitution positions of L and L', or of Ar and Ar' in pyrene are 1- and 6-positions, or 2- and 7-positions does not occur.

An asymmetric anthracene derivative represented by the following general formula (iv):

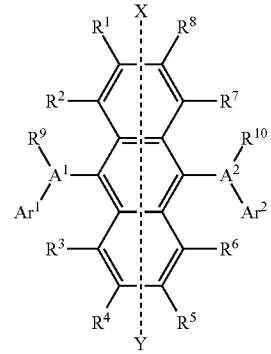

where:

A$^1$ and A$^2$ each independently represent a substituted or unsubstituted fused aromatic ring group having 10 to 20 ring carbon atoms;

Ar$^1$ and Ar$^2$ each independently represent a hydrogen atom, or a substituted or unsubstituted aromatic ring group having 6 to 50 ring carbon atoms;

R$^1$ to R$^{10}$ each independently represent a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group, or a hydroxyl group; and the number of each of Ar$^1$, Ar$^2$, R$^9$, and R$^{10}$ may be two or more, and adjacent groups may form a saturated or unsaturated cyclic structure;

provided that the case where groups symmetric with respect to the X-Y axis shown on central anthracene in the general formula (1) bind to 9- and 10-positions of the anthracene does not occur.

An anthracene derivative represented by the following general formula (v):

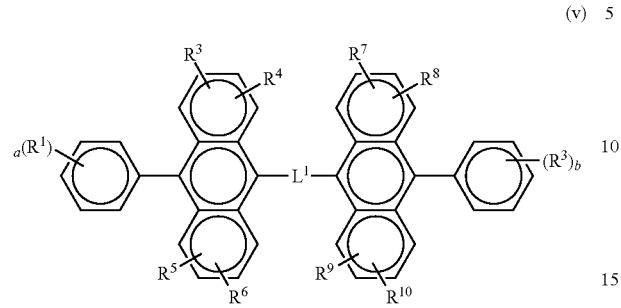

(v)

where: $R^1$ to $R^{10}$ each independently represent a hydrogen atom, an alkyl group, a cycloalkyl group, an aryl group which may be substituted, an alkoxyl group, an aryloxy group, an alkylamino group, an alkenyl group, an arylamino group, or a heterocyclic group which may be substituted; a and b each represent an integer of 1 to 5, and, when a or b represents 2 or more, $R^1$'s or $R^2$'s may be identical to or different from each other, or $R^1$'s or $R^2$'s may be bonded to each other to form a ring; $R^3$ and $R^4$, $R^5$ and $R^6$, $R^7$ and $R^8$, or $R^9$ and $R^{10}$ may be bonded to each other to form a ring; and $L^1$ represents a single bond, —O—, —S—, —N(R)— where R represents an alkyl group or an aryl group which may be substituted, an alkylene group, or an arylene group.

An anthracene derivative represented by the following general formula (vi):

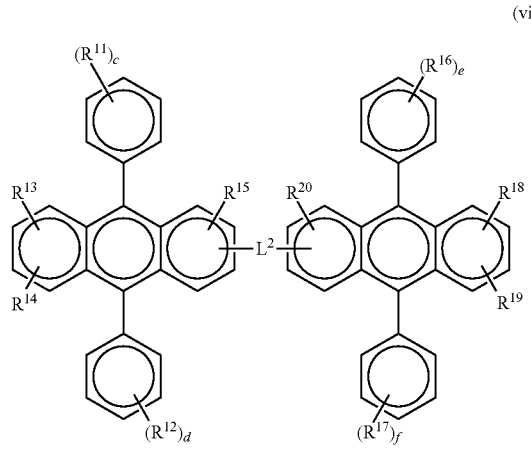

(vi)

where: $R^{11}$ to $R^{20}$ each independently represent a hydrogen atom, an alkyl group, a cycloalkyl group, an aryl group, an alkoxyl group, an aryloxy group, an alkylamino group, an arylamino group, or a heterocyclic group which may be substituted; c, d, e, and f each represent an integer of 1 to 5, and, when any one of c, d, e, and f represents 2 or more, $R^{11}$'s, $R^{12}$'s, $R^{16}$'s, or $R^{17}$'s may be identical to or different from each other, or $R^{11}$'s, $R^{12}$'s, $R^{16}$'s, or $R^{17}$'s may be bonded to each other to form a ring; $R^{13}$ and $R^{14}$, or $R^{18}$ and $R^{19}$ may be bonded to each other to form a ring; and $L^2$ represents a single bond, —O—, —S—, —N(R)— where R represents an alkyl group or an aryl group which may be substituted, an alkylene group, or an arylene group.

A spirofluorene derivative represented by the following general formula (vii):

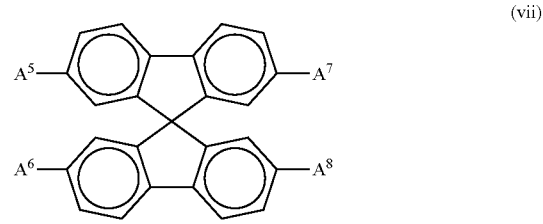

(vii)

where $A^5$ to $A^8$ each independently represent a substituted or unsubstituted biphenyl group, or a substituted or unsubstituted naphthyl group.

A fused ring-containing compound represented by the following general formula (viii):

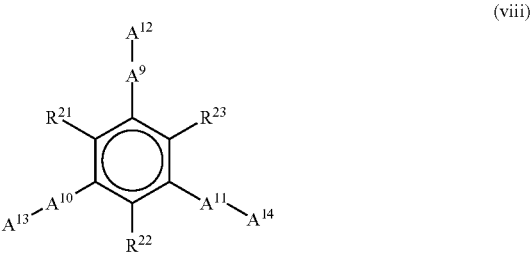

(viii)

where: $A^9$ to $A^{14}$ each have the same meaning as that described above; $R^{21}$ to $R^{23}$ each independently represent a hydrogen atom, an alkyl group having 1 to 6 carbon atoms, a cycloalkyl group having 3 to 6 carbon atoms, an alkoxyl group having 1 to 6 carbon atoms, an aryloxy group having 5 to 18 carbon atoms, an aralkyloxy group having 7 to 18 carbon atoms, an arylamino group having 5 to 16 carbon atoms, a nitro group, a cyano group, an ester group having 1 to 6 carbon atoms, or a halogen atom; and at least one of $A^9$ to $A^{14}$ represents a group having three or more fused aromatic rings.

A fluorene compound represented by the following general formula (ix):

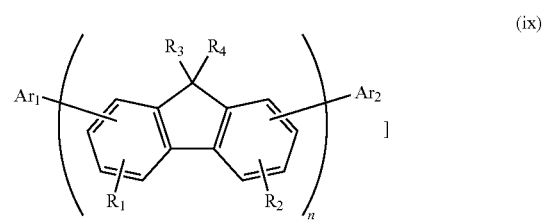

(ix)

where: $R_1$ and $R_2$ each represent a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group, or a halogen atom; $R_1$'s or $R_2$'s bonded to different fluorene groups may be identical to or different from each other, and $R_1$ and $R_2$ bonded to the same fluorene group may be identical to or different from each other; $R_3$ and $R_4$ each represent a hydrogen atom, a substituted or unsubstituted alkyl group, a substituted or unsubstituted aralkyl group, a substituted or unsubstituted aryl group, or a substituted or unsubstituted heterocyclic group; R₃'s or R₄'s bonded to different fluorene groups may be identical to or different from each other, and R₃ and R₄ bonded to the same fluorene group may be identical to or different from each other; Ar₁ and Ar₂ each represent a substituted or unsubstituted fused polycyclic aromatic group having three or more benzene rings in total, or a substituted or unsubstituted fused polycyclic heterocyclic group that has three or more rings each of which is a benzene ring or a heterocyclic ring in total and that is bonded to a fluorene group by carbon, and Ar₁ and Ar₂ may be identical to or different from each other; and n represents an integer of 1 to 10.

Of the above-mentioned host materials, an anthracene derivative is preferable, a monoanthracene derivative is more preferable, and an asymmetric anthracene is particularly preferable.

In addition, a phosphorescent compound can also be used as a light emitting material for a dopant. A compound containing a carbazole ring as a host material is preferable as the phosphorescent compound. The dopant is a compound capable of emitting light from a triplet exciton, and is not particularly limited as long as light is emitted from a triplet exciton, a metal complex containing at least one metal selected from the group consisting of Ir, Ru, Pd, Pt, Os, and Re is preferable, and a porphyrin metal complex or an orthometalated metal complex is preferable.

A host composed of a compound containing a carbazole ring and suitable for phosphorescence is a compound having a function of causing a phosphorescent compound to emit light as a result of the occurrence of energy transfer from the excited state of the host to the phosphorescent compound. A host compound is not particularly limited as long as it is a compound capable of transferring exciton energy to a phosphorescent compound, and can be appropriately selected in accordance with a purpose. The host compound may have, for example, an arbitrary heterocyclic ring in addition to a carbazole ring.

Specific examples of such a host compound include a carbazole derivative, a triazole derivative, an oxazole derivative, an oxadiazole derivative, an imidazole derivative, a polyarylalkane derivative, a pyrazoline derivative, a pyrazolone derivative, a phenylene diamine derivative, an aryl amine derivative, an amino substituted chalcone derivative, a styrylanthracene derivative, a fluorenone derivative, a hydrazone derivative, a stilbene derivative, a silazane derivative, an aromatic tertiary amine compound, a styryl amine compound, an aromatic dimethylidene-based compound, a porphyrin-based compound, an anthraquinodimethane derivative, an anthrone derivative, a diphenylquinone derivative, a thiopyranedioxide derivative, a carbodiimide derivative, a fluorenilidene methane derivative, a distyrylpyrazine derivative, a heterocyclic tetracarboxylic anhydride such as naphthaleneperylene, a phthalocyanine derivative, various metal complex polysilane-based compounds typified by a metal complex of an 8-quinolinol derivative or a metal complex having metal phthalocyanine, benzooxazole, or benzothiazole as a ligand, and polymer compounds such as a poly(N-vinylcarbazole) derivative, an aniline-based copolymer, a conductive high molecular weight oligomer such as a thiophene oligomer or polythiophene, a polythiophene derivative, a polyphenylene derivative, a polyphenylene vinylene derivative, and a polyfluorene derivative. One of the host materials may be used alone, or two or more of them may be used in combination.

Specific examples thereof include the compounds as described below.

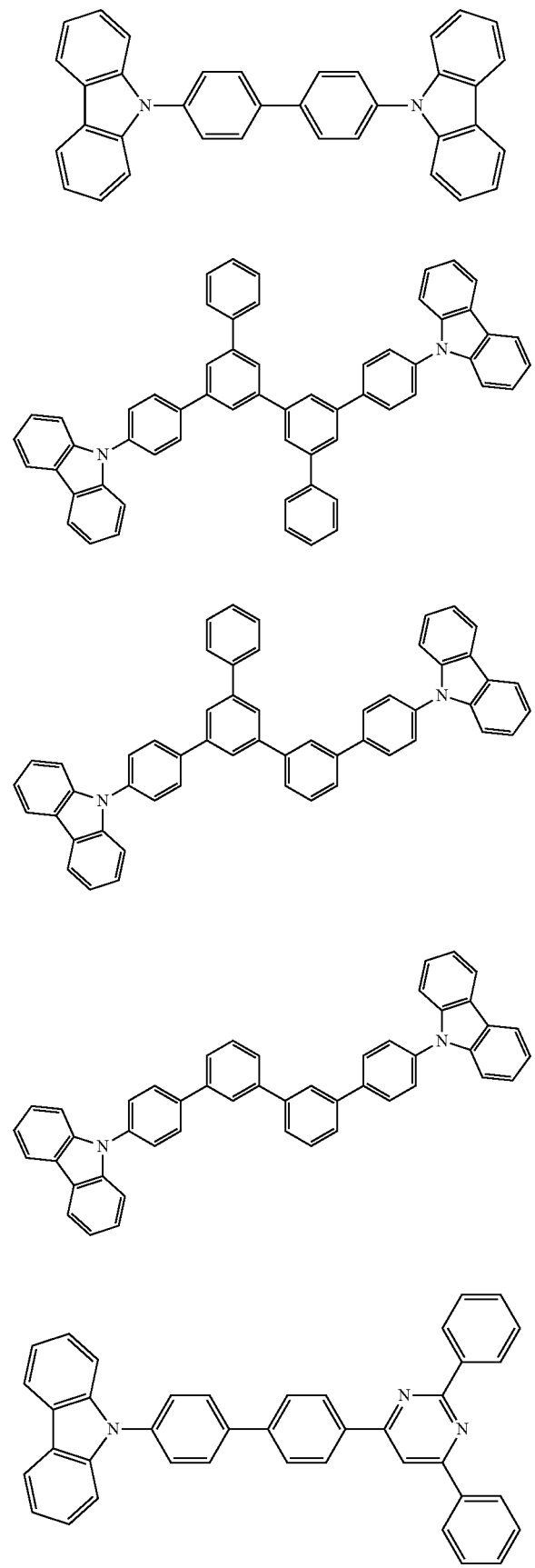

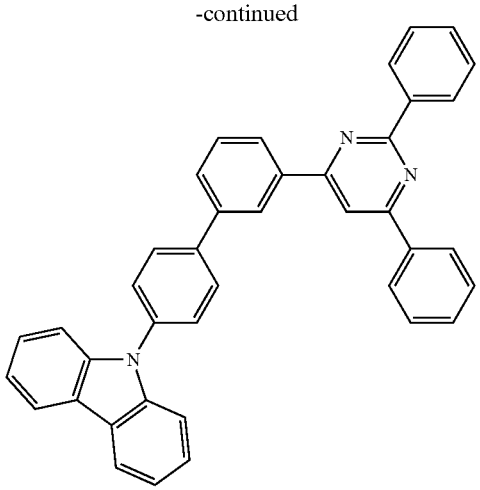

A phosphorescent dopant is a compound capable of emitting light from a triplet exciton. The dopant, which is not particularly limited as long as light is emitted from a triplet exciton, is preferably a metal complex containing at least one metal selected from the group consisting of Ir, Ru, Pd, Pt, Os, and Re, and is preferably a porphyrin metal complex or an orthometalated metal complex. A porphyrin platinum complex is preferable as the porphyrin metal complex. One kind of a phosphorescent compound may be used alone, or two or more kinds of phosphorescent compounds may be used in combination.

Any one of various ligands can be used for forming an orthometalated metal complex. Examples of a preferable ligand include a 2-phenylpyridine derivative, a 7,8-benzoquinoline derivative, a 2-(2-thienyl)pyridine derivative, a 2-(1-naphthyl)pyridine derivative, and a 2-phenylquinoline derivative. Each of those derivatives may have a substituent as required. A fluoride of any one of those derivatives, or one obtained by introducing a trifluoromethyl group into any one of those derivatives is a particularly preferable blue-based dopant. The metal complex may further include a ligand other than the above-mentioned ligands such as acetylacetonate or picric acid as an auxiliary ligand.

The content of the phosphorescent dopant in the light emitting layer is not particularly limited, and can be appropriately selected in accordance with a purpose. The content is, for example, 0.1 to 70 mass %, and is preferably 1 to 30 mass %. When the content of the phosphorescent compound is less than 0.1 mass %, the intensity of emitted light is weak, and an effect of the incorporation of the compound is not sufficiently exerted. When the content exceeds 70 mass %, a phenomenon referred to as concentration quenching becomes remarkable, and device performance reduces.

In addition, the light emitting layer may contain a hole transporting material, an electron transporting material, or a polymer binder as required.

Further, the thickness of the light emitting layer is preferably 5 to 50 nm, more preferably 7 to 50 nm, or most preferably 10 to 50 nm. When the thickness is less than 5 nm, it becomes difficult to form the light emitting layer, so the adjustment of chromaticity may be difficult. When the thickness exceeds 50 nm, the voltage at which the device is driven may increase.

(5) Hole Injecting and Transporting Layer (Hole Transporting Zone)

The hole injecting and transporting layer is a layer which helps injection of holes into the light emitting layer and transports the holes to the light emitting region. The layer exhibits a great mobility of holes and, in general, has an ionization energy as small as 5.5 eV or smaller. For such the hole injecting and transporting layer, a material which transports holes to the light emitting layer under an electric field of a smaller strength is preferable. A material which exhibits, for example, a mobility of holes of at least $10^{-4}$ $m^2$/V·sec under application of an electric field of $10^4$ to $10^6$ V/cm is preferable.

When the aromatic amine derivative of the present invention is used in the hole transporting zone, the aromatic amine derivative of the present invention may be used alone or as a mixture with other materials for forming the hole injecting and transporting layer.

The material which can be used for forming the hole injecting and transporting layer as a mixture with the aromatic amine derivative of the present invention is not particularly limited as long as the material has a preferable property described above. The material can be arbitrarily selected from materials which are conventionally used as the charge transporting material of holes in photoconductive materials and known materials which are used for the hole injecting and transporting layer in organic EL devices.

Specific examples include: a triazole derivative (see, for example, U.S. Pat. No. 3,112,197); an oxadiazole derivative (see, for example, U.S. Pat. No. 3,189,447); an imidazole derivative (see, for example, JP-B-37-16096); a polyarylalkane derivative (see, for example, U.S. Pat. No. 3,615,402, U.S. Pat. No. 3,820,989, U.S. Pat. No. 3,542,544, JP-B-45-555, JP-B-51-10983, JP-A-51-93224, JP-A-55-17105, JP-A-56-4148, JP-A-55-108667, JP-A-55-156953, and JP-A-56-36656); a pyrazoline derivative and a pyrazolone derivative (see, for example, U.S. Pat. No. 3,180,729, U.S. Pat. No. 4,278,746, JP-A-55-88064, JP-A-55-88065, JP-A-49-105537, JP-A-55-51086, JP-A-56-80051, JP-A-56-88141, JP-A-57-45545, JP-A-54-112637, and JP-A-55-74546); a phenylenediamine derivative (see, for example, U.S. Pat. No. 3,615,404, JP-B-51-10105, JP-B-46-3712, JP-B-47-25336, JP-A-54-53435, JP-A-54-110536, and JP-A-54-119925); an arylamine derivative (see, for example, U.S. Pat. No. 3,567,450, U.S. Pat. No. 3,180,703, U.S. Pat. No. 3,240,597, U.S. Pat. No. 3,658,520, U.S. Pat. No. 4,232,103, U.S. Pat. No. 4,175,961, U.S. Pat. No. 4,012,376, JP-B-49-35702, JP-B-39-27577, JP-A-55-144250, JP-A-56-119132, JP-A-56-22437, and DE 1,110,518); an amino-substituted chalcone derivative (see, for example, U.S. Pat. No. 3,526,501); an oxazole derivative (those disclosed in U.S. Pat. No. 3,257,203); a styrylanthracene derivative (see, for example, JP-A-56-46234); a fluorenone derivative (see, for example, JP-A-54-110837); a hydrazone derivative (see, for example, U.S. Pat. No. 3,717,462, JP-A-54-59143, JP-A-55-52063, JP-A-55-52064, JP-A-55-46760, JP-A-55-85495, JP-A-57-11350, JP-A-57-148749, and JP-A-2-311591); a stilbene derivative (see, for example, JP-A-61-210363, JP-A-61-228451, JP-A-61-14642, JP-A-61-72255, JP-A-62-47646, JP-A-62-36674, JP-A-62-10652, JP-A-62-30255, JP-A-60-93445, JP-A-60-94462, JP-A-60-174749, and JP-A-60-175052); a silazane derivative (U.S. Pat. No. 4,950,950); a polysilane-based copolymer (JP-A-2-204996); an aniline-based copolymer (JP-A-2-282263); and a conductive high molecular weight oligomer (particularly a thiophene oligomer) disclosed in JP-A-1-211399.

In addition to the above-mentioned materials which can be used as the material for the hole injecting and transporting layer, a porphyrin compound (those disclosed in, for example, JP-A-63-2956965); an aromatic tertiary amine compound and a styrylamine compound (see, for example, U.S. Pat. No.

4,127,412, JP-A-53-27033, JP-A-54-58445, JP-A-54-149634, JP-A-54-64299, JP-A-55-79450, JP-A-55-144250, JP-A-56-119132, JP-A-61-295558, JP-A-61-98353, and JP-A-63-295695) are preferable, and aromatic tertiary amines are particularly preferable.

Further examples of aromatic tertiary amine compounds include compounds having two fused aromatic rings in the molecule such as 4,4'-bis(N-(1-naphthyl)-N-phenylamino)-biphenyl (hereinafter referred to as NPD) as disclosed in U.S. Pat. No. 5,061,569, and a compound in which three triphenylamine units are bonded together in a star-burst shape, such as 4,4',4''-tris(N-(3-methylphenyl)-N-phenylamino)-triphenylamine (hereinafter referred to as MTDATA) as disclosed in JP-A-4-308688.

Further, in addition to the aromatic dimethylidene-based compounds described above as the material for the light emitting layer, inorganic compounds such as Si of the p-type and SiC of the p-type can also be used as the material for the hole injecting and transporting layer.

The hole injecting and transporting layer can be formed by forming a thin layer from the aromatic amine derivative of the present invention in accordance with a known process such as the vacuum vapor deposition process, the spin coating process, the casting process, and the LB process. The thickness of the hole injecting and transporting layer is not particularly limited. In general, the thickness is 5 nm to 5 μm. The hole injecting and transporting layer may be constituted of a single layer containing one or more materials described above or may be a laminate constituted of hole injecting and transporting layers containing materials different from the materials of the hole injecting and transporting layer described above as long as the aromatic amine derivative of the present invention is incorporated in the hole injecting and transporting zone.

Further, an organic semiconductor layer may be disposed as a layer for helping the injection of holes or electrons into the light emitting layer. As the organic semiconductor layer, a layer having a conductivity of $10^{-10}$ S/cm or greater is preferable. As the material for the organic semiconductor layer, oligomers containing thiophene, and conductive oligomers such as oligomers containing arylamine and conductive dendrimers such as dendrimers containing arylamine which are disclosed in JP-A-08-193191, can be used.

(6) Electron Injecting and Transporting Layer

Next, the electron injecting and transporting layer is a layer which helps injection of electrons into the light emitting layer, transports the electrons to the light emitting region, and exhibits a great mobility of electrons. The adhesion improving layer is an electron injecting layer including a material exhibiting particularly improved adhesion with the cathode.

In addition, it is known that, in an organic EL device, emitted light is reflected by an electrode (cathode in this case), so emitted light directly extracted from an anode and emitted light extracted via the reflection by the electrode interfere with each other. The thickness of an electron transporting layer is appropriately selected from the range of several nanometers to several micrometers in order that the interference effect may be effectively utilized. When the thickness is particularly large, an electron mobility is preferably at least $10^{-5}$ m$^2$/Vs or more upon application of an electric field of $10^4$ to $10^6$ V/cm in order to avoid an increase in voltage.

A metal complex of 8-hydroxyquinoline or of a derivative of 8-hydroxyquinoline, or an oxadiazole derivative is suitable as a material to be used in an electron injecting layer. Specific examples of the metal complex of 8-hydroxyquinoline or of a derivative of 8-hydroxyquinoline that can be used as an electron injecting material include metal chelate oxynoid compounds each containing a chelate of oxine (generally 8-quinolinol or 8-hydroxyquinoline) such as tris(8-quinolinolato) aluminum.

On the other hand, examples of the oxadiazole derivative include electron transfer compounds represented by the following general formulae:

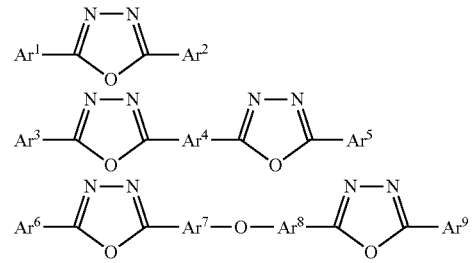

where: $Ar^1$, $Ar^2$, $Ar^3$, $Ar^5$, $Ar^6$ and $Ar^9$ each represent a substituted or unsubstituted aryl group and may represent the same group or different groups. $Ar^4$, $Ar^7$ and $Ar^8$ each represent a substituted or unsubstituted arylene group and may represent the same group or different groups.

Examples of the aryl group include a phenyl group, a biphenyl group, an anthranyl group, a perylenyl group, and a pyrenyl group. Examples of the arylene group include a phenylene group, a naphthylene group, a biphenylene group, an anthranylene group, a perylenylene group, and a pyrenylene group. Examples of the substituent include alkyl groups each having 1 to 10 carbon atoms, alkoxyl groups each having 1 to 10 carbon atoms, and a cyano group. As the electron transfer compound, compounds which can form thin films are preferable.

Examples of the electron transfer compounds described above include the following.

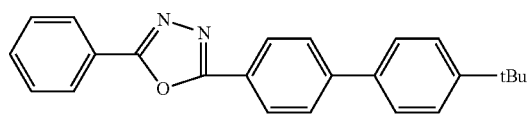

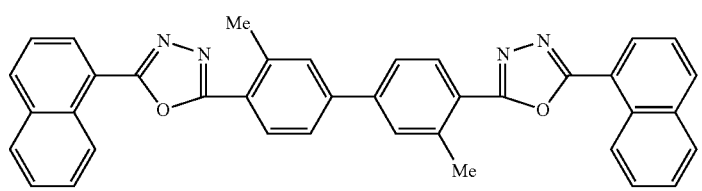

-continued

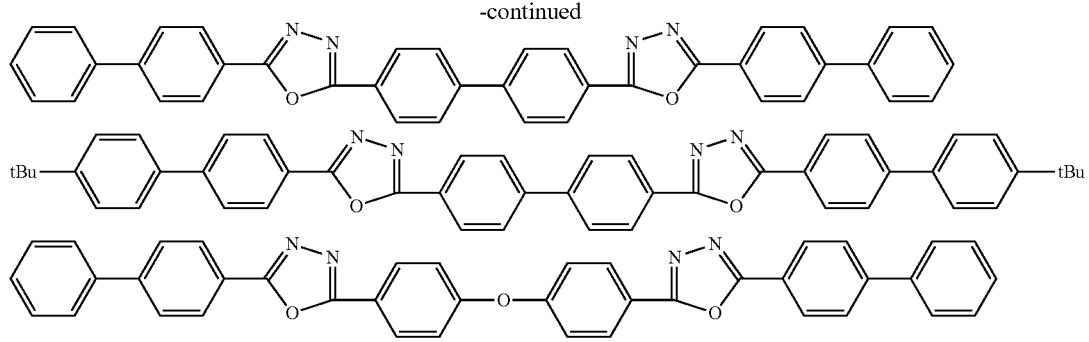

Further, materials represented by the following general formulae (A) to (E) can be used in an electron injecting layer and an electron transporting layer.

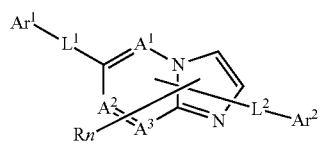
(A)

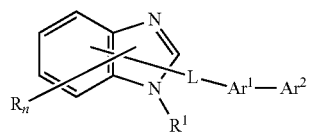
(B)

Nitrogen-containing heterocyclic derivatives represented by the general formulae (A) and (B)

In the general formulae (A) and (B), $A^1$ to $A^3$ each independently represent a nitrogen atom or a carbon atom, $Ar^1$ represents a substituted or unsubstituted aryl group having 6 to 60 ring carbon atoms, or a substituted or unsubstituted heteroaryl group having 3 to 60 ring carbon atoms, $Ar^2$ represents a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, or a substituted or unsubstituted alkoxy group having 1 to 20 carbon atoms, or a divalent group of any one of them provided that one of $Ar^1$ and $Ar^2$ represents a substituted or unsubstituted fused ring group having 10 to 60 ring carbon atoms or a substituted or unsubstituted monohetero fused ring group having 3 to 60 ring carbon atoms, $L^1$, $L^2$, and L each independently represent a single bond, a substituted or unsubstituted arylene group having to 60 ring carbon atoms, a substituted or unsubstituted heteroarylene group having 3 to 60 ring carbon atoms, or a substituted or unsubstituted fluorenylene group, R represents a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, or a substituted or unsubstituted alkoxy group having 1 to 20 carbon atoms. n represents an integer of 0 to 5, and, when n represents 2 or more, multiple R's may be identical to or different from each other, and multiple R groups adjacent to each other may be bonded to each other to form a carbocyclic aliphatic ring or a carbocyclic aromatic ring.)

A nitrogen-containing heterocyclic ring derivative represented by the general formula (C):

$$HAr\text{-}L\text{-}Ar^1\text{---}Ar^2 \quad (C)$$

In the formula, HAr represents a nitrogen-containing heterocyclic ring which has 3 to 40 carbon atoms and may have a substituent, L represents a single bond, an arylene group which has 6 to 60 carbon atoms and may have a substituent, a heteroarylene group which has 3 to 60 carbon atoms and may have a substituent, or a fluorenylene group which may have a substituent, $Ar^1$ represents a divalent aromatic hydrocarbon group which has 6 to 60 carbon atoms and may have a substituent, and $Ar^2$ represents an aryl group which has 6 to 60 carbon atoms and may have a substituent, or a heteroaryl group which has 3 to 60 carbon atoms and may have a substituent.

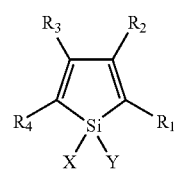
(D)

A silacyclopentadiene derivative represented by the general formula (D):
where; X and Y each independently represent a saturated or unsaturated hydrocarbon group having 1 to 6 carbon atoms, an alkoxy group, an alkenyloxy group, an alkynyloxy group, a hydroxy group, a substituted or unsubstituted aryl group, or a substituted or unsubstituted heterocycle, or X and Y are bonded to each other to form a structure as a saturated or unsaturated ring; and $R_1$ to $R_4$ each independently represent hydrogen, a halogen atom, a substituted or unsubstituted alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group, or, when two or more of $R_1$ to $R_4$ are adjacent to each other, they form a structure in which a substituted or unsubstituted ring is condensed.

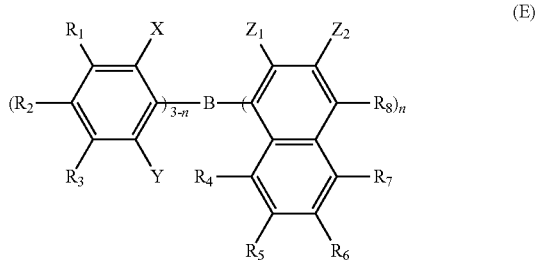

(E)

A borane derivative represented by the general formula (E):
where; $R_1$ to $R_8$ and $Z_2$ each independently represent a hydrogen atom, a saturated or unsaturated hydrocarbon group, an aromatic group, a heterocyclic group, a substituted amino group, a substituted boryl group, an alkoxy group, or an aryloxy group; X, Y, and $Z_1$ each independently represent a saturated or unsaturated hydrocarbon group, an aromatic group, a heterocyclic group, a substituted amino group, an alkoxy group, or an aryloxy group; substituents of $Z_1$ and $Z_2$ may be bonded to each other to form a fused ring; and n represents an integer of 1 to 3, and, when n represents 2 or more, $Z_1$'s may be different from each other provided that the case where n represents 1, X, Y, and $R_2$ each represent a methyl group, $R_8$ represents a hydrogen atom or a substituted boryl group and the case where n represents and $Z_1$'s each represent a methyl group are excluded.

(F)

In the equation (F): $Q^1$ and $Q^2$ each independently represent a ligand represented by the following general formula (G); and L represents a halogen atom, a substituted or unsubstituted alkyl group, a substituted or unsubstituted cycloalkyl group, a substituted or unsubstituted aryl group, a substituted or unsubstituted heterocyclic group, —$OR^1$ where $R^1$ represents a hydrogen atom, a substituted or unsubstituted alkyl group, a substituted or unsubstituted cycloalkyl group, a substituted or unsubstituted aryl group, or a substituted or unsubstituted heterocyclic group, or a ligand represented by —O—Ga-$Q^3$ ($Q^4$) where $Q^3$ and $Q^4$ are identical to $Q^1$ and $Q^2$, respectively.)

(G)

In the equation (G): the rings $A^1$ and $A^2$ are six-membered aryl ring structures which are condensed with each other and each of which may have a substituent.

The metal complex behaves strongly as an n-type semiconductor, and has a large electron injecting ability. Further, generation energy upon formation of the complex is low. As a result, the metal and the ligand of the formed metal complex are bonded to each other so strongly that the fluorescent quantum efficiency of the complex as a light emitting material improves.

Specific examples of a substituent in the rings $A^1$ and $A^2$ which each form a ligand in the general formula (G) include: a halogen atom such as chlorine, bromine, iodine, or fluorine; a substituted or unsubstituted alkyl group such as a methyl group, an ethyl group, a propyl group, a butyl group, an s-butyl group, a t-butyl group, a pentyl group, a hexyl group, a heptyl group, an octyl group, a stearyl group, or trichloromethyl group; a substituted or unsubstituted aryl group such as a phenyl group, a naphthyl group, a 3-methylphenyl group, a 3-methoxyphenyl group, a 3-fluorophenyl group, a 3-trichloromethylphenyl group, a 3-trifluoromethylphenyl group, or a 3-nitrophenyl group; a substituted or unsubstituted alkoxy group such as a methoxy group, an n-butoxy group, a t-butoxy group, a trichloromethoxy group, a trifluoroethoxy group, a pentafluoropropoxy group, a 2,2,3,3-tetrafluoropropoxy group, an 1,1,1,3,3,3-hexafluoro-2-propoxy group, or a 6-(perfluoroethyl)hexyloxy group; a substituted or unsubstituted aryloxy group such as a phenoxy group, a p-nitrophenoxy group, p-t-butylphenoxy group, a 3-fluorophenoxy group, a pentafluorophenyl group, or a 3-trifluoromethylphenoxy group; a substituted or unsubstituted alkylthio group such as a methylthio group, an ethylthio group, a t-butylthio group, a hexylthio group, an octylthio group, or a trifluoromethylthio group; a substituted or unsubstituted arylthio group such as a phenylthio group, a p-nitrophenylthio group, a p-t-butylphenylthio group, a 3-fluorophenylthio group, a pentafluorophenylthic group, or a 3-trifluoromethylphenylthio group; a mono-substituted or di-substituted amino group such as a cyano group, a nitro group, an amino group, a methylamino group, a dimethylamino group, an ethylamino group, a diethylamino group, a dipropylamino group, a dibutylamino group, or a diphenylamino group; an acylamino group such as a bis(acetoxymethyl)amino group, a bis(acetoxyethyl)amino group, a bis(acetoxypropyl)amino group, or a bis (acetoxybutyl)amino group; a hydroxyl group; a siloxy group; an acyl group; a carbamoyl group such as a methylcarbamoyl group, a dimethylcarbamoyl group, an ethylcarbamoyl group, a diethylcarbamoyl group, a propylcarbamoyl group, a butylcarbamoyl group, or a phenylcarbamoyl group; a cycloalkyl group such as a carboxylic acid group, a sulfonic acid group, an imide group, a cyclopentane group, or a cyclohexyl group; an aryl group such as a phenyl group, a naphthyl group, a biphenyl group, an anthranyl group, a phenanthryl group, a fluorenyl group, or a pyrenyl group; and a heterocyclic group such as a pyridinyl group, a pyrazinyl group, a pyrimidinyl group, a pyridazinyl group, a triazinyl group, an indolinyl group, a quinolinyl group, an acridinyl group, a pyrrolidinyl group, a dioxanyl group, a piperidinyl group, a morpholidinyl group, a piperazinyl group, a triathinyl group, a carbazolyl group, a furanyl group, a thiophenyl group, an oxazolyl group, an oxadiazolyl group, a benzoxazolyl group, a thiazolyl group, a thiadiazolyl group, a benzothiazolyl group, a triazolyl group, an imidazolyl group, a benzoimidazolyl group, or a puranyl group. In addition, the above-mentioned substituents may be bound to each other to further form a six-membered aryl ring or a heterocycle.

A preferable embodiment of the organic EL device of the present invention includes an element including a reducing dopant in the region of electron transport or in the interfacial region of the cathode and the organic thin film layer. The reducing dopant is defined as a substance which can reduce a compound having the electron-transporting property. Various compounds can be used as the reducing dopant as long as the compounds have a uniform reductive property. For example, at least one substance selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, organic complexes of alkali metals, organic complexes of alkaline earth metals, and organic complexes of rare earth metals can be preferably used.

More specifically, examples of the reducing dopant include substances having a work function of 2.9 eV or smaller, specific examples of which include at least one alkali metal selected from the group consisting of Na (the work function: 2.36 eV), K (the work function: 2.28 eV), Rb (the work function: 2.16 eV), and Cs (the work function: 1.95 eV) and at least one alkaline earth metal selected from the group consisting of Ca (the work function: 2.9 eV), Sr (the work function: 2.0 to 2.5 eV), and Ba (the work function: 2.52 eV). Among the above-mentioned substances, at least one alkali metal selected from the group consisting of K, Rb, and Cs is more preferable, Rb and Cs are still more preferable, and Cs is most preferable as the reducing dopant. Those alkali metals have great reducing ability, and the luminance of the emitted light and the life time of the organic EL device can be increased by addition of a relatively small amount of the alkali metal into the electron injecting zone. As the reducing dopant having a work function of 2.9 eV or smaller, combinations of two or more alkali metals thereof are also preferable. Combinations having Cs such as the combinations of Cs and Na, Cs and K, Cs and Rb, and Cs, Na, and K are more preferable. The reducing ability can be efficiently exhibited by the combination having Cs. The luminance of emitted light and the life time of the organic EL device can be increased by adding the combination having Cs into the electron injecting zone.

The present invention may further include an electron injecting layer which is composed of an insulating material or a semiconductor and disposed between the cathode and the organic layer. At this time, leak of electric current can be effectively prevented by the electron injecting layer and the electron injecting property can be improved. As the insulating material, at least one metal compound selected from the group consisting of alkali metal chalcogenides, alkaline earth metal chalcogenides, alkali metal halides, and alkaline earth metal halides is preferable. It is preferable that the electron injecting layer be composed of the above-mentioned substance such as the alkali metal chalcogenide since the electron injecting property can be further improved. Preferable examples of the alkali metal chalcogenide include $Li_2O$, $K_2O$, $Na_2S$, $Na_2Se$, and $Na_2O$. To be specific, preferable examples of the alkaline earth metal chalcogenide include CaO, BaO, SrO, BeO, BaS, and CaSe. Preferable examples of the alkali metal halide include LiF, NaF, KF, LiCl, KCl, and NaCl. Preferable examples of the alkaline earth metal halide include fluorides such as $CaF_2$, $BaF_2$, $SrF_2$, $MgF_2$, and $BeF_2$ and halides other than the fluorides.

Examples of the semiconductor composing the electron-transporting layer include oxides, nitrides, and oxide nitrides of at least one element selected from Ba, Ca, Sr, Yb, Al, Ga, In, Li, Na, Cd, Mg, Si, Ta, Sb, and Zn used alone or in combination of two or more. It is preferable that the inorganic compound composing the electron-transporting layer forms a crystallite or amorphous insulating thin film. When the electron injecting layer is composed of the insulating thin film described above, a more uniform thin film can be formed, and defects of pixels such as dark spots can be decreased. Examples of the inorganic compound include alkali metal chalcogenides, alkaline earth metal chalcogenides, alkali metal halides, and alkaline earth metal halides which are described above.

(7) Cathode

As the cathode, a material such as a metal, an alloy, a conductive compound, or a mixture of those materials which has a small work function (4 eV or smaller) is used because the cathode is used for injecting electrons to the electron injecting and transporting layer or the light emitting layer. Specific examples of the electrode material include sodium, sodium-potassium alloys, magnesium, lithium, magnesium-silver alloys, aluminum/aluminum oxide, aluminum-lithium alloys, indium, and rare earth metals.

The cathode can be prepared by forming a thin film of the electrode material described above in accordance with a process such as the vapor deposition process and the sputtering process.

When the light emitted from the light emitting layer is obtained through the cathode, it is preferable that the cathode have a transmittance of the emitted light greater than 10%.

It is also preferable that the sheet resistivity of the cathode be several hundred $\Omega/\square$ or smaller. The thickness of the cathode is, in general, selected in the range of 10 nm to 1 μm and preferably in the range of 50 to 200 nm.

(8) Insulating Layer

Defects in pixels tend to be formed in organic EL device due to leak and short circuit since an electric field is applied to ultra-thin films. To prevent the formation of the defects, a layer of a thin film having an insulating property is preferably inserted between the pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. Mixtures and laminates of the above-mentioned compounds may also be used.

(9) Method of Producing the Organic EL Device

To prepare the organic EL device of the present invention, the anode and the light emitting layer, and, where necessary, the hole injecting and the transporting layer and the electron injecting and transporting layer are formed in accordance with the illustrated process using the illustrated materials, and the cathode is formed in the last step. The organic EL device may also be prepared by forming the above-mentioned layers in the order reverse to that described above, i.e., the cathode being formed in the first step and the anode in the last step.

Hereinafter, an embodiment of the process for preparing an organic EL device having a construction in which an anode, a hole injecting layer, a light emitting layer, an electron injecting layer, and a cathode are disposed successively on a substrate transmitting light will be described.

On a suitable transparent substrate, a thin film made of a material for the anode is formed in accordance with the vapor deposition process or the sputtering process so that the thickness of the formed thin film is 1 μm or smaller and preferably in the range of 10 to 200 nm. The formed thin film is used as the anode. Then, a hole injecting layer is formed on the anode. The hole injecting layer can be formed in accordance with the vacuum vapor deposition process, the spin coating process, the casting process, or the LB process, as described above. The vacuum vapor deposition process is preferable since a uniform film can be easily obtained and the possibility of formation of pin holes is small. When the hole injecting layer is formed in accordance with the vacuum vapor deposition process, in general, it is preferable that the conditions be suitably selected in the following ranges: the temperature of the source of the deposition: 50 to 450° C.; the vacuum: $10^{-7}$ to $10^{-3}$ Torr; the rate of deposition: 0.01 to 50 nm/second; the temperature of the substrate: −50 to 300° C. and the thickness of the film: 5 nm to 5 μm; although the conditions of the vacuum vapor deposition are different depending on the compound to be used (i.e., the material for the hole injecting layer) and the crystal structure and the recombination structure of the target hole injecting layer.

Then, the light emitting layer is formed on the hole injecting layer formed above. A thin film of the organic light emitting material can be formed by using a desired organic light emitting material in accordance with a process such as the vacuum vapor deposition process, the sputtering process, the spin coating process, or the casting process, and the formed thin film is used as the light emitting layer. The vacuum vapor deposition process is preferable since a uniform film can be easily obtained and the possibility of formation of pin holes is small. When the light emitting layer is formed in accordance with the vacuum vapor deposition process, in general, the conditions of the vacuum vapor deposition process can be selected in the same ranges as those described for the vacuum vapor deposition of the hole injecting layer, although the conditions are different depending on the used compound.

Next, an electron injecting layer is formed on the light emitting layer formed above. Similarly to the hole injecting layer and the light emitting layer, it is preferable that the electron injecting layer be formed in accordance with the vacuum vapor deposition process since a uniform film must be obtained. The conditions of the vacuum vapor deposition can be selected in the same ranges as those described for the vacuum vapor deposition of the hole injecting layer and the light emitting layer.

When the vapor deposition process is used, the aromatic amine derivative of the present invention can be deposited by vapor in combination with other materials, although the situation may be different depending on which layer in the light emitting zone or in the hole transporting zone includes the compound. When the spin coating process is used, the compound can be incorporated into the formed layer by using a mixture of the compound with other materials.

A cathode is formed on the electron injecting layer formed above in the last step, and an organic EL device can be obtained.

The cathode is made of a metal and can be formed in accordance with the vacuum vapor deposition process or the sputtering process. It is preferable that the vacuum vapor deposition process be used in order to prevent formation of damages on the lower organic layers during the formation of the film.

In the above-mentioned preparation of the organic EL device, it is preferable that the above-mentioned layers from the anode to the cathode be formed successively while the preparation system is kept in a vacuum after being evacuated once.

The method of forming the layers in the organic EL device of the present invention is not particularly limited. A conventionally known process such as the vacuum vapor deposition process or the spin coating process can be used. The organic thin film layer which is used in the organic EL device of the present invention and includes the compound represented by general formula (1) described above can be formed in accordance with a known process such as the vacuum vapor deposition process or the molecular beam epitaxy process (the MBE process) or, using a solution prepared by dissolving the compounds into a solvent, in accordance with a coating process such as the dipping process, the spin coating process, the casting process, the bar coating process, or the roll coating process.

The thickness of each layer in the organic thin film layer in the organic EL device of the present invention is not particularly limited. In general, an excessively thin layer tends to have defects such as pin holes, and an excessively thick layer requires a high applied voltage to decrease the efficiency. Therefore, a thickness in the range of several nanometers to 1 μm is preferable.

The organic EL device which can be prepared as described above emits light when a direct voltage of 5 to 40 V is applied in the condition that the polarity of the anode is positive (+) and the polarity of the cathode is negative (−). When the polarity is reversed, no electric current is observed and no light is emitted at all. When an alternating voltage is applied to the organic EL device, the uniform light emission is observed only in the condition that the polarity of the anode is positive and the polarity of the cathode is negative. When an alternating voltage is applied to the organic EL device, any type of wave shape can be used.

EXAMPLES

Hereinafter, the present invention will be described in more detail on the basis of synthesis examples and examples.

Synthesis Example 1

Synthesis of Intermediate 1

20.0 g of 4-bromobiphenyl (manufactured by TOKYO CHEMICAL INDUSTRY CO., LTD.), 8.64 g of sodium t-butoxide (manufactured by Wako Pure Chemical Industries, Ltd.), and 84 mg of palladium acetate (manufactured by Wako Pure Chemical Industries, Ltd.) were loaded into a 200-mL three-necked flask. Further, a stirring rod was placed in the flask, and rubber caps were set on both side ports of the flask. A reflux condenser was inserted into the central port of the flask, and a three-way cock and a balloon in which an argon gas was sealed were set above the condenser. The inside of the system was replaced with the argon gas in the balloon three times by using a vacuum pump.

Next, 120 mL of dehydrated toluene (manufactured by HIROSHIMA WAKO CO., LTD.), 4.08 mL of benzylamine (manufactured by TOKYO CHEMICAL INDUSTRY CO., LTD.), and 338 μl, of tri-t-butylphosphine (manufactured by SIGMA-ALDRICH, 2.22-mol/L toluene solution) were added to the flask by using a syringe through a rubber septum, and the whole was stirred for 5 minutes at room temperature.

Next, the flask was set in an oil bath, and was gradually heated to 120° C. while the solution was stirred. At 7 hours after that, the flask was lifted off the oil bath so that the reaction would be completed. The flask was left under an argon atmosphere for 12 hours.

The reaction solution was transferred to a separating funnel, and 600 mL of dichloromethane were added to dissolve the precipitate. After the resultant had been washed with 120 mL of a saturated salt solution, an organic layer was dried with anhydrous potassium carbonate. The solvent of the organic layer obtained by separating potassium carbonate by filtration was removed by distillation. 400 mL of toluene and 80 mL of ethanol were added to the resultant residue. A drying pipe was attached to heat the resultant to 80° C. so that the residue would be completely dissolved. After that, the resultant was left for 12 hours, and was slowly cooled to room temperature for recrystallization.

The precipitated crystal was separated by filtration, and was dried in a vacuum at 60° C., whereby 13.5 g of N,N-di-(4-biphenylyl)benzylamine were obtained.

1.35 g of N,N-di-(4-biphenylyl)benzylamine and 135 mg of palladium-activated carbon (manufactured by HIROSHIMA WAKO CO., LTD., palladium content 10 wt %) were loaded into a 300-mL one-necked flask, and 100 mL of chloroform and 20 mL of ethanol were added to dissolve the mixture.

Next, a stirring rod was placed in the flask. After that, a three-way cock mounted with a balloon filled with 2 L of a hydrogen gas was attached to the flask, and the inside of the flask system was replaced with the hydrogen gas ten times by using a vacuum pump. The balloon was newly filled with a hydrogen gas in an amount corresponding to the reduced amount so that the volume of the hydrogen gas would be 2 L again. After that, the solution was vigorously stirred at room temperature for 30 hours. After that, 100 mL of dichloromethane were added to the resultant, and the catalyst was separated by filtration.

Next, the resultant solution was transferred to a separating funnel, and was washed with 50 mL of a saturated aqueous solution of sodium hydrogencarbonate. After that, an organic layer was fractionated and dried with anhydrous potassium carbonate. After the resultant had been filtrated, the solvent was removed by distillation, and 50 mL of toluene were added to the resultant residue for recrystallization. The precipitated crystal was separated by filtration, and was dried in a vacuum at 50° C., whereby 0.99 g of di-4-biphenylylamine (Intermediate 1) shown below was obtained.

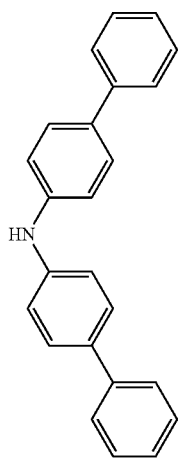

Intermediate 1

Synthesis Example 2

Synthesis of Intermediate 2

In a stream of argon, 10 g of di-4-biphenylylamine, 9.7 g of 4,4'-dibromobiphenyl (manufactured by TOKYO CHEMICAL INDUSTRY CO., LTD.), 3 g of sodium t-butoxide (manufactured by HIROSHIMA WAKO CO., LTD.), 0.5 g of bis(triphenylphosphine)palladium(II) chloride (manufactured by TOKYO CHEMICAL INDUSTRY CO., LTD.), and 500 mL of xylene were loaded, and the whole was subjected to a reaction at 130° C. for 24 hours.

After the resultant had been cooled, 1,000 mL of water were added to the resultant, and the mixture was subjected to Celite filtration. The filtrate was extracted with toluene and dried with anhydrous magnesium sulfate. The dried product was condensed under reduced pressure, and the resultant crude product was subjected to column purification. The purified product was recrystallized with toluene. The crystal was taken by filtration, and was then dried, whereby 4.6 g of 4'-bromo-N,N-dibiphenylyl-4-amino-1,1'-biphenyl (Intermediate 2) shown below were obtained.

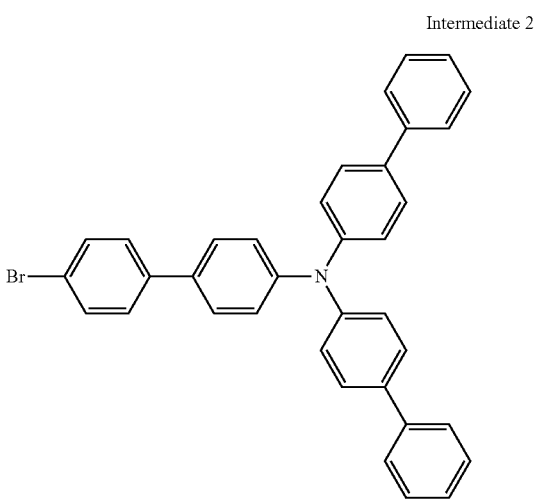 [SMILES: Brc1ccc(-c2ccc(N(c3ccc(-c4ccccc4)cc3)c3ccc(-c4ccccc4)cc3)cc2)cc1]

Intermediate 2

Synthesis Example 3

Synthesis of Intermediate 3

In a stream of argon, 6.8 g of N-phenyl-1-naphthylamine (manufactured by TOKYO CHEMICAL INDUSTRY CO., LTD.), 9.7 g of 4,4'-dibromobiphenyl (manufactured by TOKYO CHEMICAL INDUSTRY CO., LTD.), 3 g of t-butoxy sodium (manufactured by HIROSHIMA WAKO CO., LTD.), 0.5 g of bis(triphenylphosphine)palladium (II) chloride (manufactured by TOKYO CHEMICAL INDUSTRY CO., LTD.), and 500 mL of xylene were loaded, and the whole was subjected to a reaction at 130° C. for 24 hours.

After the resultant had been cooled, 1,000 mL of water were added to the resultant, and the mixture was subjected to Celite filtration. The filtrate was extracted with toluene and dried with anhydrous magnesium sulfate. The dried product was condensed under reduced pressure, and the resultant crude product was subjected to column purification. The purified product was recrystallized with toluene. The crystal was taken by filtration, and was then dried, whereby 4.1 g of 4'-bromo-N-phenyl-N-1-naphthyl-amino-1,1'-biphenyl (Intermediate 3) shown below were obtained.

Intermediate 3

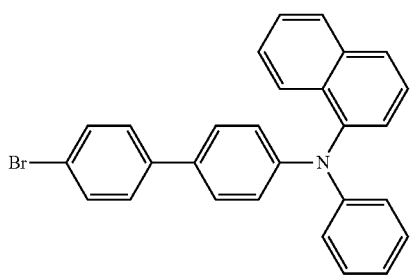

Synthesis Example 4

Synthesis of Intermediate 4 and Intermediate 5

250 g of m-terphenyl (manufactured by SIGMA-ALD-RICH), 50 g of hydroiodic acid dihydrate, 75 g of iodine, 750 mL of acetic acid, and 25 mL of concentrated sulfuric acid were loaded into a three-necked flask, and the whole was subjected to a reaction at 70° C. for 3 hours. After the reaction, the resultant was injected into 5 L of methanol, and then the whole was stirred for 1 hour. The resultant crystal taken by the filtration of the mixture was purified by means of column chromatography and recrystallized with acetonitrile, whereby 64 g of 5-phenyl-3-iodobiphenyl (Intermediate 4) shown below and 17 g of 3'-phenyl-4-iodobiphenyl (Intermediate 5) shown below were obtained.

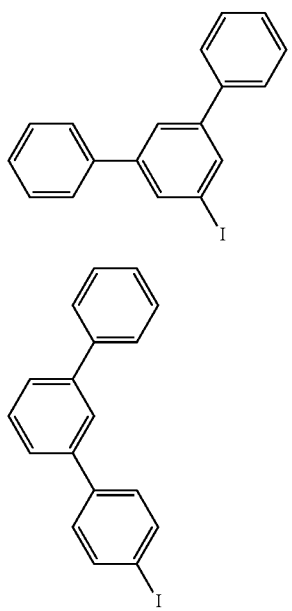

Intermediate 4

Intermediate 5

Synthesis Example 5

Synthesis of Intermediate 6

Under an argon atmosphere, 50 g of 2-bromofluorene (manufactured by TOKYO CHEMICAL INDUSTRY CO., LTD.), 100 mL of dimethylsulfoxide (DMSO), 0.95 g of benzyl triethylammonium chloride (manufactured by HIROSHIMA WAKO CO., LTD.), and 65 g of a 50-wt % aqueous solution of sodium hydroxide were loaded into a 1,000-mL three-necked flask.

The reaction vessel was placed in a water bath, and 44 g of 1,5-dibromopentane (manufactured by HIROSHIMA WAKO CO., LTD.) were added to the mixture while the mixture was stirred.

After a reaction for 5 hours, 1,000 mL of water were added to the resultant, and the whole was extracted with 500 mL of toluene. An organic layer was dried with magnesium sulfate, and the solvent was removed by distillation with a rotary evaporator, whereby 56 g of Intermediate 6 shown below as oil were obtained.

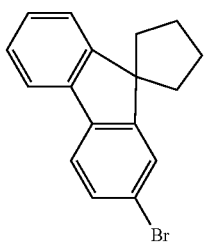

Intermediate 6

Synthesis Example 6

Synthesis of Intermediate 7

A reaction was performed in the same manner as in Synthesis Example 5 except that 47 g of 1,6-dibromohexane (manufactured by HIROSHIMA WAKO CO., LTD.) were used instead of 1,5-dibromopentane. As a result, 49 g of Intermediate 7 shown below as oil were obtained.

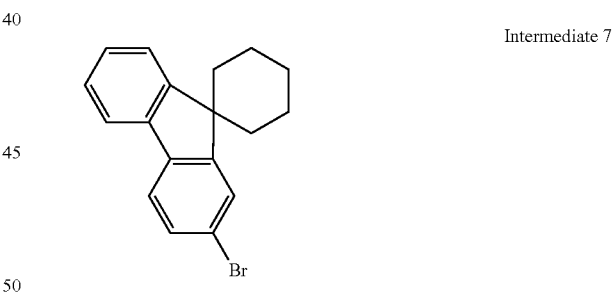

Intermediate 7

Synthesis Example 7

Synthesis of Intermediate 8

In a stream of argon, 5.7 g of benzamide (manufactured by TOKYO CHEMICAL INDUSTRY CO., LTD.), 10 g of 4-bromobiphenyl (manufactured by TOKYO CHEMICAL INDUSTRY CO., LTD.), 0.82 g of copper (I) iodide (manufactured by HIROSHIMA WAKO CO., LTD.), 0.76 g of N,N'-dimethylethylenediamine (manufactured by SIGMA-ALDRICH), 11.8 g of potassium carbonate (manufactured by HIROSHIMA WAKO CO., LTD.), and 60 mL of xylene were loaded into a 200-mL three-necked flask, and the whole was subjected to a reaction at 130° C. for 36 hours.

After having been cooled, the resultant was filtrated and washed with toluene. Further, the resultant was washed with water and methanol. After that, the resultant was dried, whereby 10.5 g of Intermediate 8 shown below as a pale yellow powder were obtained.

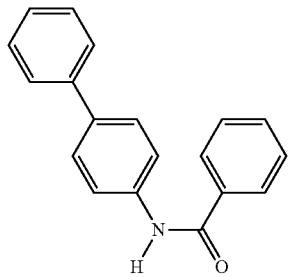

Intermediate 8

Synthesis Example 8

Synthesis of Intermediate 9

In a stream of argon, 11.1 g of 1-acetamidenaphthalene (manufactured by TOKYO CHEMICAL INDUSTRY CO., LTD.), 15.4 g of 4-bromobiphenyl (manufactured by TOKYO CHEMICAL INDUSTRY CO., LTD.), 1.14 g of copper(I) iodide (manufactured by HIROSHIMA WAKO CO., LTD.), 1.06 g of N,N'-dimethylethylenediamine (manufactured by SIGMA-ALDRICH), 20.0 g of potassium carbonate (manufactured by HIROSHIMA WAKO CO., LTD.), and 100 mL of xylene were loaded into a 300-mL three-necked flask, and the whole was subjected to a reaction at 130° C. for 36 hours.

After having been cooled, the resultant was filtrated and washed with toluene. Further, the resultant was washed with water and methanol. After that, the resultant was dried, whereby 15.0 g of a pale yellow powder were obtained.

15.0 g of the above-mentioned powder, 17.6 g of potassium hydroxide (manufactured by HIROSHIMA WAKO CO., LTD.), 15 mL of ion-exchanged water, 20 mL of xylene (manufactured by HIROSHIMA WAKO CO., LTD.), and 10 mL of ethanol (manufactured by HIROSHIMA WAKO CO., LTD.) were loaded into a 300-mL three-necked flask, and the whole was refluxed for 36 hours. After the completion of the reaction, the resultant was extracted with toluene and dried with magnesium sulfate. The dried product was condensed under reduced pressure, and the resultant crude product was subjected to column purification. The purified product was recrystallized with toluene. The crystal was taken by filtration, and was then dried, whereby 11.2 g of Intermediate 9 shown below as a white powder were obtained.

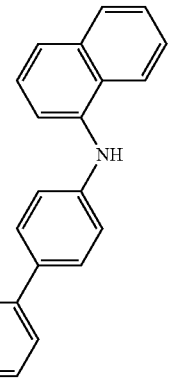

Intermediate 9

Synthesis Example 9

Synthesis of Intermediate 10

A reaction was performed in the same manner as in Synthesis Example 8 except that 25.6 g of Intermediate 4 were used instead of 15.4 g of 4-bromobiphenyl (manufactured by TOKYO CHEMICAL INDUSTRY CO., LTD.). As a result, 11.3 g of Intermediate 10 shown below as a white powder were obtained.

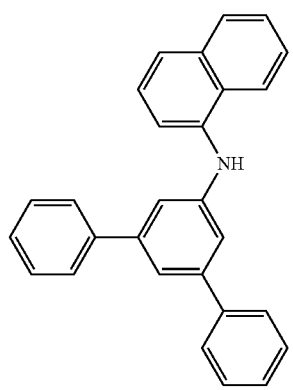

Intermediate 10

Synthesis Example 10

Synthesis of Intermediate 11

A reaction was performed in the same manner as in Synthesis Example 8 except that 25.6 g of Intermediate 5 were used instead of 15.4 g of 4-bromobiphenyl (manufactured by TOKYO CHEMICAL INDUSTRY CO., LTD.). As a result, 10.6 g of Intermediate 11 shown below as a white powder were obtained.

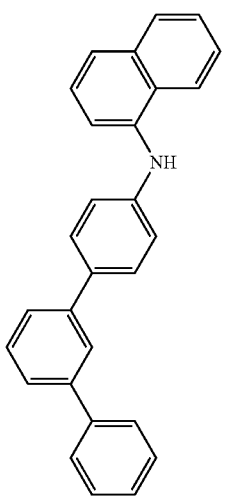

Intermediate 11

Synthesis Example 11

Synthesis of Intermediate 12

A reaction was performed in the same manner as in Synthesis Example 8 except that 20.6 g of Intermediate 7 were used instead of 15.4 g of 4-bromobiphenyl (manufactured by TOKYO CHEMICAL INDUSTRY CO., LTD.). As a result, 11.9 g of Intermediate 12 shown below as a white powder were obtained.

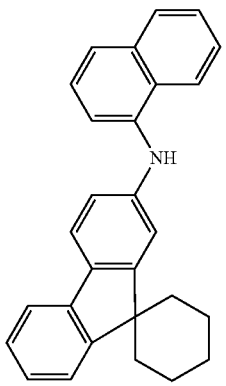

Intermediate 12

Synthesis Example 12

Synthesis of Intermediate 13

In a stream of argon, 16.4 g of Intermediate 8, 17.0 g of 9-bromophenanthrene (manufactured by TOKYO CHEMICAL INDUSTRY CO., LTD.), 1.14 g of copper(I) iodide (manufactured by HIROSHIMA WAKO CO., LTD.), 1.06 g of N,N'-dimethylethylenediamine (manufactured by SIGMA-ALDRICH), 20.0 g of potassium carbonate (manufactured by HIROSHIMA WAKO CO., LTD.), and 100 mL of xylene were loaded into a 300-mL three-necked flask, and the whole was subjected to a reaction at 130° C. for 36 hours.

After having been cooled, the resultant was filtrated and washed with toluene. Further, the resultant was washed with water and methanol. After that, the resultant was dried, whereby 14.0 g of a pale yellow powder were obtained.

14.0 g of the above-mentioned powder, 15.1 g of potassium hydroxide (manufactured by HIROSHIMA WAKO CO., LTD.), 13 mL of ion-exchanged water, 17 mL of xylene (manufactured by HIROSHIMA WAKO CO., LTD.), and 9 mL of ethanol (manufactured by HIROSHIMA WAKO CO., LTD.) were loaded into a 300-mL three-necked flask, and the whole was refluxed for 36 hours. After the completion of the reaction, the resultant was extracted with toluene and dried with magnesium sulfate. The dried product was condensed under reduced pressure, and the resultant crude product was subjected to column purification. The purified product was recrystallized with toluene. The crystal was taken by filtration, and was then dried, whereby 9.3 g of Intermediate 13 shown below as a white powder were obtained.

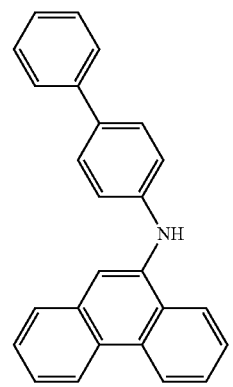

Intermediate 13

Synthesis Example 13

Synthesis of Intermediate 14

A reaction was performed in the same manner as in Synthesis Example 12 except that 20.7 g of Intermediate 4 were used instead of 17.0 g of 9-bromophenanthrene (manufactured by TOKYO CHEMICAL INDUSTRY CO., LTD.). As a result, 15.1 g of Intermediate 14 shown below as a white powder were obtained.

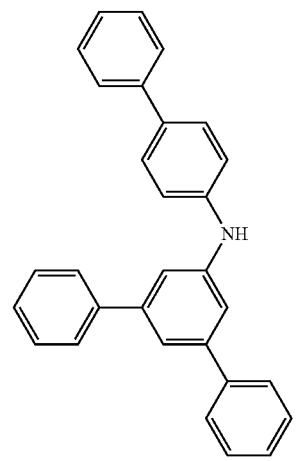

Intermediate 14

Synthesis Example 14

Synthesis of Intermediate 15

A reaction was performed in the same manner as in Synthesis Example 12 except that 20.7 g of Intermediate 5 were used instead of 17.0 g of 9-bromophenanthrene (manufactured by TOKYO CHEMICAL INDUSTRY CO., LTD.). As a result, 14.3 g of Intermediate 15 shown below as a white powder were obtained.

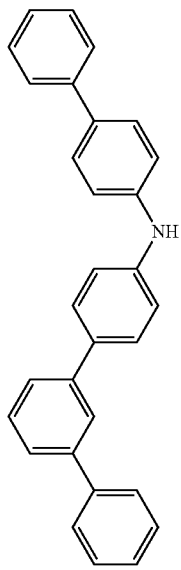

Intermediate 15

Synthesis Example 15

Synthesis of Intermediate 16

A reaction was performed in the same manner as in Synthesis Example 12 except that 20.6 g of Intermediate 7 were used instead of 17.0 g of 9-bromophenanthrene (manufactured by TOKYO CHEMICAL INDUSTRY CO., LTD.). As a result, 11.5 g of Intermediate 16 shown below as a white powder were obtained.

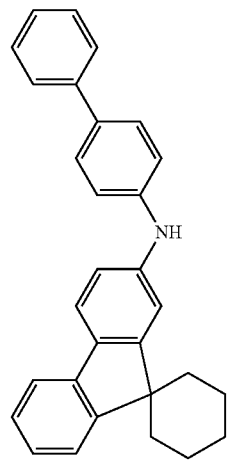

Intermediate 16

Synthesis Example 16

Synthesis of Intermediate 17

A reaction was performed in the same manner as in Synthesis Example 12 except that 19.7 g of Intermediate 6 were used instead of 17.0 g of 9-bromophenanthrene (manufactured by TOKYO CHEMICAL INDUSTRY CO., LTD.). As a result, 10.5 g of Intermediate 17 shown below as a white powder were obtained.

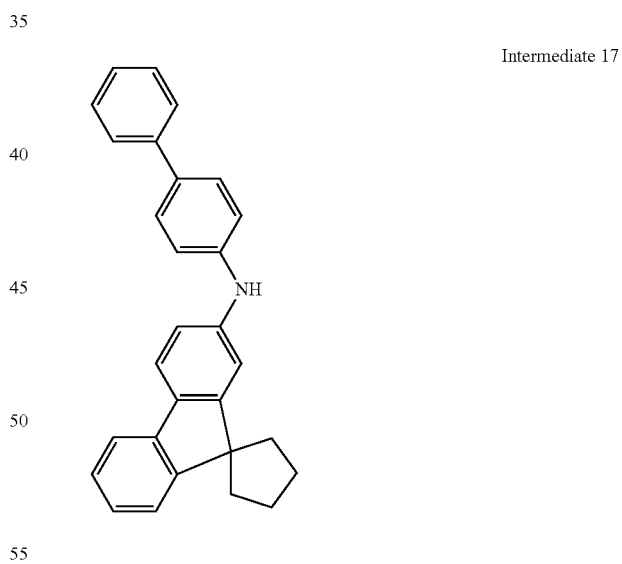

Intermediate 17

Synthesis Example 17

Synthesis of Intermediate 18

A reaction was performed in the same manner as in Synthesis Example 12 except that 18.0 g of 2-bromo-9,9-dimethylflorene were used instead of 17.0 g of 9-bromophenanthrene (manufactured by TOKYO CHEMICAL INDUSTRY CO., LTD.). As a result, 10.6 g of Intermediate 18 shown below as a white powder were obtained.

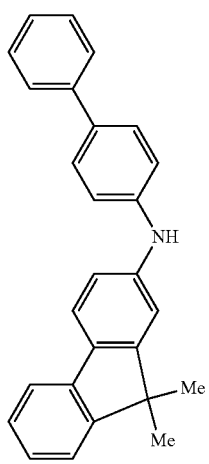

Intermediate 18

Synthesis Example 18

Synthesis of Intermediate 19

In a stream of argon, 7.2 g of benzamide (manufactured by TOKYO CHEMICAL INDUSTRY CO., LTD.), 40.8 g of Intermediate 5, 2.3 g of copper(I) iodide (manufactured by HIROSHIMA WAKO CO., LTD.), 2.1 g of N,N'-dimethylethylenediamine (manufactured by SIGMA-ALDRICH), 33.1 g of potassium carbonate (manufactured by HIROSHIMA WAKO CO., LTD.), and 100 mL of xylene were loaded into a 200-mL three-necked flask, and the whole was subjected to a reaction at 130° C. for 36 hours.

After having been cooled, the resultant was filtrated and washed with toluene. Further, the resultant was washed with water and methanol. After that, the resultant was dried, whereby 27.0 g of a pale yellow powder were obtained.

27.0 g of the above-mentioned powder, 19.0 g of potassium hydroxide (manufactured by HIROSHIMA WAKO CO., LTD.), 17 mL of ion-exchanged water, 25 mL of xylene (manufactured by HIROSHIMA WAKO CO., LTD.), and 12 mL of ethanol (manufactured by HIROSHIMA WAKO CO., LTD.) were loaded into a 300-mL three-necked flask, and the whole was refluxed for 36 hours. After the completion of the reaction, the resultant was extracted with toluene and dried with magnesium sulfate. The dried product was condensed under reduced pressure, and the resultant crude product was subjected to column purification. The purified product was recrystallized with toluene. The crystal was taken by filtration, and was then dried, whereby 18.1 g of Intermediate 19 shown below as a white powder were obtained.

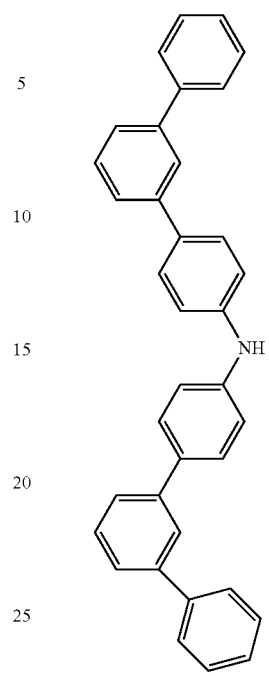

Intermediate 19

Syntheses Example 19

Syntheses of Intermediate 20

A reaction was performed in the same manner as in Synthesis Example 18 except that 41.3 g of 2-bromo-9,9-dimethylfluorene were used instead of 40.8 g of Intermediate 5. As a result, 15.3 g of Intermediate 20 shown below as a white powder were obtained.

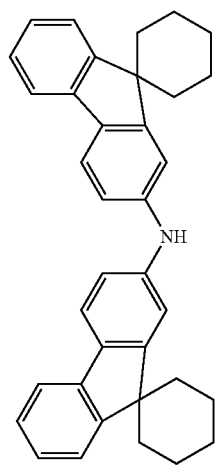

Intermediate 20

Synthesis Example 20

Synthesis of Intermediate 21

In a stream of argon, 28.6 g of 1-bromonaphthalene, 80 mL of dehydrated ether, and 80 mL of dehydrated toluene were loaded into a 500-mL three-necked flask. 110 mmol of a solution of n-butyllithium in hexane were charged into the mixture at −30° C., and the whole was subjected to a reaction at 0° C. for 1 hour. The resultant was cooled to −70° C., and 70 mL of triisopropyl borate were loaded into the resultant. The resultant was slowly heated to room temperature and stirred for 1 hour. 80 mL of 10% hydrochloric acid were added to the resultant, and the whole was extracted with ethyl acetate/water. After that, the extract was dried with anhydrous sodium sulfate. The solution was condensed and washed with hexane, whereby 17.5 g of a boric acid compound were obtained.

In a stream of argon, 17.5 g of the boric acid compound obtained in the foregoing, 11.0 g of bromobenzene, 3.8 g of tetrakis(triphenylphosphine)palladium(0), 100 mL of a 2-M Na$_2$CO$_3$ solution, and 160 mL of dimethoxyethane were loaded into a 500-mL three-necked flask, and then the whole was refluxed for 8 hours. The reaction liquid was extracted with toluene/water and dried with anhydrous sodium sulfate. The dried product was condensed under reduced pressure, and the resultant crude product was subjected to column purification, whereby 17.6 g of Intermediate 21 shown below as a white powder were obtained. FD-MS analysis resulted in 1:1 peaks at m/z=282 and 284 for C$_{16}$H$_{11}$Br=283, so the resultant powder was identified as Intermediate 21 shown below.

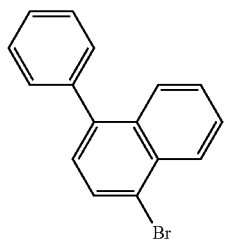

Intermediate 21

Synthesis Example 21

Synthesis of Intermediate 22

A reaction was performed in the same manner as in Synthesis Example 20 except that 20.7 g of 4-bromobiphenyl were used instead of 20.7 g of bromobenzene. As a result, 7.4 g of Intermediate 22 shown below as a white powder were obtained. FD-MS analysis resulted in 1:1 peaks at m/z=358 and 360 for C$_{22}$H$_{15}$Br=359, so the resultant powder was identified as Intermediate 22 shown below.

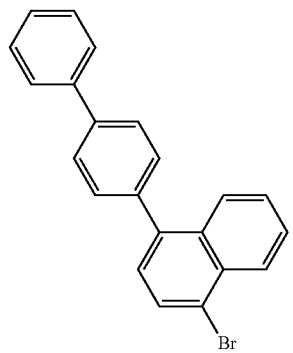

Intermediate 22

Synthesis Example 22

Synthesis of Intermediate 23

In a stream of argon, 20.7 g of 1-bromonaphthalene, 80 mL of dehydrated ether, and 80 mL of dehydrated toluene were loaded into a 500-mL three-necked flask. 120 mmol of a solution of n-butyllithium in hexane were charged into the mixture at −30° C., and the whole was subjected to a reaction at 0° C. for 1 hour. The resultant was cooled to −70° C., and 70 mL of triisopropyl borate were loaded into the resultant. The resultant was slowly heated to room temperature and stirred for 1 hour. 80 mL of 10% hydrochloric acid were added to the resultant, and the whole was extracted with ethyl acetate and water. After that, the extract was dried with anhydrous sodium sulfate. The solution was condensed and washed with hexane, whereby 9.7 g of a boric acid compound were obtained.

In a stream of argon, 9.7 g of the boric acid compound obtained in the foregoing, 13.3 g of 4-iodobromobenzene, 1.9 g of tetrakis(triphenylphosphine) palladium (O), 50 mL of a 2-M sodium carbonate solution, and 80 mL of dimethoxyethane were loaded into a 500-mL three-necked flask, and then the whole was refluxed for 8 hours. The reaction liquid was extracted with toluene/water and dried with anhydrous sodium sulfate. The dried product was condensed under reduced pressure, and the resultant crude product was subjected to column purification, whereby 8.8 g of Intermediate 23 shown below as a white powder were obtained. FD-MS analysis resulted in 1:1 peaks at m/z=282 and 284 for C$_{16}$H$_{11}$Br=283, so the resultant powder was identified as Intermediate 23 shown below.

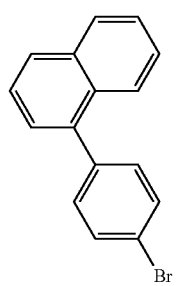

Intermediate 23

Synthesis Example 23

Synthesis of Intermediate 24

A reaction was performed in the same manner as in Synthesis Example 22 except that 20.7 g of 2-bromonaphthalene were used instead of 20.7 g of 1-bromonaphthalene. As a result, 7.6 g of Intermediate 24 shown below as a white powder were obtained. FD-MS analysis resulted in 1:1 peaks at m/z=282 and 284 for $C_{16}H_{11}Br=283$, so the resultant powder was identified as Intermediate 24 shown below.

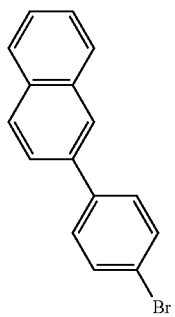

Intermediate 24

Synthesis Example 24

Synthesis of Intermediate 25

A reaction was performed in the same manner as in Synthesis Example 22 except that 34.0 g of 4'-iodobromobenzene were used instead of 26.5 g of 4-iodobromobenzene. As a result, 10.1 g of Intermediate 25 shown below as a white powder were obtained. FD-MS analysis resulted in 1:1 peaks at m/z=358 and 360 for $C_{22}H_{15}Br=359$, so the resultant powder was identified as Intermediate 25 shown below.

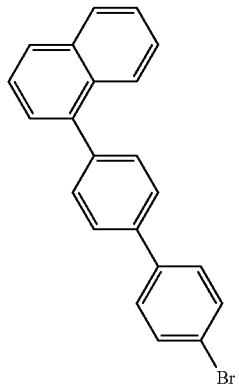

Intermediate 25

Synthesis Example 25

Synthesis of Intermediate 26

A reaction was performed in the same manner as in Synthesis Example 6 except that 21.4 g of 2-bromonaphthalene were used instead of 10 g of 4-bromobiphenyl. As a result, 8.1 g of Intermediate 26 shown below as a white powder were obtained. FD-MS analysis resulted in a main peak at m/z=269 for $C_{20}H_{15}Br=269$, so the resultant powder was identified as Intermediate 26 shown below.

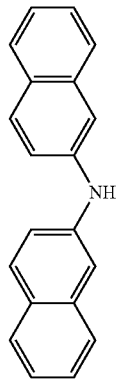

Intermediate 26

Synthesis Example 26

Synthesis of Intermediate 27

A reaction was performed in the same manner as in Synthesis Example 6 except that 26.1 g of Intermediate 23 were used instead of 10 g of 4-bromobiphenyl. As a result, 9.6 g of Intermediate 27 shown below as a white powder were obtained. FD-MS analysis resulted in a main peak at m/z=421 for $C_{32}H_{32}Br=421$, so the resultant powder was identified as Intermediate 27 shown below.

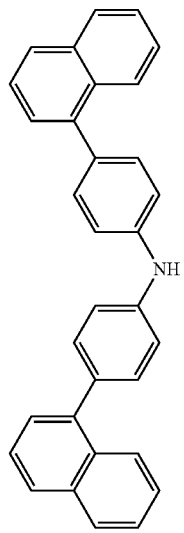

Intermediate 27

Synthesis Example 27

Synthesis of Intermediate 28

A reaction was performed in the same manner as in Synthesis Example 2 except that: 7.6 g of 4-amino-p-terphenyl were used instead of 10 g of di-4-biphenylylamine; and 9.6 g of 4-bromo-p-terphenyl were used instead of 9.7 g of 4,4'-dibromobiphenyl. As a result, 6.2 g of Intermediate 28 shown below as a white powder were obtained. FD-MS analysis resulted in a main peak at m/z=473 for $C_{36}H_{27}N=473$, so the resultant powder was identified as Intermediate 28 shown below.

Intermediate 28

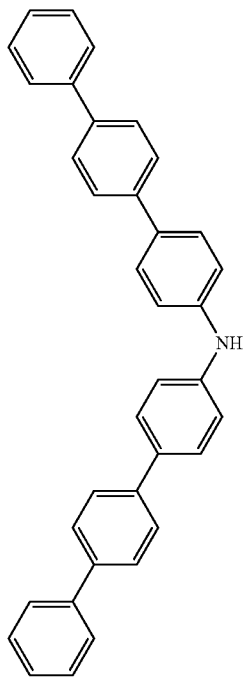

Synthesis Example 28

Synthesis of Intermediate 29

A reaction was performed in the same manner as in Synthesis Example 2 except that: 2.9 g of aniline were used instead of 10 g of di-4-biphenylylamine; and 8.8 g of Intermediate 21 were used instead of 9.7 g of 4,4'-dibromobiphenyl. As a result, 4.2 g of Intermediate 29 shown below as a white powder were obtained. FD-MS analysis resulted in a main peak at m/z=295 for $C_{22}H_{17}N=295$, so the resultant powder was identified as Intermediate 29 shown below.

Intermediate 29

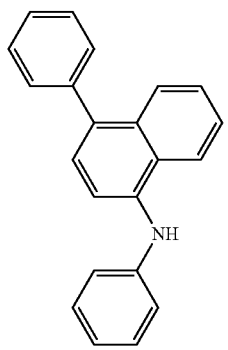

Synthesis Example 29

Synthesis of Intermediate 30

A reaction was performed in the same manner as in Synthesis Example 28 except that 11.1 g of Intermediate 22 were used instead of 8.8 g of Intermediate 21. As a result, 5.7 g of Intermediate 30 shown below as a white powder were obtained. FD-MS analysis resulted in a main peak at m/z=371 for $C_{28}H_{21}N=371$, so the resultant powder was identified as Intermediate 30 shown below.

Intermediate 30

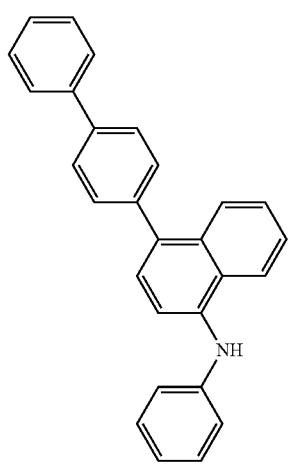

Synthesis Example 30

Synthesis of Intermediate 31

A reaction was performed in the same manner as in Synthesis Example 28 except that 8.8 g of Intermediate 23 were used instead of 8.8 g of Intermediate 21. As a result, 4.0 g of Intermediate 31 shown below as a white powder were obtained. FD-MS analysis resulted in a main peak at m/z=295 for $C_{22}H_{17}N=295$, so the resultant powder was identified as Intermediate 31 shown below.

Intermediate 31

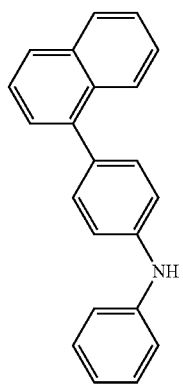

Synthesis Example 31

Synthesis of Intermediate 32

A reaction was performed in the same manner as in Synthesis Example 28 except that 8.8 g of Intermediate 24 were used instead of 8.8 g of Intermediate 21. As a result, 3.6 g of Intermediate 32 shown below as a white powder were obtained. FD-MS analysis resulted in a main peak at m/z=295 for $C_{22}H_{17}N=295$, so the resultant powder was identified as Intermediate 32 shown below.

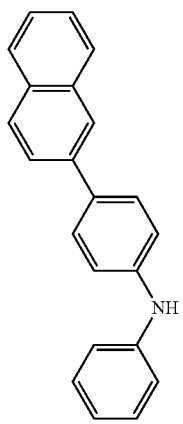

Intermediate 32

Synthesis Example 32

Synthesis of Intermediate 33

A reaction was performed in the same manner as in Synthesis Example 28 except that 11.1 g of Intermediate 22 were used instead of 8.8 g of Intermediate 21. As a result, 6.2 g of Intermediate 33 shown below as a white powder were obtained. FD-MS analysis resulted in a main peak at m/z=371 for $C_{28}H_{21}N=371$, so the resultant powder was identified as Intermediate 33 shown below.

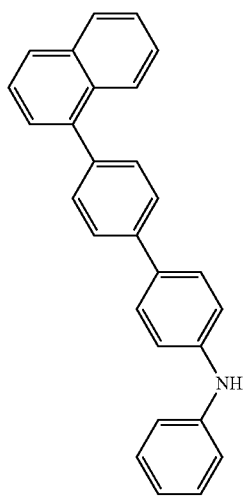

Intermediate 33

Synthesis Example 33

Synthesis of Intermediate 34

A reaction was performed in the same manner as in Synthesis Example 27 except that 4.9 g of bromobenzene were used instead of 9.6 g of 4-bromo-p-terphenyl. As a result, 3.9 g of Intermediate 34 shown below as a white powder were obtained. FD-MS analysis resulted in a main peak at m/z=321 for $C_{24}H_{19}N=321$, so the resultant powder was identified as Intermediate 34 shown below.

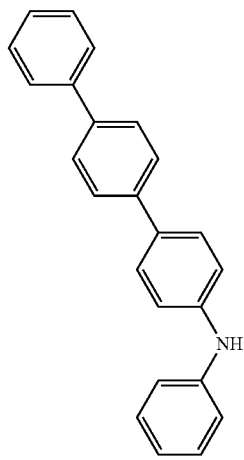

Intermediate 34

Synthesis Example 34

Synthesis of Intermediate 35

A reaction was performed in the same manner as in Synthesis Example 27 except that 6.4 g of 1-bromonaphthalene were used instead of 9.6 g of 4-bromo-p-terphenyl. As a result, 3.8 g of Intermediate 34 shown below as a white powder were obtained. FD-MS analysis resulted in a main peak at m/z=371 for $C_{28}H_{21}N=371$, so the resultant powder was identified as Intermediate 35 shown below.

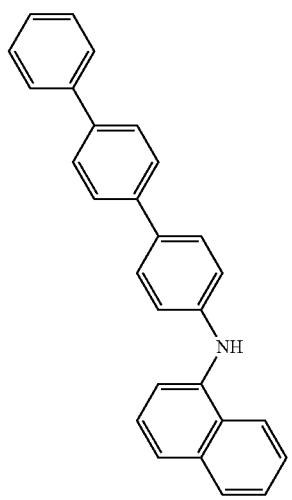

Intermediate 35

Synthesis Example 35

Synthesis of Intermediate 36

In a stream of argon, 11.1 g of N-phenyl-1-naphthylamine, 15.6 g of 4-iodobromobiphenyl, 1.9 g of copper(I) iodide (manufactured by Wako Pure Chemical Industries, Ltd.), 2.0 g of N,N'-dimethylethylenediamine (manufactured by SIGMA-ALDRICH), 8.6 g of t-butoxysodium (manufactured by TOKYO CHEMICAL INDUSTRY CO., LTD.), and 100 mL of dehydrated toluene were loaded into a 300-mL three-necked flask, and the whole was subjected to a reaction at 110° C. for 8 hours. After the completion of the reaction, the resultant was extracted with toluene and dried with magnesium sulfate. The dried product was condensed under reduced pressure, and the resultant crude product was subjected to column purification. The purified product was recrystallized with toluene. The crystal was taken by filtration, and was then dried, whereby 16.8 g of a white powder were obtained.

In a stream of argon, 16.8 g of the above-mentioned white powder and 100 mL of dehydrated xylene were added to a 300-mL three-necked flask, and the whole was cooled to −30° C. 30 mL of n-butyllithium (1.6-M hexane solution) were charged into the mixture, and the whole was subjected to a reaction for 1 hour. After the resultant had been cooled to −70° C., 28 mL of triisopropyl borate (manufactured by TOKYO CHEMICAL INDUSTRY CO., LTD.) were loaded into the resultant. The resultant was slowly heated, and was stirred at room temperature for 1 hour. 32 mL of a 10% hydrochloric acid solution were added to the resultant, and the whole was stirred. The resultant was extracted with ethyl acetate and water, and an organic layer was washed with water. The resultant was dried with anhydrous sodium sulfate, and the solvent was removed by distillation. The resultant was washed with hexane, whereby 7.5 g of a white powder were obtained.

Intermediate 36

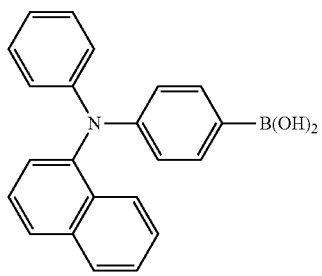

Example of Synthesis 1

Synthesis of Compound H1

In a stream of argon, 3.1 g of Intermediate 1, 3.6 g of Intermediate 3, 2.0 g of t-butoxysodium (manufactured by HIROSHIMA WAKO CO., LTD.), 0.33 g of bis(triphenylphosphine)palladium(II) chloride (manufactured by TOKYO CHEMICAL INDUSTRY CO., LTD.), and 300 mL of xylene were loaded, and the whole was subjected to a reaction at 130° C. for 24 hours.

After having been cooled, the resultant was added with 500 ml of water, and the mixture was subjected to Celite filtration. The filtrate was extracted with toluene and dried with anhydrous magnesium sulfate. The resultant was concentrated under reduced pressure, and the resultant crude product was subjected to column purification. Then, the resultant was recrystallized with toluene, and the recrystallized product was separated by filtration and dried, thereby yielding 4.1 g of pale yellow powder. The powder was identified as Compound H1 to be described below because a main peak of m/z=690 was obtained for $C_{52}H_{38}N_2$=690 as a result of FD-MS (field desorption mass spectrometry) analysis.

Compound H1

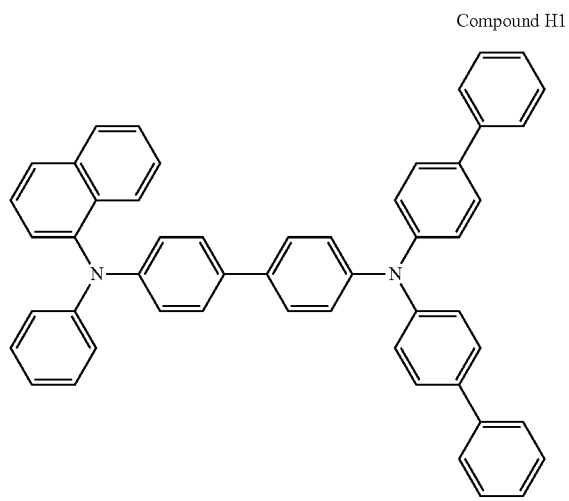 [SMILES: c1ccc(-c2ccc(N(c3ccc(-c4ccccc4)cc3)c3ccc(-c4ccc(N(c5ccccc5)c5cccc6ccccc56)cc4)cc3)cc2)cc1]

Example of Synthesis 2

Synthesis of Compound H2

A reaction was performed in the same manner as in Example of Synthesis 1 except that 3.7 g of Intermediate 9 were used instead of Intermediate 1, thereby yielding 3.1 g of pale yellow powder. The powder was identified as Compound H2 to be described below because a main peak of m/z=664 was obtained for $C_{50}H_{36}N_2$=664 as a result of FD-MS analysis.

Compound H2

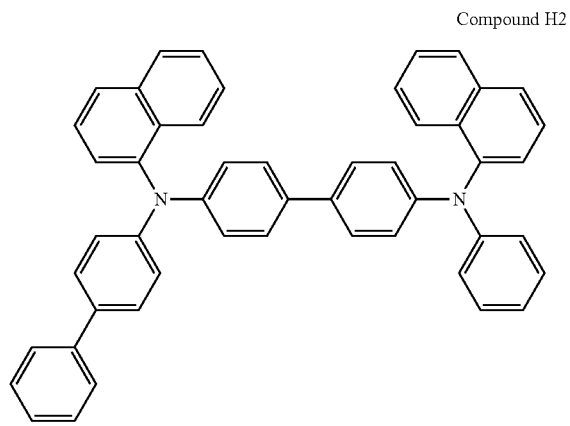 [SMILES: c1ccc(-c2ccc(N(c3ccc(-c4ccc(N(c5ccccc5)c5cccc6ccccc56)cc4)cc3)c3cccc4ccccc34)cc2)cc1]

Example of Synthesis 3

Synthesis of Compound H3

A reaction was performed in the same manner as in Example of Synthesis 1 except that 4.3 g of Intermediate 13 were used instead of Intermediate 1, thereby yielding 4.1 g of pale yellow powder. The powder was identified as Compound H3 to be described below because a main peak of m/z=714 was obtained for $C_{54}H_{38}N_2=714$ as a result of FD-MS analysis.

Compound H3

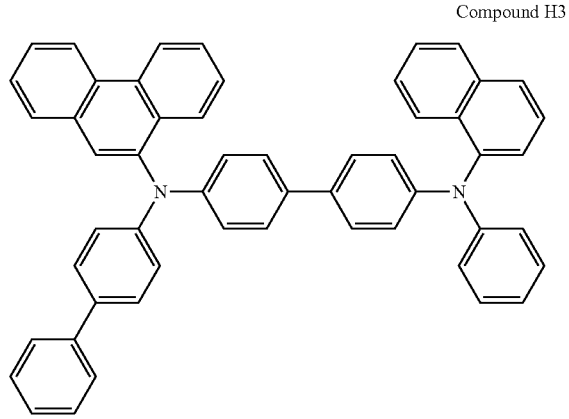 [SMILES: c1ccc(-c2ccc(N(c3ccc(-c4ccc(N(c5ccccc5)c5cccc6ccccc56)cc4)cc3)c3cc4ccccc4c4ccccc34)cc2)cc1]

Example of Synthesis 4

Synthesis of Compound H4

A reaction was performed in the same manner as in Example of Syntheses 1 except that 3.6 g of Intermediate 10 used instead of Intermediate 1, thereby yielding 3.9 g of pale yellow powder. The powder was identified as Compound H4 to be described below because a main peak of m/z=691 was obtained for $C_{56}H_{40}N_2=740$ as a result of FD-MS analysis.

Compound H4

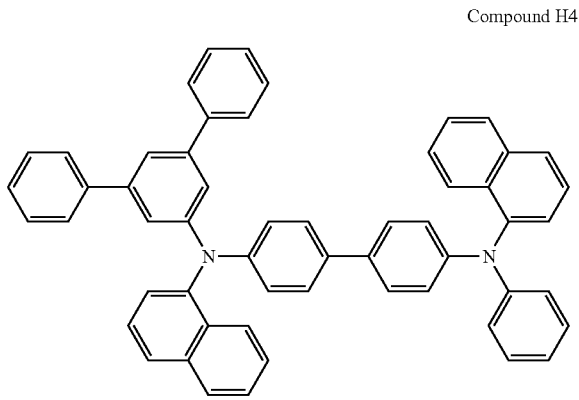 [SMILES: c1ccc(-c2cc(-c3ccccc3)cc(N(c3ccc(-c4ccc(N(c5ccccc5)c5cccc6ccccc56)cc4)cc3)c3cccc4ccccc34)c2)cc1]

Example of Synthesis 5

Synthesis of Compound H5

A reaction was performed in the same manner as in Example of Synthesis 1 except that 3.6 g of Intermediate 10 were used instead of Intermediate 1 and 4.4 g of Intermediate 2 were used instead of Intermediate 3, thereby yielding 4.1 g of pale yellow powder. The powder was identified as Compound H5 to be described below because a main peak of m/z=842 was obtained for $C_{64}H_{46}N_2=842$ as a result of FD-MS analysis.

Compound H5

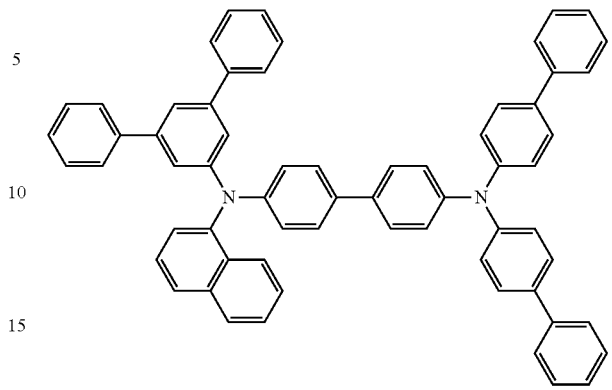

Example of Synthesis 6

Synthesis of Compound H6

A reaction was performed in the same manner as in Example of Synthesis 1 except that 3.8 g of Intermediate 14 were used instead of Intermediate 1, thereby yielding 3.7 g of pale yellow powder. The powder was identified as Compound H6 to be described below because a main peak of m/z=766 was obtained for $C_{56}H_{42}N_2=766$ as a result of FD-MS analysis.

Compound H6

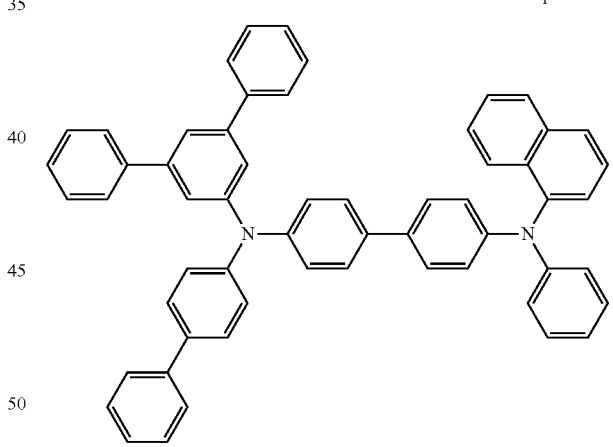

Example of Synthesis 7

Synthesis of Compound H7

A reaction was performed in the same manner as in Example of Synthesis 1 except that 3.6 g of Intermediate 11 were used instead of Intermediate 1 and 4.4 g of Intermediate 2 were used instead of Intermediate 3, thereby yielding 4.8 g of pale yellow powder. The powder was identified as Compound H7 to be described below because a main peak of m/z=842 was obtained for $C_{64}H_{46}N_2=842$ as a result of FD-MS analysis.

Compound H7

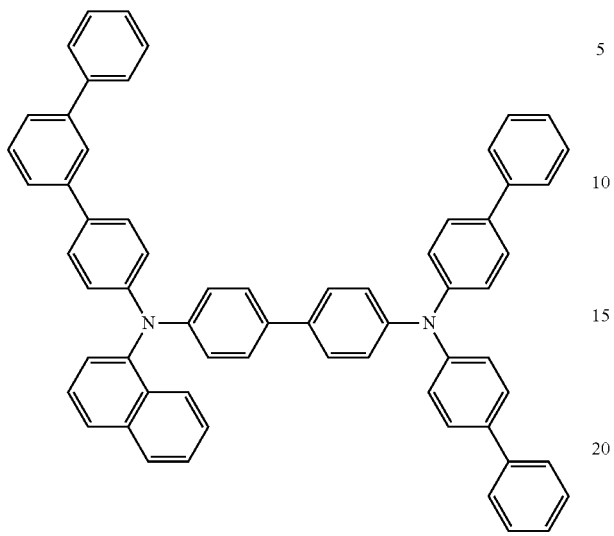

Example of Synthesis 8

Synthesis of Compound H8

A reaction was performed in the same manner as in Example of Synthesis 1 except that 3.8 g of Intermediate 15 were used instead of Intermediate 1, thereby yielding 4.8 g of pale yellow powder. The powder was identified as Compound H8 to be described below because a main peak of m/z=766 was obtained for $C_{58}H_{42}N_2$=766 as a result of FD-MS analysis.

Compound H8

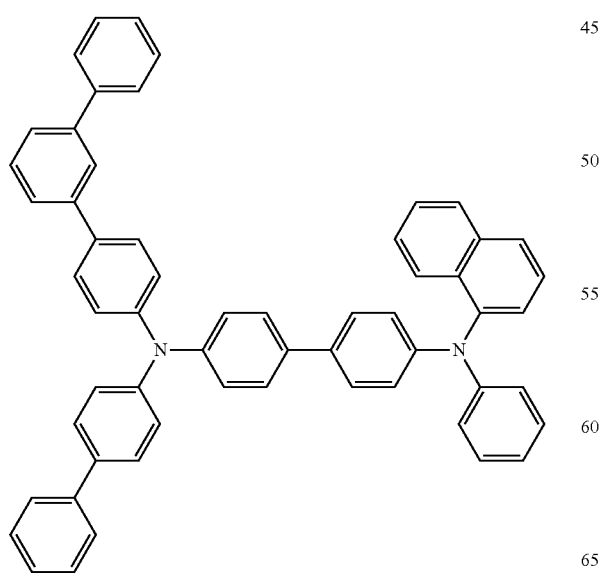

Example of Synthesis 9

Synthesis of Compound H9

A reaction was performed in the same manner as in Example of Synthesis 1 except that 4.5 g of Intermediate 19 were used instead of Intermediate 1, thereby yielding 4.2 g of pale yellow powder. The powder was identified as Compound H9 to be described below because a main peak of m/z=842 was obtained for $C_{64}H_{46}N_2$=842 as a result of FD-MS analysis.

Compound H9

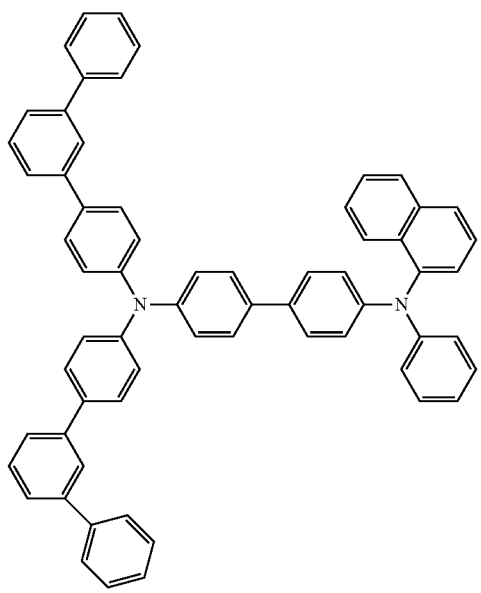

Example of Synthesis 10

Synthesis of Compound H10

A reaction was performed in the same manner as in Example of Synthesis 1 except that 3.6 g of Intermediate 12 were used instead of Intermediate 1, thereby yielding 4.2 g of pale yellow powder. The powder was identified as Compound H10 to be described below because a main peak of m/z=744 was obtained for $C_{56}H_{44}N_2$=744 as a result of FD-MS analysis.

Compound H10

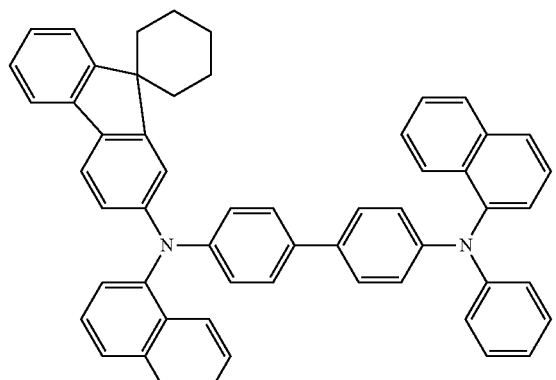

Example of Synthesis 11

Synthesis of Compound H11

A reaction was performed in the same manner as in Example of Synthesis 1 except that 3.6 g of Intermediate 12 were used instead of Intermediate 1 and 4.4 g of Intermediate 2 were used instead of Intermediate 3, thereby yielding 4.1 g of pale yellow powder. The powder was identified as Compound H11 to be described below because a main peak of m/z=846 was obtained for $C_{64}H_{50}N_2$=846 as a result of FD-MS analysis.

Compound H11

Example of Synthesis 12

Synthesis of Compound H12

A reaction was performed in the same manner as in Example of Synthesis 1 except that 3.8 g of Intermediate 16 were used instead of Intermediate 1, thereby yielding 4.5 g of pale yellow powder. The powder was identified as Compound H12 to be described below because a main peak of m/z=770 was obtained for $C_{58}H_{46}N_2$=770 as a result of FD-MS analysis.

Compound H12

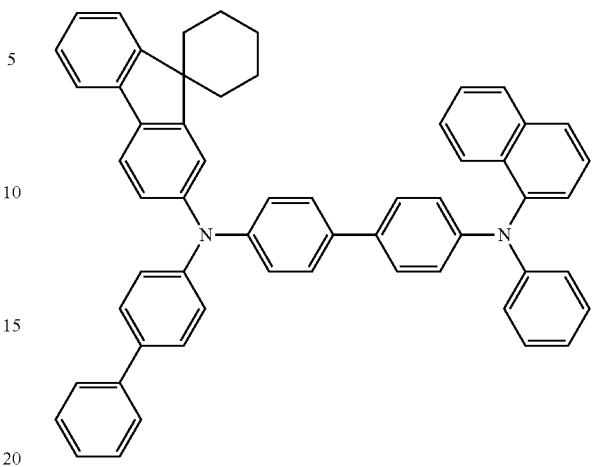

Example of Synthesis 13

Synthesis of Compound H13

A reaction was performed in the same manner as in Example of Synthesis 1 except that 4.6 g of Intermediate 20 were used instead of Intermediate 1, thereby yielding 4.2 g of pale yellow powder. The powder was identified as Compound H13 to be described below because a main peak of m/z=850 was obtained for $C_{64}H_{54}N_2$=850 as a result of FD-MS analysis.

Compound H13

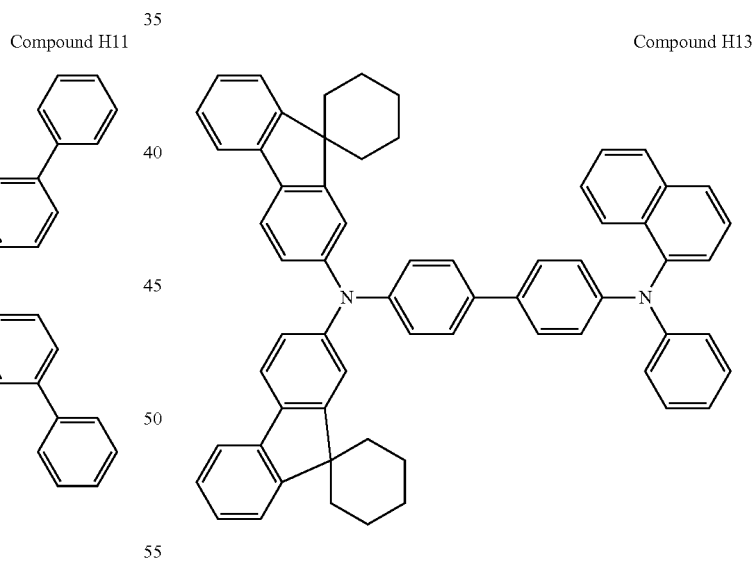

Example of Synthesis 14

Synthesis of Compound H14

A reaction was performed in the same manner as in Example of Synthesis 1 except that 3.7 g of Intermediate 17 were used instead of Intermediate 1, thereby yielding 4.2 g of pale yellow powder. The powder was identified as Compound H14 to be described below because a main peak of m/z=756 was obtained for $C_{57}H_{44}N_2$=756 as a result of FD-MS analysis.

Compound H14

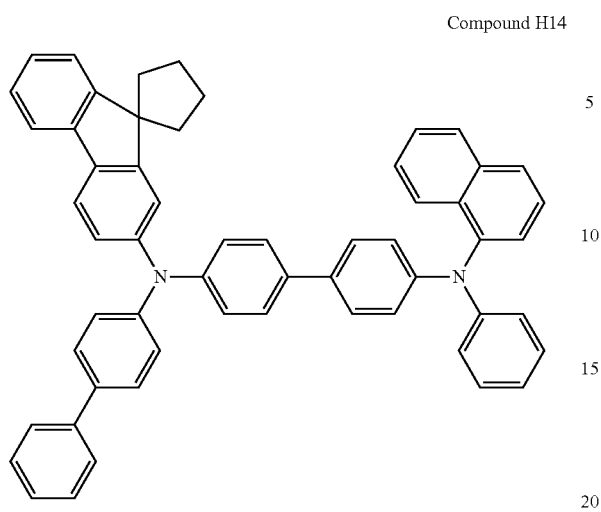

Example of Synthesis 15

Synthesis of Compound H15

A reaction was performed in the same manner as in Example of Synthesis 1 except that 3.5 g of Intermediate 18 were used instead of Intermediate 1, thereby yielding 3.9 g of pale yellow powder. The powder was identified as Compound H15 to be described below because a main peak of m/z=730 was obtained for $C_{55}H_{42}N_2$=730 as a result of FD-MS analysis.

Compound H15

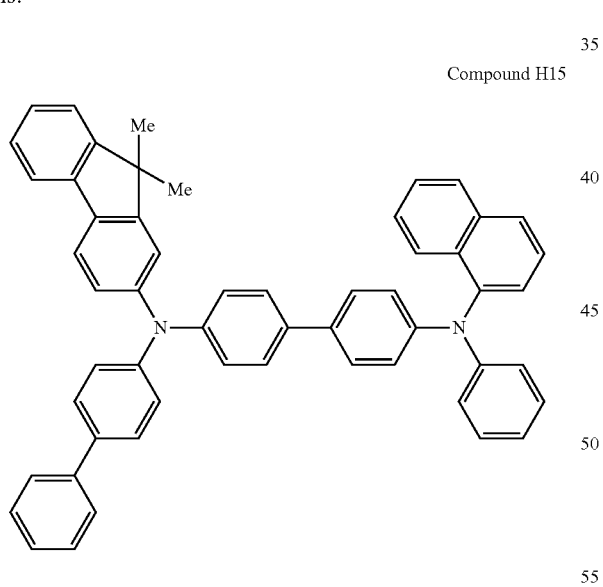

Example of Synthesis 16

Synthesis of Compound H16

A reaction was performed in the same manner as in Example of Synthesis 1 except that 2.7 g of Intermediate 26 were used instead of Intermediate 1, thereby yielding 3.1 g of pale yellow powder. The powder was identified as Compound H16 to be described below because a main peak of m/z=638 was obtained for $C_{48}H_{34}N_2$=638 as a result of FD-MS analysis.

H16

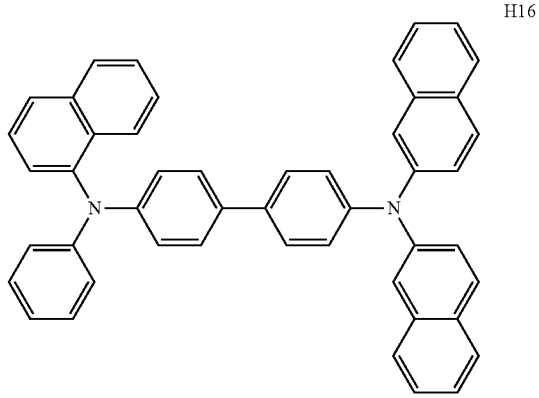 [SMILES: c1ccc(N(c2ccc(-c3ccc(N(c4ccc5ccccc5c4)c4ccc5ccccc5c4)cc3)cc2)c2cccc3ccccc23)cc1]

Example of Synthesis 17

Synthesis of Compound H17

A reaction was performed in the same manner as in Example of Synthesis 1 except that 4.2 g of Intermediate 27 were used instead of Intermediate 1, thereby yielding 4.1 g of pale yellow powder. The powder was identified as Compound H17 to be described below because a main peak of m/z=790 was obtained for $C_{60}H_{42}N_2$=790 as a result of FD-MS analysis.

H17

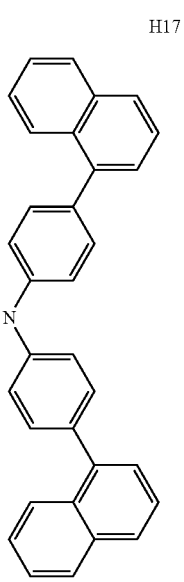

Example of Synthesis 18

Synthesis of Compound H18

A reaction was performed in the same manner as in Example of Synthesis 1 except that 4.7 g of Intermediate 28 were used instead of Intermediate 1, thereby yielding 3.9 g of pale yellow powder. The powder was identified as Compound H18 to be described below because a main peak of m/z=842 was obtained for $C_{64}H_{46}N_2$=842 as a result of FD-MS analysis.

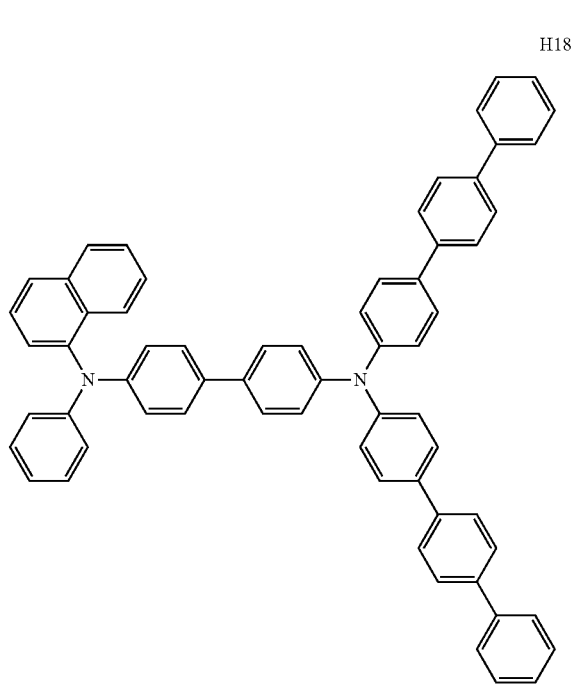 [SMILES: c1ccc(-c2ccc(-c3ccc(N(c4ccc(-c5ccc(-c6ccccc6)cc5)cc4)c4ccc(-c5ccc(N(c6ccccc6)c6cccc7ccccc67)cc5)cc4)cc3)cc2)cc1]

H18

Example of Synthesis 19

Synthesis of Compound H19

A reaction was performed in the same manner as in Example of Synthesis 5 except that 3.0 g of Intermediate 29 were used instead of Intermediate 10, thereby yielding 3.0 g of pale yellow powder. The powder was identified as Compound H19 to be described below because a main peak of m/z=766 was obtained for $C_{58}H_{42}N_2=766$ as a result of FD-MS analysis.

H19

Example of Synthesis 20

Synthesis of Compound H2O

A reaction was performed in the same manner as in Example of Synthesis 5 except that 3.7 g of Intermediate 30 were used instead of Intermediate 10, thereby yielding 2.8 g of pale yellow powder. The powder was identified as Compound H2O to be described below because a main peak of m/z=843 was obtained for $C_{64}H_{46}N_2=843$ as a result of FD-MS analysis.

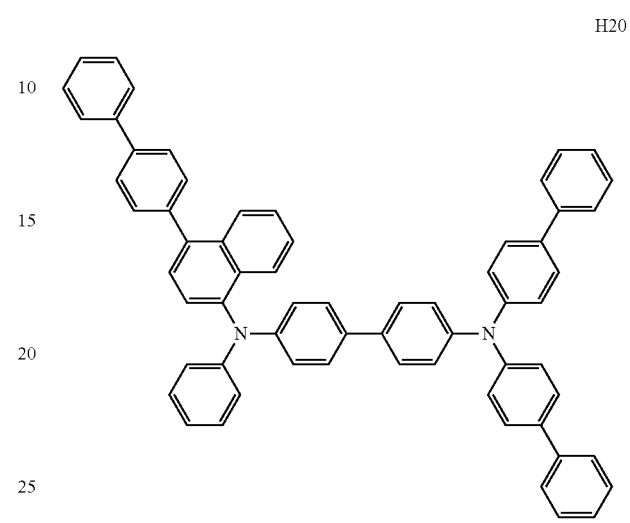

H20

Example of Synthesis 21

Synthesis of Compound H21

A reaction was performed in the same manner as in Example of Synthesis 5 except that 3.0 g of Intermediate 31 were used instead of Intermediate 10, thereby yielding 2.9 g of pale yellow powder. The powder was identified as Compound H21 to be described below because a main peak of m/z=766 was obtained for $C_{58}H_{42}N_2=766$ as a result of FD-MS analysis.

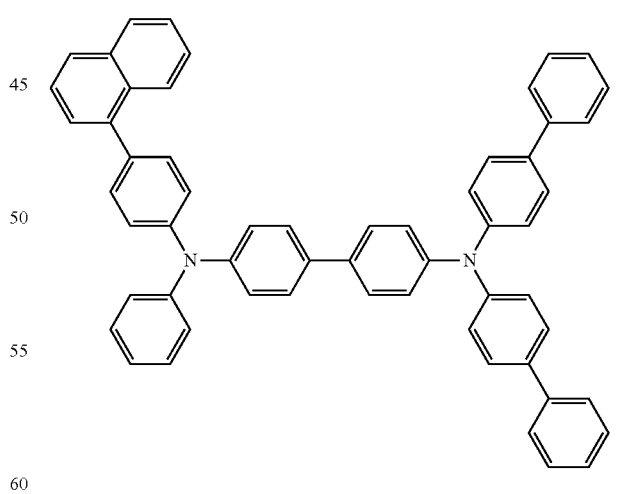

H21

Example of Synthesis 22

Synthesis of Compound H22)

A reaction was performed in the same manner as in Example of Synthesis 5 except that 3.0 g of Intermediate 32 were used instead of Intermediate 10, thereby yielding 3.2 g of pale yellow powder. The powder was identified as Compound H22 to be described below because a main peak of m/z=766 was obtained for $C_{58}H_{42}N_2$=766 as a result of FD-MS analysis.

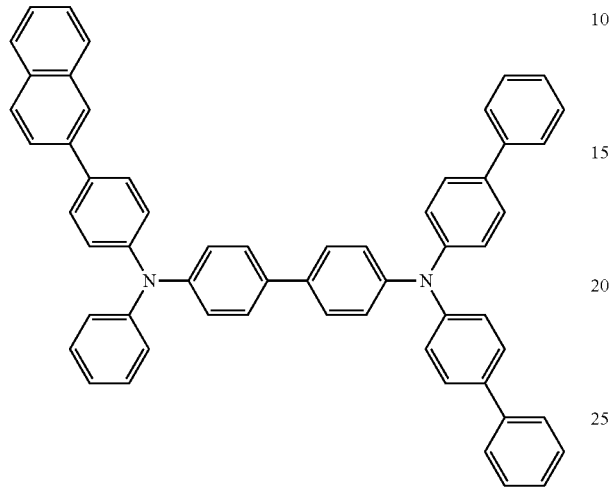

H22

Example of Synthesis 23

Synthesis of Compound H23

A reaction was performed in the same manner as in Example of Synthesis 5 except that 3.7 g of Intermediate 33 were used instead of Intermediate 10, thereby yielding 3.1 g of pale yellow powder. The powder was identified as Compound H23 to be described below because a main peak of m/z=843 was obtained for $C_{64}H_{46}N_2$=843 as a result of FD-MS analysis.

H23

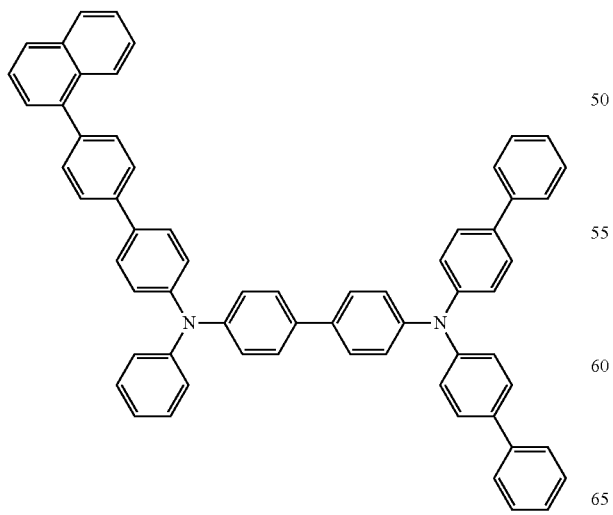

Example of Synthesis 24

Synthesis of Compound H24

A reaction was performed in the same manner as in Example of Synthesis 5 except that 3.2 g of Intermediate 34 were used instead of Intermediate 10, thereby yielding 3.6 g of pale yellow powder. The powder was identified as Compound H24 to be described below because a main peak of m/z=793 was obtained for $C_{60}H_{44}N_2$=793 as a result of FD-MS analysis.

H24

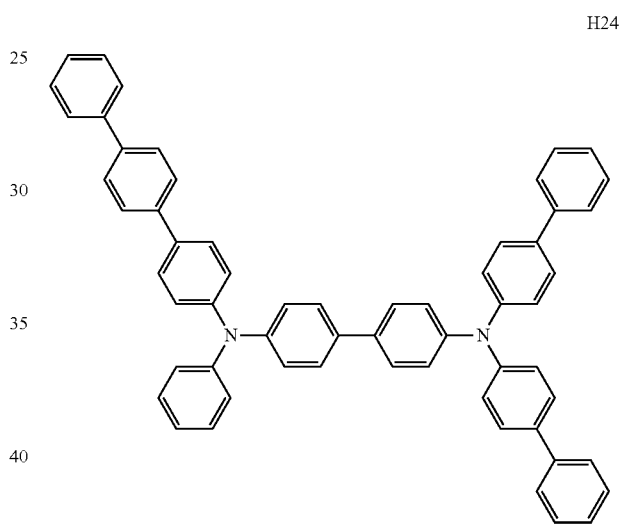

Example of Synthesis 25

Synthesis of Compound H25

A reaction was performed in the same manner as in Example of Synthesis 5 except that 3.7 g of Intermediate 35 were used instead of Intermediate 10, thereby yielding 3.5 g of pale yellow powder. The powder was identified as Compound H25 to be described below because a main peak of m/z=843 was obtained for $C_{64}H_{46}N_2$=843 as a result of FD-MS analysis.

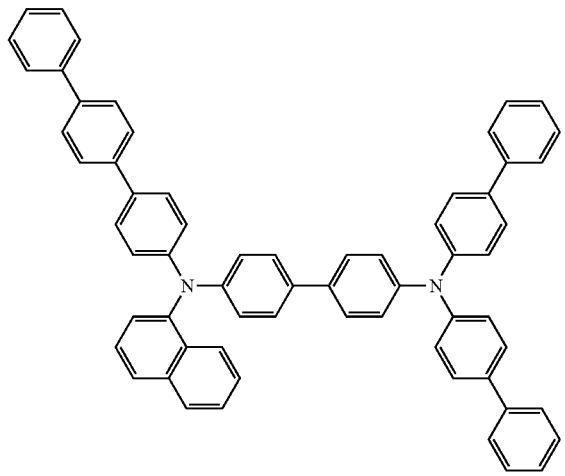

Example of Synthesis 26

Synthesis of Compound H26

In a stream of argon, 3.4 g of Intermediate 36, 5.4 of Intermediate 2, 0.26 g of tetrakis(triphenylphosphine) palladium (O), 3.18 g of sodium carbonate, 50 mL of 1,2-dimethoxyethane, and 30 mL of water were added to a 300-mL three-necked flask, and the whole was refluxed for 8 hours. The resultant was extracted with toluene, and an organic layer was washed with water. The resultant was dried with anhydrous sodium sulfate, and the solvent was removed by distillation. The resultant was recrystallized with toluene/hexane, whereby 3.6 g of a pale yellow powder were obtained. FD-MS analysis resulted in a main peak at m/z=766 for $C_{58}H_{442}N_2$=766, so the resultant powder was identified as Compound H26 described below.

factured by GEOMATEC Co., Ltd.) was subjected to ultrasonic cleaning in isopropyl alcohol for 5 minutes. After that, the substrate was subjected to UV ozone cleaning for 30 minutes.

The glass substrate with the transparent electrode line after the washing was mounted on a substrate holder of a vacuum deposition device. First, Compound H232 to be described below was formed into a film having a thickness of 60 nm on the surface on the side where the transparent electrode line was formed to cover the transparent electrode. The H232 film functions as a hole injecting layer. Compound H1 described above, as a hole transporting material, was formed into a film having a thickness of 20 nm on the H232 film. The film functions as a hole transporting layer. Further, Compound EM1 to be described below was deposited from the vapor and formed into a film having a thickness of 40 nm. Simultaneously with this formation, Amine Compound D1 having a styryl group to be described below, as a light emitting molecule, was deposited from the vapor in such a manner that a weight ratio between Compound EM1 and Amine Compound D1 would be 40:2. The film functions as a light emitting layer.

Alq to be described below was formed into a film having a thickness of 10 nm on the resultant film. The film functions as an electron injecting layer. After that, Li serving as a reducing dopant (Li source: manufactured by SAES Getters) and Alq were subjected to co-deposition. Thus, an Alq:Li film (having a thickness of 10 nm) was formed as an electron injecting layer (cathode). Metal Al was deposited from the vapor onto the Alq:Li film to form a metal cathode. Thus, an organic EL device was formed.

In addition, the current efficiency of the resultant organic EL device was measured, and the luminescent color of the device was observed. A current efficiency at 10 mA/cm² was calculated by measuring a luminance by using a CS1000 manufactured by Minolta. Further, the half lifetime of light emission in DC constant current driving at an initial luminance of 5,000 cd/m² and room temperature was measured. Table 1 shows the results thereof.

Example 1

Production of Organic EL Device

A glass substrate with an ITO transparent electrode measuring 25 mm wide by 75 mm long by 1.1 mm thick (manu-

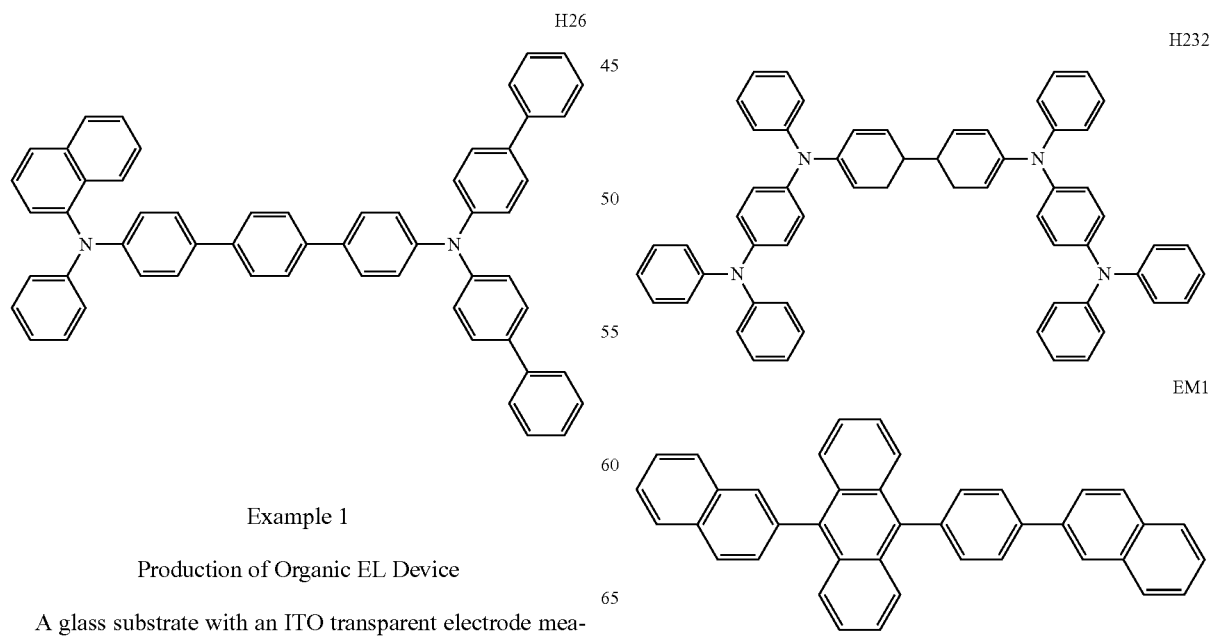

-continued

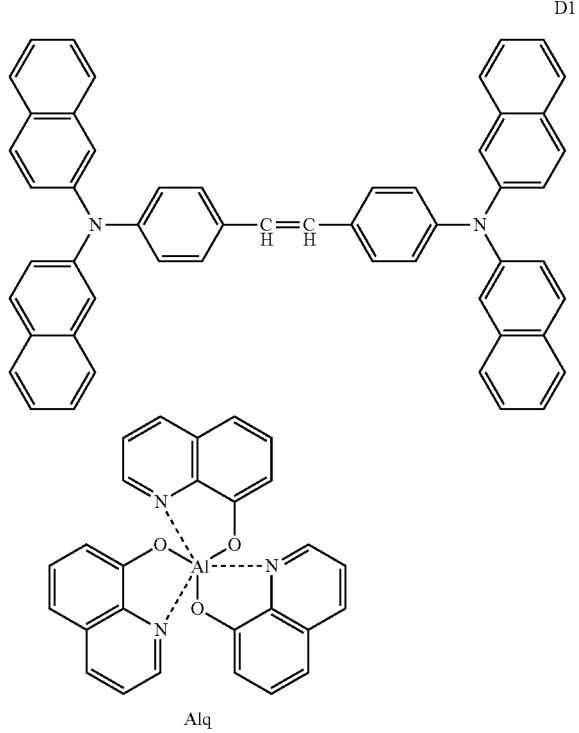

Alq

Examples 2 to 26

Production of Organic EL Devices

Organic EL devices were each produced in the same manner as in Example 1 except that any one of the compounds shown in Table 1 was used as a hole transporting material instead of Compound H1.

Comparative Example 1

An organic EL device was produced in the same manner as in Example 1 except that Comparative Compound 1 was used as a hole transporting material instead of Compound H1.

Comparative Compound 1

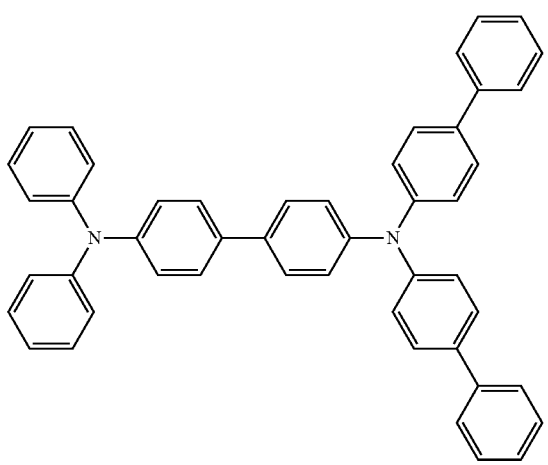

The current efficiency of the resultant organic EL device was measured, and the luminescent color of the device was observed. Further, the half lifetime of light emission in DC constant current driving at an initial luminance of 5,000 cd/m$^2$ and room temperature was measured. Table 1 shows the results thereof.

TABLE 1

| Example | Hole transporting material | Current efficiency (cd/A) | Luminescent color | Half lifetime (hour) |
| --- | --- | --- | --- | --- |
| 1 | H1 | 5 | Blue | 410 |
| 2 | H2 | 4.8 | Blue | 390 |
| 3 | H3 | 4.6 | Blue | 370 |
| 4 | H4 | 5.5 | Blue | 350 |
| 5 | H5 | 5.4 | Blue | 340 |
| 6... | H6... | 5.5... | Blue... | 350... |
| 16 | H16 | 5.4 | Blue | 320 |
| 17 | H17 | 5.2 | Blue | 420 |
| 18 | H18 | 5.1 | Blue | 410 |
| 19 | H19 | 4.9 | Blue | 400 |
| 20 | H20 | 4.9 | Blue | 410 |
| 21 | H21 | 5.3 | Blue | 380 |
| 22 | H22 | 5.2 | Blue | 390 |
| 23 | H23 | 5.0 | Blue | 360 |
| 24 | H24 | 5.1 | Blue | 380 |
| 25 | H25 | 4.9 | Blue | 410 |
| 26 | H26 | 5.3 | Blue | 330 |
| Comparative Example 1 | Comparative Compound 1 | 4.8 | Blue | 260 |

Example 27

Production of Organic EL Device

An organic EL device was produced in the same manner as in Example 1 except that Arylamine Compound D2 to be described below was used instead of Amine Compound D1 having a styryl group. Me represents a methyl group.

The measured current efficiency of the resultant organic EL device was 5.2 cd/A, and the luminescent color of the device was blue. Further, the half lifetime of light emission in DC constant current driving at an initial luminance of 5,000 cd/m$^2$ and room temperature was measured. The measured half lifetime was 400 hours.

Comparative Example 2

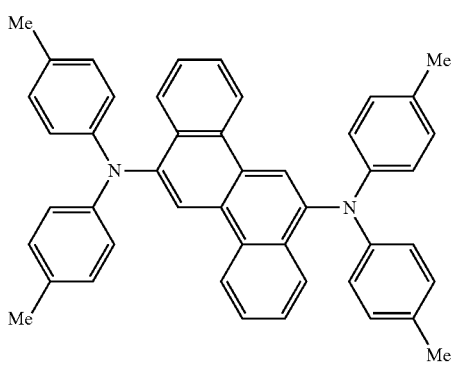

An organic EL device was produced in the same manner as in Example 27 except that Comparative Compound 1 described above was used instead of Compound H1 as a hole transporting material.

The measured current efficiency of the resultant organic EL device was 4.9 cd/A, and the luminescent color of the device was blue. Further, the half lifetime of light emission in DC constant current driving at an initial luminance of 5,000 cd/m² and room temperature was measured. The measured half lifetime was 230 hours.

As can be seen from the above-mentioned results, the use of the aromatic amine derivative of the present invention as a hole transporting material for an organic EL device enables to emit light with luminous efficiency comparable to that of a conventional material, and is extremely effective in lengthening the lifetime.

INDUSTRIAL APPLICABILITY

In the aromatic amine derivative of the present invention and the organic EL device using the derivative of the present invention, molecules are hardly crystallized, and the production yield of the organic EL device is improved. As a result, it becomes possible to provide an organic EL device having a long lifetime.

The invention claimed is:

1. An amine having the following formula:

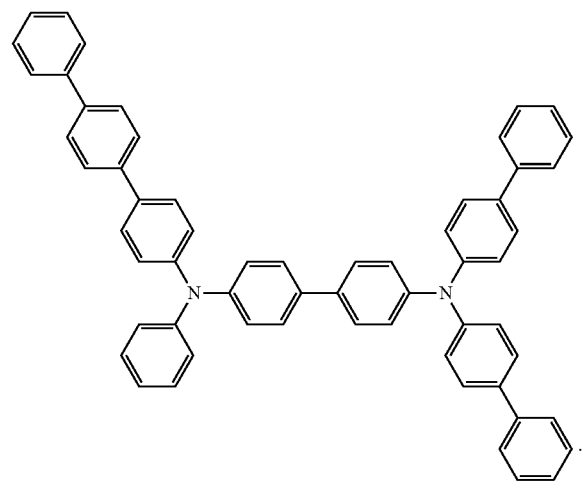 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1]

2. An organic electroluminescence device comprising an organic thin film layer comprising one or more layers comprising at least a light emitting layer, the organic thin film layer being interposed between a cathode and an anode, wherein at least one layer of the organic thin film layer comprises the amine according to claim 1 alone or as a component of a mixture.

3. An organic electroluminescence device comprising an organic thin film layer comprising one or more layers comprising at least a light emitting layer, the organic thin film layer being interposed between a cathode and an anode, wherein the organic thin film layer comprises a hole transporting layer, and wherein the hole transporting layer comprises the amine according to claim 1 alone or as a component of a mixture.

4. The organic electroluminescence device according to claim 2, wherein the light emitting layer comprises an arylamine compound and/or a styrylamine compound.

5. The organic electroluminescence device according to claim 2, wherein the organic electroluminescence device emits bluish light.

6. The organic electroluminescence device according to claim 3, wherein the light emitting layer comprises an arylamine compound and/or a styrylamine compound, and wherein the light emitting layer further comprises an asymmetric anthracene represented by the following formula (i) as host material:

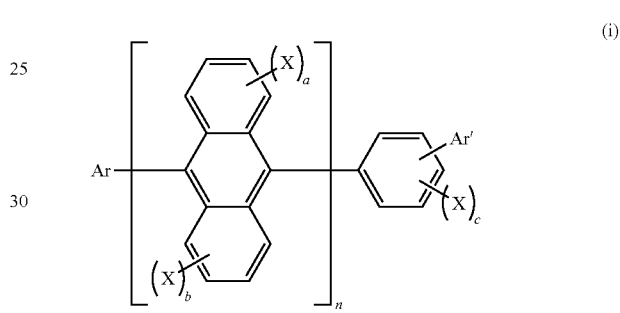

wherein:

Ar represents a substituted or unsubstituted fused aromatic group having 10 to 50 ring carbon atoms;

Ar' represents a substituted or unsubstituted aromatic group having 6 to 50 ring carbon atoms;

X represents a substituted or unsubstituted aromatic group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a carboxyl group, a halogen atom, a cyano group, a nitro group, or a hydroxyl group;

a, b, and c each represent an integer of 0 to 4;

n represents an integer of 1 to 3; and wherein when n represents 2 or more, the anthracene nuclei within the [ ] in formula (i) may be identical to or different from each other.

7. A method for making the amine of claim 1, comprising reacting Intermediate 2 with Intermediate 34:

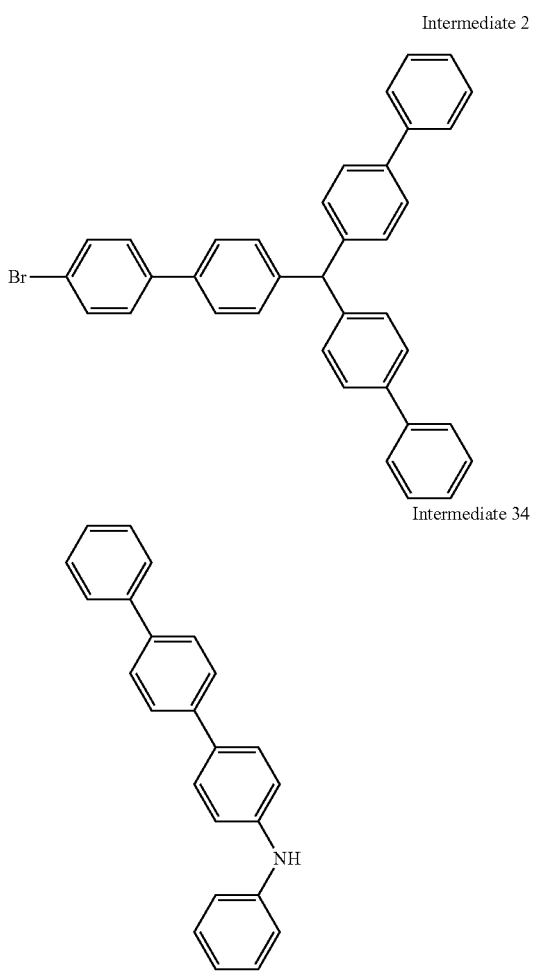

Intermediate 2

Intermediate 34 to produce said amine.

8. The organic electroluminescence device according to claim 2, wherein the light emitting layer comprises at least one selected from the group consisting of anthracene, naphthalene, phenanthrene, pyrene, tetracene, coronene, chrysene, fluoresceine, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, quinoline metal complexes, aminoquinoline metal complexes, benzoquinoline metal complexes, imine, diphenylethylene, vinylanthracene, diaminocarbazole, pyrane, thiopyrane, polymethine, merocyanine, imidazole-chelated oxynoid compounds, quinacridone, rubrene, and fluorescent dyes.

9. An organic electroluminescent fluorescent light emitting device comprising an organic thin film layer comprising one or more layers comprising at least a fluorescent light emitting layer, the organic thin film layer being interposed between a cathode and an anode, wherein the organic thin film layer comprises a hole transporting layer, and wherein the hole transporting layer comprises the amine according to claim 1 alone or as a component of a mixture.

10. An organic electroluminescent bluish fluorescent light emitting device comprising an organic thin film layer comprising one or more layers comprising at least a fluorescent light emitting layer, the organic thin film layer being interposed between a cathode and an anode, wherein the organic thin film layer comprises a hole transporting layer, and wherein the hole transporting layer comprises the amine according to claim 1 alone or as a component of a mixture.

11. An organic electroluminescent phosphorescent light emitting device comprising an organic thin film layer comprising one or more layers comprising at least a phosphorescent light emitting layer, the organic thin film layer being interposed between a cathode and an anode, wherein the organic thin film layer comprises a hole transporting layer, and wherein the hole transporting layer comprises the amine according to claim 1 alone or as a component of a mixture.

12. An organic electroluminescent bluish phosphorescent light emitting device comprising an organic thin film layer comprising one or more layers comprising at least a phosphorescent light emitting layer, the organic thin film layer being interposed between a cathode and an anode, wherein the organic thin film layer comprises a hole transporting layer, wherein the hole transporting layer comprises the amine according to claim 1 alone or as a component of a mixture.

13. An organic electroluminescent phosphorescent light emitting device comprising an organic thin film layer comprising one or more layers comprising at least a phosphorescent light emitting layer, the organic thin film layer being interposed between a cathode and an anode, wherein the organic thin film layer comprises a hole transporting layer, wherein the hole transporting layer comprises the amine according to claim 1 alone or as a component of a mixture and the phosphorescent light emitting layer comprises a compound containing a carbazole ring.

* * * * *